(12) United States Patent
Nakasuji et al.

(10) Patent No.: US 7,439,502 B2
(45) Date of Patent: *Oct. 21, 2008

(54) ELECTRON BEAM APPARATUS AND DEVICE PRODUCTION METHOD USING THE ELECTRON BEAM APPARATUS

(75) Inventors: Mamoru Nakasuji, Kanagawa (JP); Tohru Satake, Kanagawa (JP); Nobuharu Noji, Kanagawa (JP); Hirosi Sobukawa, Kanagawa (JP); Tsutomu Karimata, Kanagawa (JP); Shoji Yoshikawa, Tokyo (JP); Toshifumi Kimba, Kanagawa (JP); Shin Oowada, Kanagawa (JP); Mutsumi Saito, Kanagawa (JP); Muneki Hamashima, Saitama (JP); Yoshiaki Kohama, Kanagawa (JP); Yukiharu Okubo, Saitama (JP)

(73) Assignee: Ebara Corporation, Tokyo (JP)

( * ) Notice: Subject to any disclaimer, the term of this patent is extended or adjusted under 35 U.S.C. 154(b) by 19 days.

This patent is subject to a terminal disclaimer.

(21) Appl. No.: 11/808,497

(22) Filed: Jun. 11, 2007

(65) Prior Publication Data

US 2007/0272859 A1 Nov. 29, 2007

Related U.S. Application Data

(62) Division of application No. 09/985,323, filed on Nov. 2, 2001, now Pat. No. 7,244,932.

(30) Foreign Application Priority Data

| Nov. 2, 2000 | (JP) | ............................... 2000-335939 |
| Dec. 12, 2000 | (JP) | ............................... 2000-378014 |
| Dec. 21, 2000 | (JP) | ............................... 2000-389157 |
| Dec. 22, 2000 | (JP) | ............................... 2000-390873 |
| Dec. 25, 2000 | (JP) | ............................... 2000-392284 |
| Dec. 26, 2000 | (JP) | ............................... 2000-394116 |
| Dec. 26, 2000 | (JP) | ............................... 2000-394123 |
| Dec. 26, 2000 | (JP) | ............................... 2000-394466 |
| Feb. 5, 2001 | (JP) | ............................... 2001-027832 |
| Feb. 8, 2001 | (JP) | ............................... 2001-031901 |
| Feb. 8, 2001 | (JP) | ............................... 2001-031906 |
| Feb. 9, 2001 | (JP) | ............................... 2001-033599 |
| Apr. 13, 2001 | (JP) | ............................... 2001-115156 |
| May 28, 2001 | (JP) | ............................... 2001-158571 |

(51) Int. Cl.
*G01N 23/00* (2006.01)
*G01N 23/22* (2006.01)
*H01J 37/28* (2006.01)
*H01J 37/256* (2006.01)

(52) U.S. Cl. .................. 250/306; 250/307; 250/310; 250/396 R; 250/398; 250/492.2; 250/492.3

(58) Field of Classification Search .............. 250/306, 250/307, 310, 396 R, 398, 492.2, 492.3
See application file for complete search history.

(56) References Cited

U.S. PATENT DOCUMENTS

| 4,944,645 | A | | 7/1990 | Suzuki |
| 4,954,705 | A | | 9/1990 | Brunner et al. |
| 7,109,483 | B2 | * | 9/2006 | Nakasuji et al. .............. 250/310 |
| 7,129,485 | B2 | * | 10/2006 | Nakasuji et al. .............. 250/310 |
| 7,244,932 | B2 | * | 7/2007 | Nakasuji et al. .............. 250/306 |
| 7,247,848 | B2 | * | 7/2007 | Nakasuji et al. .............. 250/306 |

FOREIGN PATENT DOCUMENTS

| EP | 0 999 572 A2 | 5/2000 |
| JP | 61-239624 A | 10/1986 |

OTHER PUBLICATIONS

Electron Ion Beam Handbook, pp. 115-119 (1988) with partial translation.

Search Report dated Jun. 29, 2006 issued in corresponding Japanese Application No. 2002-540181.

* cited by examiner

*Primary Examiner*—Nikita Wells
(74) *Attorney, Agent, or Firm*—Westerman, Hattori, Daniels & Adrian, LLP.

(57) ABSTRACT

The purpose of the invention is to provide an improved electron beam apparatus with improvements in throughput, accuracy, etc. One of the characterizing features of the electron beam apparatus of the present invention is that it has a plurality of optical systems, each of which comprises a primary electron optical system for scanning and irradiating a sample with a plurality of primary electron beams; a detector device for detecting a plurality of secondary beams emitted by irradiating the sample with the primary electron beams; and a secondary electron optical system for guiding the secondary electron beams from the sample to the detector device; all configured so that the plurality of optical systems scan different regions of the sample with their primary electron beams, and detect the respective secondary electron beams emitted from each of the respective regions. This is what makes higher throughput possible. To provide high accuracy, the apparatus is configured such that the axes of its optical systems can be aligned, and aberrations corrected, by a variety of methods.

7 Claims, 53 Drawing Sheets

Fig. 4
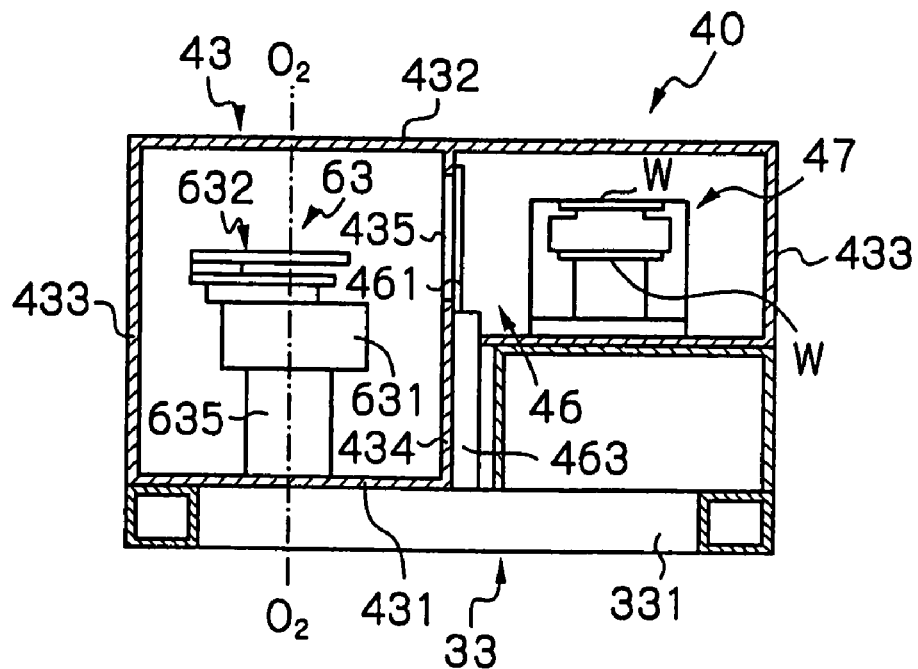
Fig. 5A
Fig. 5B
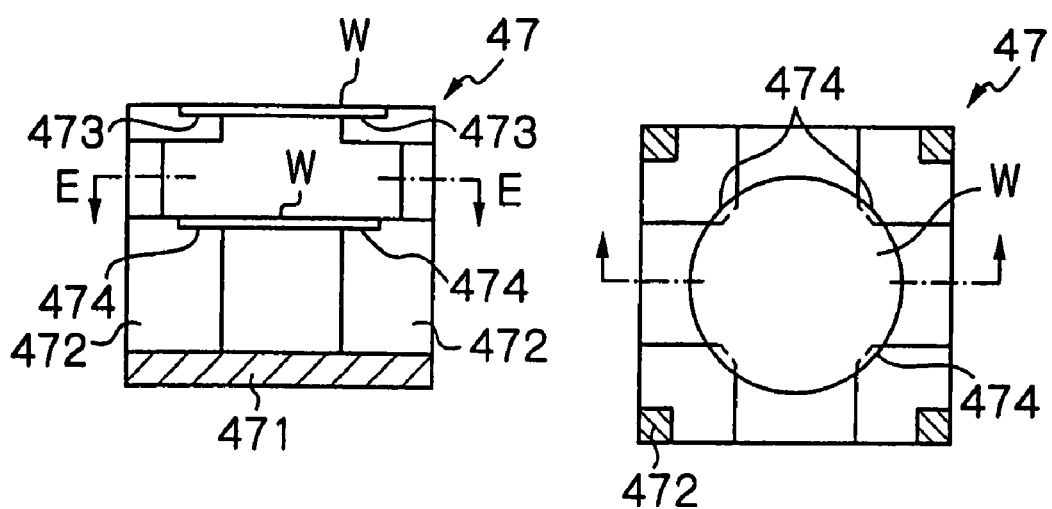

MULTIBEAM(MONO PIXEL)SCAN

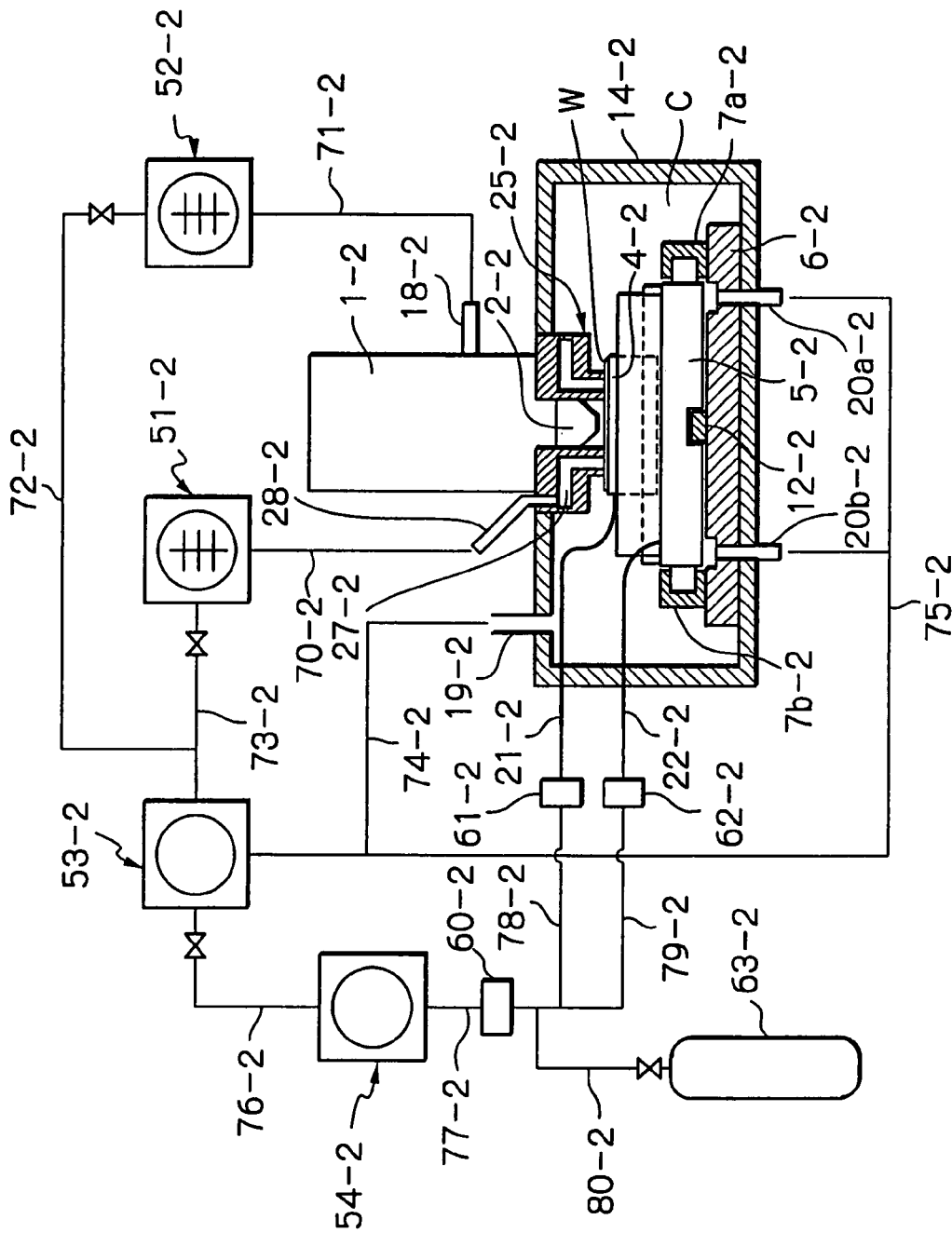

Fig. 53A
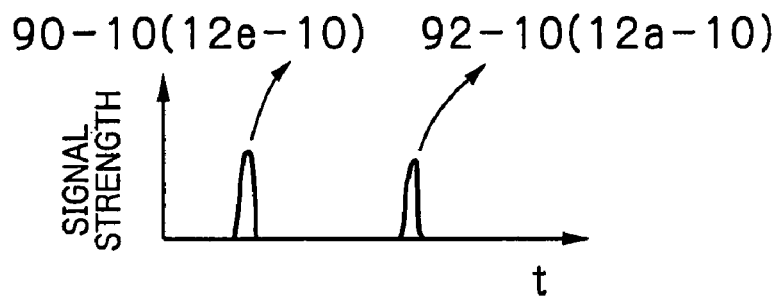
Fig. 53B
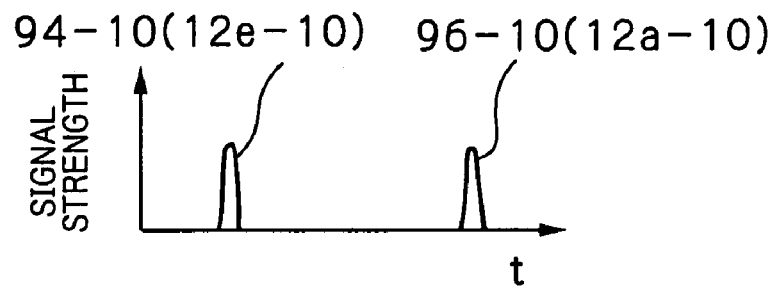
Fig. 53C
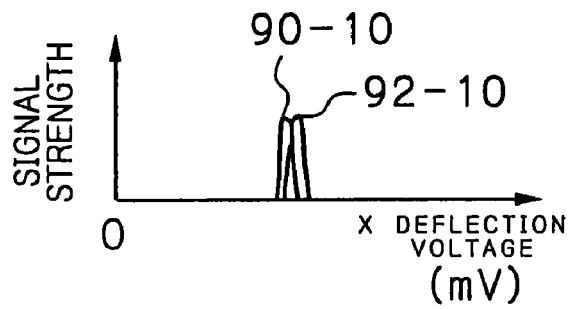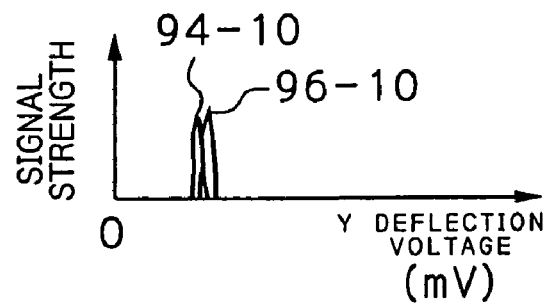

ELECTRON BEAM APPARATUS AND DEVICE PRODUCTION METHOD USING THE ELECTRON BEAM APPARATUS

This application is a divisional of application Ser. No. 09/985,323 filed Nov. 2, 2001.

BACKGROUND OF THE INVENTION

The present invention is related to an apparatus for using a plurality of electron beams to inspect for defects, etc., in patterns formed on the surface of a sample; and in particular, to an apparatus for performing high-throughput wafer defect detection (such as, for example, in a semiconductor device fabrication process) by irradiating the sample with an electron beam; detecting secondary electrons (which vary according to the properties of the surface of the sample); forming image data therefrom; and inspecting and evaluating patterns, etc., formed on the surface of the sample, based on that image data. It is also related to a device fabrication method for high yield production of semiconductor devices, using such an apparatus.

Conventional systems using scanning electron microscopes (SEM) are currently available for performing the above wafer inspection function. These systems form an SEM image by raster-scanning a finely focused electron beam over an extremely closely spaced raster width, while detecting secondary electrons emitted from the sample using a secondary electron detector. Defects are then found by comparing the SEM image with a reference standard image.

Because of the small beam size, pixel size, and raster width used in SEM systems adapted for defect inspection, however, such inspections required a huge amount of time. Also, when the sample was irradiated with a larger beam to improve throughput, this produced degraded spacial resolution quality of the SEM images.

Multibeam inspection systems, in which the sample is irradiated with a number of beams at the same time, have also been in development over the past few years. Many improvements to such systems are needed, however, for realization of high throughput, while also maintaining good precision.

SUMMARY OF THE INVENTION

It is therefore the basic objective of the present invention to make improvements to prior multibeam scanning systems, and more specifically, to provide better throughput.

To achieve this objective, the present invention provides an electron beam inspection apparatus capable of higher throughput. The apparatus comprises a plurality of primary electron optical systems for directing primary electron beams (emitted by an electron gun) toward a sample (such as a wafer); and, a plurality of secondary electron optical systems (columns) for guiding, to a secondary electron detector, secondary electrons emitted by irradiating the sample with the primary electron beams; such that a different region of the sample is inspected by each of the optical systems.

Also, to improve the accuracy of inspections of samples performed using electron beams, the present invention provides an electron beam inspection apparatus configured to provide more precise axial alignment of its electron optical systems. More specifically, alignment of the axes of the multiple beams is performed by adjusting the elements of the optical system such that when voltages applied to the elements (lenses, etc.) of the electron optical system are changed, electron beams that are the same distance from the center of the multiple beams will exhibit substantially the same amount of change in position on the sample.

Also, in a another alignment method of the present invention, axial alignment is performed by detecting the center of an aperture stop at which the image is formed, and adjusting elements of the electron optical system so that secondary electron beams will pass through the center of this aperture stop.

Also, according to one aspect of the multibeam inspection apparatus of the present invention, a multi-aperture plate having a plurality of apertures is used to obtain multiple beams from a single electron gun. In this aspect, the highest intensity portions of the electron beam emitted from the electron gun are aligned with the multi-apertures such as to obtain multi-beam beamlets having high beam currents, in order to establish the good optical conditions for performing inspections.

In addition, provided in another aspect of the multibeam inspection apparatus of the present invention, is an electron beam inspection apparatus in which is provided a correction device for irradiating irradiation design points with primary electron beams, to thereby establish good optical conditions for performing inspections.

The present invention also provides an electron beam inspection apparatus wherein aberrations such as magnification and rotation chromatic aberration can be corrected by adjusting the position along the optical axis of a crossover formed by the primary electron beams.

The present invention also provides an electron beam inspection apparatus in which shot noise is reduced, by establishing conditions such that the electron gun is operated in the space-charge-limited region of its characteristic curve.

The present invention also provides an electron beam inspection apparatus configured for measuring the irradiation dose applied to the sample by the electron beams, and performing control actions to stop operation of the electron beam inspection apparatus when it is determined that the dose is abnormal.

In addition, the present invention provides an electron beam inspection apparatus wherein the electron optical elements such as electron lenses and deflectors that make up its optical systems are constructed such that, rather than using fasteners such as bolts to join the separate insulators and conductors provided therein, conductive layers are formed on required areas of the insulators by electroplating, to thus provide compact electron optical elements of simple construction.

Also provided in the present invention, is a device production method wherein an electron beam inspection apparatus as described above is used to perform in-process inspection of samples such as wafers.

BRIEF DESCRIPTION OF THE DRAWINGS

FIG. 4 is a cross-section view of Section D-D of FIG. 2, showing a loader housing.

FIG. 5(A) is an enlarged side view of a wafer rack.

FIG. 5(B) is a cross-section view of Section E-E of FIG. 5(A).

FIG. 21 shows the gas circulation line system of the apparatus of FIG. 19.

FIG. 53(a) shows the waveform of a signal output when multiple primary beams are scanned over a mark pad along the X axis.

FIG. 53(b) shows the waveform of a signal output when multiple primary beams are scanned over a mark pad along the Y axis.

FIG. 53(c) shows the relationship between deflection voltage and signal strength when the irradiation positions of the primary beams are properly calibrated.

DETAILED DESCRIPTION OF THE PREFERRED EMBODIMENTS

A semiconductor device inspection apparatus that constitutes one embodiment of an electron beam inspection apparatus of the present invention is described below, with reference to the drawings.

Overall Configuration of the Semiconductor Device Inspection Apparatus

Figure 1:
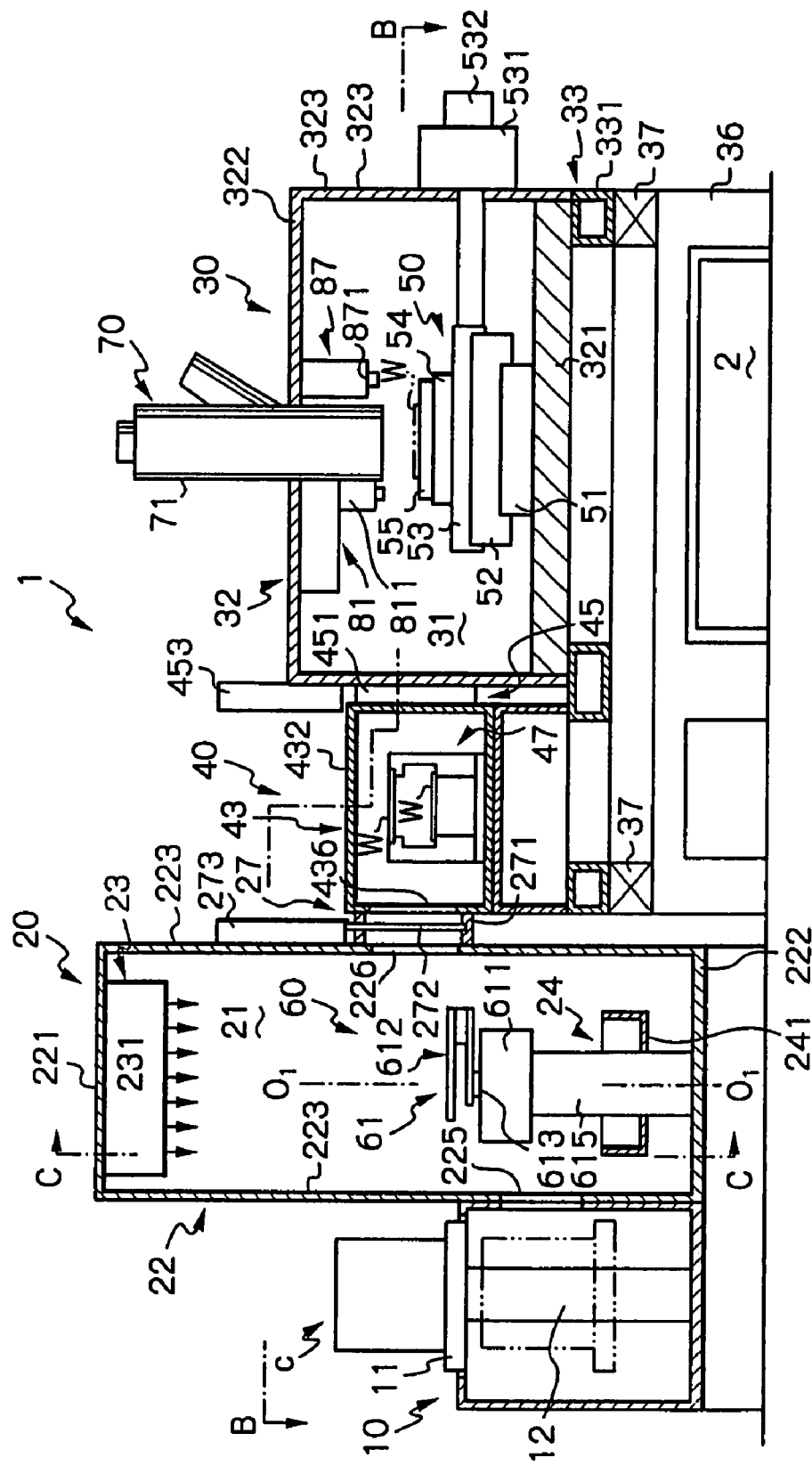
FIG. 1 is an elevation view showing the major components that make up the inspection apparatus of the present embodiment, and a cross-section view of Section A-A of FIG. 2.
Figure 2:
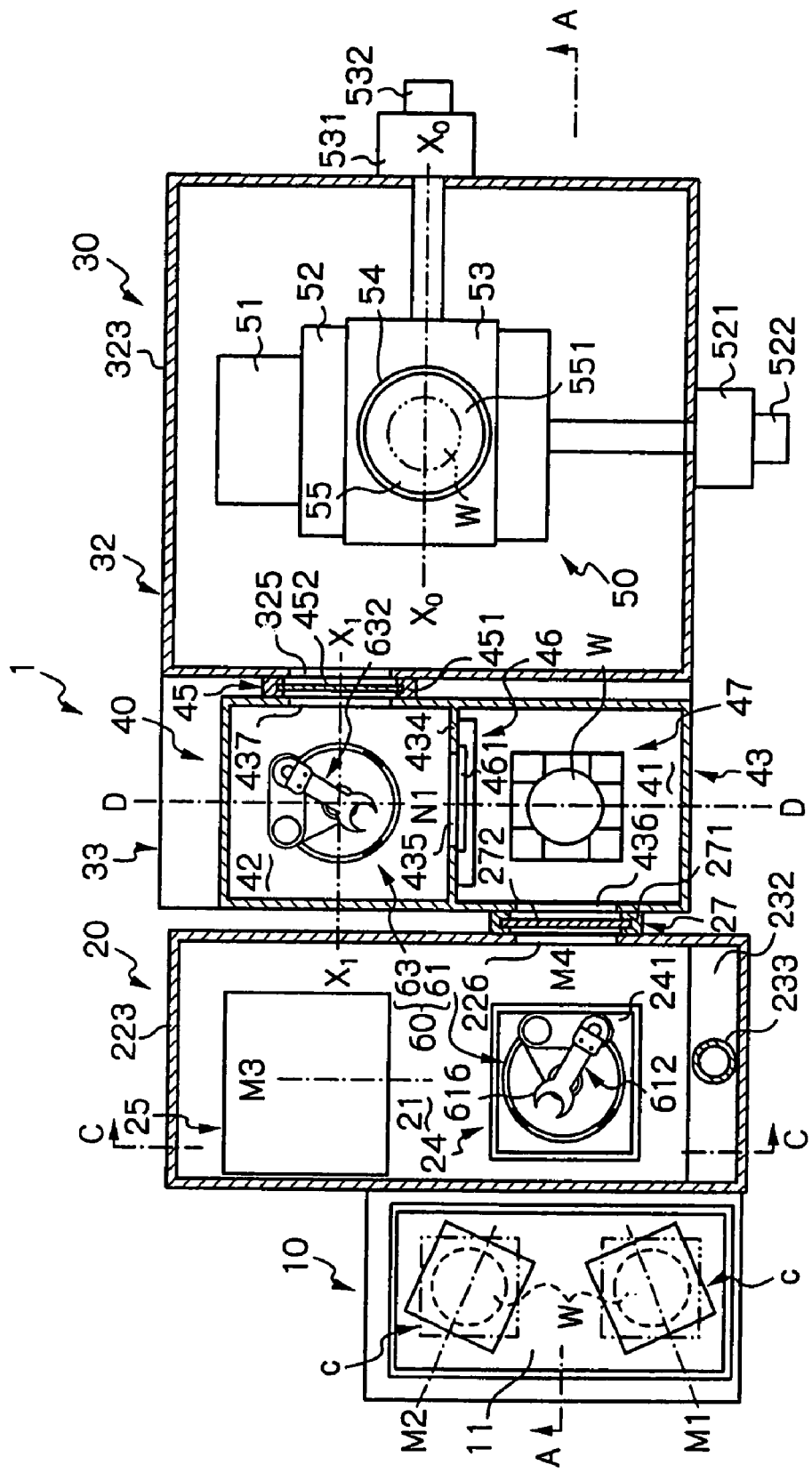
FIG. 2 is a plan view of the major components that make up the inspection apparatus of the present embodiment shown in FIG. 1, and a cross-section view of Section B-B of FIG. 1.

Shown in FIG. 1 and FIG. 2 are elevation and plan views, respectively, showing the major components that make up the semiconductor inspection apparatus 1 of the present embodiment.

The semiconductor inspection apparatus 1 of the present embodiment comprises the following major components, disposed in relative positions as shown in FIG. 1 and FIG. 2:

a cassette holder 10, for holding a cassette containing a plurality of wafers;

a minienvironment unit 20;

a main housing 30 that forms a working chamber;

a loader housing 40 placed between the minienvironment unit 20 and the main housing 30, that forms two loading chambers 40 and 41;

a loader 60 (61, 63) for taking a wafer from the cassette holder 10 and loading it onto a stage 50 placed in the main housing 30; and an electron optical apparatus 70 (a system for scanning an electron beam) installed in the main housing 30.

The semiconductor inspection apparatus 1 also comprises an optical microscope 871, which further comprises a precharge unit 81, placed in the main vacuum housing 30;

an electrical potential application device 83 (shown in FIG. 10), for applying an electrical potential to a wafer;

an electron beam calibration system 85 (shown in FIG. 10); and an alignment control system 87, for positioning a wafer on the stage 50.

The parts of the semiconductor inspection apparatus mentioned above also constitute vacuum pumps, vacuum valves, vacuum gages and vacuum lines (not shown in the drawing) for evacuating the electron optical system, detector, and working chamber (to be described later), in a prescribed sequence. A vacuum valve in each section is controlled to obtain the required level of vacuum therein. The vacuum is constantly monitored, and if an abnormal reading occurs, an interlock function activates emergency control of an isolation valve (not shown), to seal off the chamber from the evacuation system, etc., and maintain the required level of vacuum in the various parts of the system. For the vacuum pumps, a turbomolecular pump may be used for the main vacuum, and a Lutz-type dry pump may be used for rough pumping. The ambient pressure in the vicinity of a wafer on the stage (the part to be irradiated by an electron beam) must be between $10^{-3}$ and $10^{-6}$ Pa, but should preferably be between $10^{-4}$ and $10^{-6}$ Pa.

Cassette Holder

Figure 12:
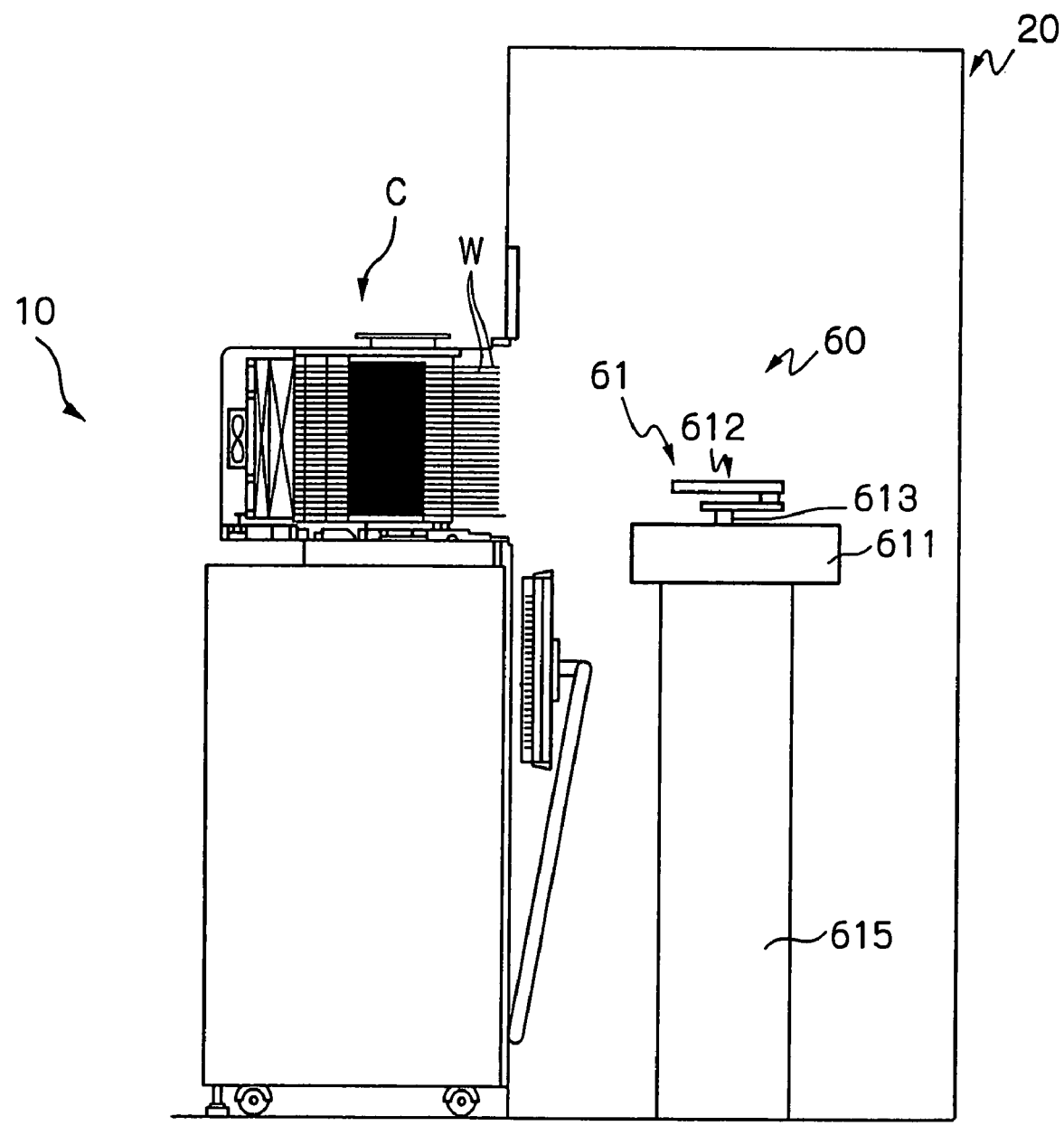
FIG. 12 is an enlarged cross-sectional side view of a cassette holder and minienvironment unit.

The cassette holder 10 is configured to hold a plurality of cassettes c (two, in this embodiment) each of which contains a plurality of wafers (e.g. 25) placed such as to lie flat, one over the other. The cassettes c may be closed cassettes such as the SMIF (Standard Mechanical InterFace), or FOUP (Front Opening Unified Pod) cassettes manufactured by Asyst Technologies. Either an automatically loaded or manually loaded cassette holder may be installed, at the option of the user. That is, if the cassettes are to be transported to the apparatus and loaded automatically by a robot, a closed cassette holder configured for automatic loading is installed; and if cassettes are to be loaded by hand, an open cassette holder designed for manual loading is installed. In this embodiment, the cassette holder 10, which is designed for automatic loading of cassettes c, comprises, for example, an elevator table 11, and an elevator mechanism 12 for raising and lowering the elevator table 11. A cassette c is first loaded on the elevator table in the position shown by dotted lines in FIG. 2. It is then automatically rotated by a first transporter unit 61 of the minienvironment unit (to be described later), to the position shown by solid lines, where it will be possible to remove wafers from it. It is then lowered on the elevator table 11 to the position marked by dotted lines in FIG. 1. Because the many wafers contained in the cassette c are placed to lie flat, one over the other, with separation therebetween, the arm of the first transporter unit is configured for being moved up and down, so that the transporter will be able to access any wafer in the cassette. FIG. 12 shows the relationship between the first transporter unit 61 and a loaded cassette c.

Substrates (wafers) to be inspected for defects are loaded in a cassette c. This inspection may be performed either during or after the wafer processing step of the semiconductor device manufacturing process. More specifically, the cassettes c could contain substrates (wafers) that have gone through processes such as etching and membrane-forming (including copper plating), CMP (chemical-mechanical polishing); planarization, or ion implantation; substrates (wafers) that have had device patterns formed on their surface; or wafers on which device patterns have not yet been formed.

Minienvironment Unit

Figure 3:
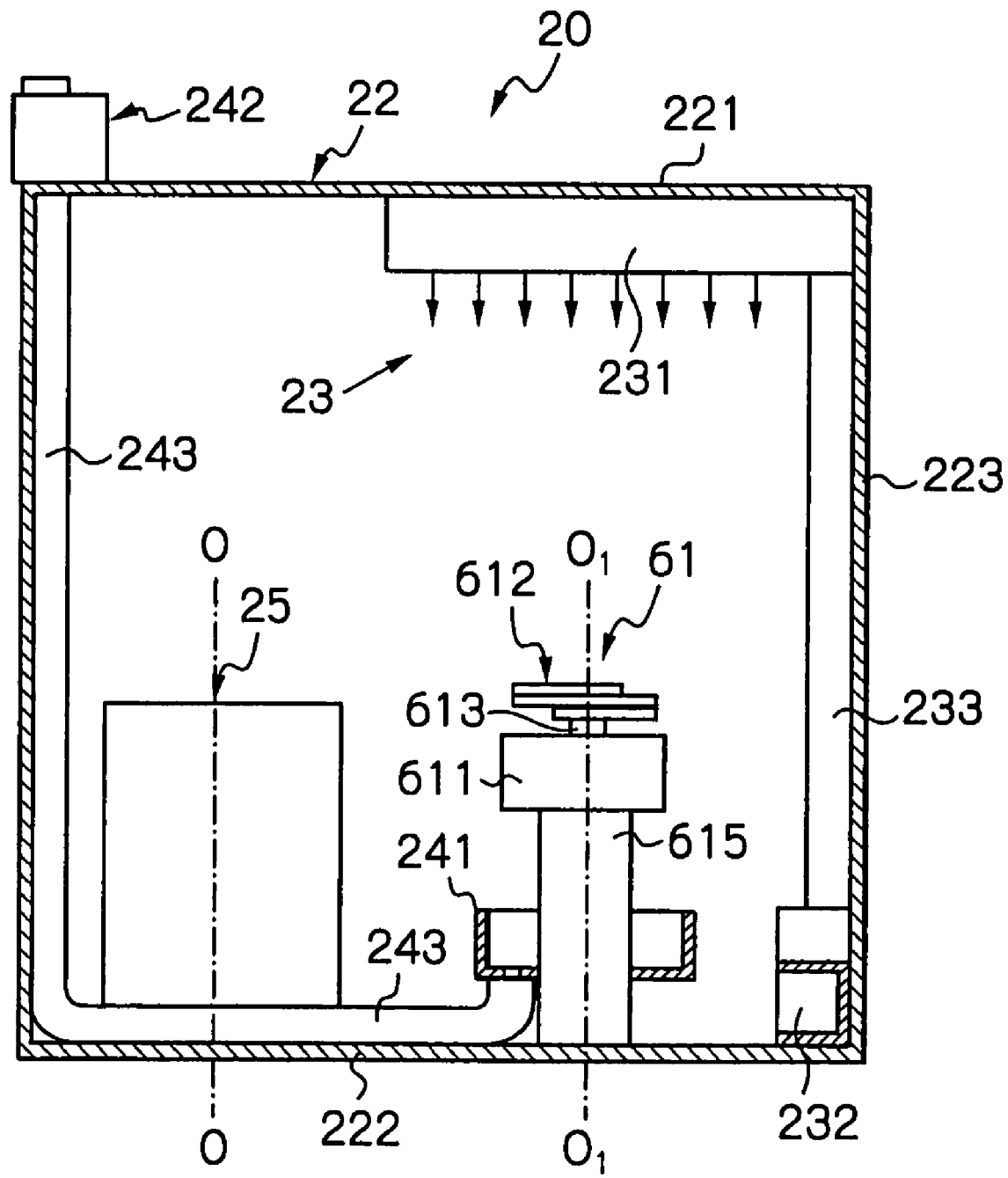
FIG. 3 is a cross-section view of Section C-C of FIG. 1, showing a minienvironment unit.

As shown in FIGS. 1-3, the minienvironment unit 20 comprises
- a housing 22 forming a minienvironment space 21 such that the atmosphere therein can be controlled;
- a gas circulation system 23 (231-233) for circulating a gas, such as clean air, through the minienvironment space 21 for controlling the atmosphere therein;
- a discharge system 24 for recovering and expelling a portion of the air being supplied into the minienvironment space 21; and
- a prealigner 25 for performing coarse positioning of a substrate (wafer) that has been placed in the minienvironment space 21 as a sample.

The housing 22 comprises a top plate 221, a floor plate 222, and four sidewalls 223, constructed to isolate the minienvironment space 21 from the outside. To control the atmosphere in the minienvironment space, the gas circulation system 23, as shown in FIG. 3, comprises
- a gas supply unit 231, installed within the minienvironment space on the top plate 221, for cleansing a gas (air, in this embodiment), and causing the cleansed gas to flow straight downward in a laminar flow, through one or more gas discharge outlets (not shown);
- a recovery duct 232, placed within the minienvironment space on the floor plate 222, for recovering air flowing downward toward the floor plate; and
- a conduit 233, connected between the recovery duct 232 and the gas supply unit 231, for returning recovered air to the gas supply unit 231.

In this embodiment, the gas supply unit 231 is configured so that about 20% of the air supply is air that has been brought in from outside of the housing 22 and cleansed. The percentage of the supplied air that is brought in from the outside, however, may be selected at the option of the user. The gas supply unit 231 is provided with either a HEPA (High Efficiency Particulate Air) filter, or an ULPA (Ultra-Low Penetration Air) filter, both of which are known filters, for producing the clean air. The possibility remains, however, that some dust could be introduced into the environment by the first transporter unit (to be described later), which is located within the minienvironment space 21. To keep dust from the transporter from being deposited on a wafer, the downward laminar flow (downflow) of clean air is supplied such that the main flow will pass over the wafer handling surfaces of the transporter unit. Therefore, the downflow discharge nozzles need not necessarily be placed at the top plate, as shown in the drawing; it is only necessary that they be located above the wafer handling surfaces of the transporter unit. Neither is it necessary for the air to flow through the entire minienvironment space. In some cases, cleanliness may be ensured by using an 'ion wind' for clean air. Sensors for monitoring air cleanliness may also be provided in the minienvironment space. This enables the system to be shut down promptly if air cleanliness is found to have been degraded As shown in FIG. 1, an access port 225 is formed in that portion of the sidewall 223 of the housing 22 that is adjacent to the cassette holder 10. A shutter apparatus of known design can be provided at the access port 225 to enable the access port to be closed. As for the flow rate of the laminar downflow created in the vicinity of the wafer, a flow rate of 0.3-0.4 meters per second, for example, would be adequate. The gas supply unit need not necessarily be placed inside the minienvironment space; it may be placed on the outside.

The discharge system 24 comprises
- a suction duct 241 placed at the lower part of the transporter unit, in a location below that of the aforementioned handling surface of the transporter unit;
- a blower 242 placed on the outside of the housing 22; and
- a conduit 243 connected between the suction duct 241 and the blower 242.

In this discharge system 24, gas flowing down around the transporter, which could contain dust from the transporter, is attracted to the suction duct 241 and discharged through the conduits 243 and 244, and the blower 242, to the outside of the housing 22. This discharge gas may be expelled into an external exhaust pipe (not shown) routed to the vicinity of the housing 22.

A prealigner 25 placed within the minienvironment space 21 is configured to optically or mechanically detect either an orientation flat, or one or more V-notches formed in the outer circumference of the wafer, and to pre-align the position of thereof, in rotation about a wafer axis line O-O, to an accuracy of approximately ±1 degree. The prealigner constitutes a portion of the mechanism of the present invention, as recited in the claims, for determining the coordinates of a sample, in which the function of the prealigner is to perform coarse alignment. The configuration of the prealigner, per se, is known; therefore, its configuration and operation will not be described.

A discharge system recovery duct (not shown) may also be provided near the bottom of the prealigner for expelling dust-bearing air from the prealigner to the outside.

Working Chamber

As shown in FIG. 1 and FIG. 2, a main housing 30, which forms the working chamber 31, has a housing main unit 32. This housing main unit 32 is supported by a housing support device 33, mounted on an anti-vibration device 37 (a vibration isolation device), which is placed on a pedestal frame 36. The housing support device 33 comprises a rectangular frame 331. The housing main unit 32 is placed on, and fastened to, the frame 331, and comprises a floor plate 321 mounted on the frame; a top plate 322; and sidewalls 323 that connect the top plate 322 to the floor plate 321, and surround the space therebetween on four sides, for isolating the working chamber 31 from the outside. Although in this embodiment, the floor plate 321 is made of a relatively thick steel plate to prevent its being distorted by the weight of equipment such as the stage, other types of construction may also be used. In this embodiment, the housing main unit and the housing support device 33 are assembled in a rigid structure. Vibrations from the floor on which the pedestal frame 36 is mounted are prevented from being transmitted to the rigid structure by the vibration isolation device 37. An access port 325, for passing wafers therethrough, is formed in the sidewall 323 of the housing main unit 32 that is adjacent to a loader housing (to be described later).

The vibration isolation device may be an active, or a passive device using air springs, magnetic bearings, etc. Since known constructions may be used in both cases, the construction and functions of the devices, per se, will not be described.

A vacuum atmosphere is maintained in the working chamber 31 by a vacuum apparatus (not shown) that is also of known design. A control unit 2 for controlling the operation of the entire system is installed under the pedestal frame 36. This control unit has a control system made up primarily of a main controller, a control controller, and a stage controller.

The main controller includes a man-machine interface through which an operator performs various operations (executes instructions and commands, inputs recipes, enters the 'start inspection' instruction, switches between automatic and manual inspection modes, inputs all necessary commands when in manual inspection mode, etc.). In addition, the main controller communicates with the plant host computer; controls the vacuum evacuation system; controls the movement and positioning of samples (wafers, etc.); and sends other commands to, and accepts data from, the control controller and stage controller. Also included are a stage vibration correction function that acquires image signals from the optical microscope and feeds-back a stage motion variance signal to the electron optical system for correction of image degradation; and an automatic focus correction function that senses changes in the Z direction (back and forth along the axis of a secondary optical system) of the sample observation position, and feeds-back this information to the electron optical system, for automatic focus correction. Exchange of feedback signals, etc. going to the electron optical system and coming from the stage are performed through the control controller and stage controller, respectively. The control controller primarily takes care of controlling the electron beam optical systems (by controlling high-precision power supplies for the electron gun, lenses, aligner, and ExB separator, etc.).

The control performed by the stage controller is primarily related to stage motion. It is capable of controlling precise (μm-order) travel in the X and Y directions of the stage within an error margin of approximately ±0.5 μm. With the present stage, rotation control (θ control) can be effected within an error margin of approximately ±0.3 second of rotation.

Loader Housing

The loader housing 40 shown in FIGS. 1, 2, and 4, comprises a housing main unit 43 that forms a first loading chamber 41 and a second loading chamber 42. The housing main unit 43 comprises a floor plate 431, a top plate 432, four surrounding sidewalls 443, and a partition 433 for partitioning the first loading chamber 41 from the second loading chamber 42, constructed such as to isolate both loading chambers from the outside. An opening (access port 435) is formed in the partition 434 for transferring wafers between the two loading chambers. Also, access ports 436 and 437 are formed in portions of the sidewalls 433 that are adjacent to the minienvironment unit and the main housing. The housing main unit 43 of this loader housing 40 is supported by mounting it on a frame 331 of a housing support structure 33. Here too, then, the configuration is such that floor vibrations will not reach the loader housing 40.

The access port 436 of the loader housing 40 is aligned with the access port 226 of the minienvironment housing 22, where a shutter 27 is provided for selectively preventing communication between the minienvironment space 21 and the first loading chamber 41. The shutter 27 comprises a seal 271 that surrounds the access ports 226 and 436 and is affixed in tight contact with the sidewall 433; a door 272 that works in cooperation with the seal 271 to prevent passage of air through the access ports; and a driver unit 273 for moving the door.

Also, the access port 437 of the loader housing 40 is aligned with the access port 325 of the housing main unit 32, where a shutter 45 is provided for selectively sealing off and preventing communication between the second loading chamber 42 and the working chamber 31. The shutter 45 comprises a seal 451 that surrounds the access ports 437 and 325, and is affixed in tight contact with the sidewalls 433 and 323; a door 452 that works in cooperation with the seal 451 to prevent passage of air through the access ports; and a driver unit 453 for moving the door. In addition, provided at the opening formed in the partition 434, is a shutter 46 with a door 461 that can be closed for selectively sealing off and preventing communication between the first and second loading chambers. These shutters are of known design, and their construction and operation will therefore not be described.

Also, different methods are used for supporting the housing 22 of the minienvironment unit 20 and the loader housing. Therefore, to prevent floor vibrations from being transmitted through the minienvironment unit to the loader housing 40 and main housing 30, airtight anti-vibration isolation damping device may be provided around the access port between the housing 22 and the loader housing 40.

Provided in the first loading chamber 41 is a wafer rack 47 for supporting a plurality of horizontal wafers (two, in this embodiment), with vertical separation therebetween. As shown in FIG. 5, the wafer rack 47 has a rectangular baseplate 471 with support posts 472 attached at the four corners thereof such as to stand erect and separate from each other. Formed in each of the support posts 472, at different heights thereof, are two support portions 473 and 474, for placing and holding the periphery of a wafer W thereon such that the wafer can be grasped by an arm of the first and a second transporter unit (to be described later).

The loading chambers 41 and 42 are constructed so that they can be atmosphere-controlled to maintain them in a high vacuum state ($10^{-5}$-$10^{-6}$ Pa) by vacuum systems of known design comprising vacuum pumps (not shown in the drawing). Wafer contamination can be effectively prevented by maintaining the first loading chamber 41 in a low vacuum state for use as a low vacuum chamber, and maintaining the second loading chamber 42 in a high vacuum state for use as a high vacuum chamber. This configuration enables a wafer in the loading chamber, that is next in line to be inspected for defects, to be moved into the working chamber without delay. The use of a loading chamber configuration such the above, in conjunction with multibeam principles of an electronic system to be described later, improve the throughput of the defect detecting process; and in addition, enable the vacuum in the vicinity of the electron source, where high vacuum storage conditions are required, to be maintained in the highest possible vacuum state.

The first and second loading chambers 41 and 42 are connected to a vacuum evacuation line, and to a vent line for performing purging with inert gas (e.g. dry pure nitrogen). (Neither line is shown in the drawing.) This enables the loading chamber interiors to be brought to atmospheric pressure by purging the chambers using inert gas (i.e., injecting inert gas into the chamber to prevent gases other than the inert gas, such as oxygen, from being adsorbed on surfaces). Apparatus of known configuration may be used for purging with inert gas, and the apparatus will therefore not be described in detail.

Moreover, in the inspection apparatus of the present invention, which uses an electron beam, lanthanum hexaboride ($LaB_6$) is typically used as the electron source for the electron optical system to be described later.

Once the $LaB_6$ has been heated to the high temperature state in which thermal emission of electrons occurs, any oxygen coming in contact with the electron source will greatly reduce its service life, and this must therefore be avoided to the maximum extent possible. This can be assured by using a controlled environment chamber such as described above at the stage from which wafers are transferred into the working chamber in which the electron optical system is installed.

The Stage

The stage 50 comprises
- a fixed table 51 mounted on the floor plate 321 of the main housing 30;
- a Y table 52 that moves over the fixed table in a Y direction (the direction perpendicular to the paper on which FIG. 1 is printed);
- an X table 53 that moves over the Y table in an X direction (the horizontal direction of FIG. 1);
- a turntable 54 that is rotatable on the X table; and
- a holder 55 placed on the turntable 54.

A wafer is releasably held on a wafer seat 551 of the holder 55. The holder may be of a known design for releasably securing a wafer either mechanically, or by using an electrostatic chuck. The stage 50 is configured to effect the precise positioning, with respect to an electron beam emitted by an electron optical system, of a wafer held on the wafer seat 551 by the holder. This positioning is performed in the X direction, the Y direction, a Z direction (vertically in FIG. 1), and a θ direction (in rotation about an axis line perpendicular to the plane of the wafer seat), by using servo motors, encoders, and various sensors (not shown), to operate a plurality of tables such as those mentioned above. The positioning in the Z direction may consist, for example, of making fine adjustments in the position in the Z-direction of the wafer seat on the holder. To do this, a position measurement device using a very-small-diameter laser (a laser interferometer ranging system using the principles of interferometry) can be used to sense a reference position of the wafer seat; and that position then controlled through a feedback circuit (not shown). Along with this, or instead of it, the position of the notch or orientation flat of the wafer can be measured, and the horizontal and rotational position of the wafer with respect to the electron beam controlled. To hold the amount of dust in the working chamber to the absolute minimum, the stage servo motors 521 and 531, and the encoders 522 and 532 are placed outside of the main housing 30.

It is also possible to standardize signals obtained by taking the X, Y, and rotation positions of the wafer with respect to the electron beam, and inputting them in advance to a signal detection circuit or image processing circuit (to be described later). In addition, the wafer chuck mechanism provided on this holder is configured such that a wafer chucking voltage can be applied to the electrodes of an electrostatic chuck to cause the wafer to be pressed against the holder at three points around the outer circumference of the wafer (preferably, at equally spaced points around the circumference), for positioning the wafer. The wafer chuck mechanism has two fixed positioning pins and one push-pressure-type clamp pin. The clamp pin is configured for automatic chucking and automatic release, and includes contact points for application of voltage.

Overall Configuration of the Loader

The loader 60 comprises a robotic first transporter unit 61, which is located in the housing 22 of the minienvironment unit 20; and a robotic second transporter unit 63, which is located in the second loading chamber 42.

The first transporter unit 61 has a multi-jointed arm 612 that is rotatable about the axis (line $O_1$-$O_1$ of FIG. 1) of a driver unit 611. The specific configuration of the multi-jointed arm is up to the user, but the arm used in this embodiment has three sections configured to be rotatable about each other. A first section of the arm 612 of the first transporter unit 61 (the section located nearest the driver unit 611) is installed on a shaft 613 that is rotated by a drive mechanism of known design (not shown in the drawing) in the driver unit 611. In addition to being rotatable about the axis $O_1$-$O_1$ by the shaft 613, the entire arm 612 can be extended and retracted (radially with respect to the axis $O_1$-$O_1$) through rotation of the individual sections relative to each other. Provided on the outer end of the third section of the arm 612 (the section most distant from the shaft 613 of the arm 612) is a grasping device 616 of known design (e.g., a mechanical or electrostatic chuck) for grasping and holding a wafer. The drive mechanism 611 is configured to be capable of being raised and lowered by an elevator mechanism 615 of known design.

This first transporter unit 61 extends its arm 612 in either a direction M1, or a direction M2, toward one of two cassettes c being held by the cassette holder, where its grasping device 616 grasps one of the wafers W contained in the cassette c (FIG. 12) and withdraws it. The arm then retracts (to the state shown in FIG. 12), rotates to where it can extend toward the prealigner 25 (direction M3), and stops. The arm then extends once more, and places the wafer W being held thereby on the prealigner 25. After prealignment of the wafer, the above operation is reversed: the arm removes the wafer W from the prealigner 25, rotates to where it can extend toward the second loading chamber 41 (direction M4), and stops. The arm then transfers the wafer to a wafer rack 47 in the second loading chamber 41. When the wafer is grasped mechanically, it is grasped near the periphery (a region extending 5 mm inward from the outer edge of wafer). The reason for this is that devices (circuit patterns) are formed everywhere on the wafer except in this peripheral region, and devices could be damaged, or defects created, by grasping the wafer anywhere but in this peripheral region.

The second transporter unit 63 will not be described in detail because it is basically the same as the first transporter unit 61, differing only in that it transports wafers between the wafer rack 47 and wafer loading surface of the stage.

In the loader 60 just described, the first and second transporter units (61 and 63) transport wafers from the cassette holder holding the cassette, to the stage 50 in the working chamber 31, or they do the same thing in reverse, with the wafers held substantially horizontal throughout. The arms of the transporter units move up and down only to withdraw wafers from, or insert them in, a cassette; load wafers in, or remove them from, the wafer rack; or to place wafers on, or remove them from, the stage. This makes it possible to handle even very large wafers (wafers 30 cm in diameter, for example) smoothly.

Transfer of Wafers from a Cassette to the Working Chamber by the Loader

Described next, is the sequence for transferring a wafer from a cassette c being held in the cassette holder, to the stage 50, located in the working chamber 31.

As mentioned earlier, a cassette holder 10 configured for manual loading can be used if the cassettes are to be set in it by hand, whereas if cassettes are to be set in the loader automatically, a holder designed for this type of operation may be used. In this embodiment, when a cassette c is set in place on the elevator table 11 of the cassette holder 10, the elevator table 11 is lowered by the elevator mechanism 12 until the cassette c is aligned with the access port 225.

Once the cassette is lined up with the access port 225, a cover provided on the cassette opens. In addition, a tubular cover may also be provided between the cassette c and the minienvironment access port 225, for shielding the cassette interior and the minienvironment space from the outside. If a shutter has been provided in the minienvironment unit 20 for opening and closing the access port 225, that shutter is also operated to open the access port 225.

At this time, the arm 612 of the first transporter unit 61 will be in the stopped state, facing in either the M1 or M2 direction (assume M1 for this description). Now, when the access port 225 opens, the arm comes forward, and with its forward end, withdraws one of the wafers contained in the cassette. In this embodiment, alignment of the vertical positions of the arm with the wafer to be removed from the cassette is performed by the driver unit 611 of the first transporter unit 61, which adjusts the vertical position of the arm 612. This could also be accomplished, however, through vertical motion of the cassette holder elevator table, or by moving both the elevator table and the arm. Once removal of the wafer by the arm 612 is complete, the arm is retracted, and the shutter (if there is one) is operated to close the access port. Next, the arm 612 is rotated about the $O_1$-$O_1$ axis to a position wherein it can be extended in the M3 direction. The arm then extends, and places the wafer (either riding on the end of the arm or being grasped by a chuck) on the prealigner 25. The prealigner properly positions the rotational orientation of the wafer (its orientation in rotation about a center axis perpendicular to the flat surface of the wafer) to within a prescribed number of degrees. When the positioning is complete and the wafer has been removed (on the end of the arm) from the prealigner 25, the first transporter unit 61 retracts the arm, and rotates to a position wherein the arm is extended in the M4 direction. The door 272 of the shutter 27 now operates to open the access ports 226 and 436, after which the arm 612 extends and places the wafer in the top or the bottom of the wafer rack 47, in the first loading chamber 41. Also, before the shutter 27 opens to transfer the wafer to the wafer rack 47, as described above, the opening 435 in the partition 434 is closed with an airtight seal by the door 461 of the shutter 46.

During the above wafer transport process, performed by the first transporter unit, a laminar flow (downflow) of clean air is supplied from the gas supply unit 231 provided in the upper portion of the minienvironment unit housing, to keep dust from being deposited on the top surface of the wafer during transport. A portion of the air around the periphery of the transporter unit (in this embodiment, about 20% of the air supplied by the supply unit—mainly dirty air) is expelled to the outside of the housing through the suction duct 241 of the discharge system 24. The remainder of the air is recovered and returned to the gas supply unit 231 through the recovery duct 232 provided at the floor of the housing.

When a wafer is placed in the wafer rack 47 in the first loading chamber 41 of the loader housing 40 by the first transporter unit 61, the shutter 27 closes, sealing off the inside of the loading chamber 41. Then, after the first loading chamber 41 is purged of air and filled with inert gas, the inert gas is also removed, creating a vacuum atmosphere in the loading chamber 41. For the vacuum in the first loading chamber 41, a low level vacuum will do. Once a given level of vacuum has been obtained in the first loading chamber 41, the shutter 46 is operated to open the access port 434 (which had previously been sealed shut by the door 461). At this point the second transporter unit 63 extends its arm 632, and with the grasping device at the end of the arm, takes one wafer from the wafer rack 47 (with the wafer either riding on the end of the arm or being grasped by a chuck). When the wafer has been completely withdrawn, the arm is retracted, and the shutter 46 again operates to seal off the access port 435 with the door 461. Note that before the shutter 46 opened, the arm 632 had been pre-positioned (facing in a direction N1) so that it could extend toward the wafer rack 47. Also, in the above description, before the shutter 46 was opened, the access ports 437 and 325 were closed by the door 452 of the shutter 45, to prevent communication between the second loading chamber 42 and the working chamber 31; and then the second loading chamber 42 was vacuum-evacuated.

After the shutter 46 closes the access port 435, the second loading chamber is again evacuated, this time to a higher level of vacuum than that in the first loading chamber. While this is taking place, the arm of the second transporter unit 61 is rotated to the position in which it can be extended toward the stage 50 in the working chamber 31. At the stage, in the working chamber 31, the Y table 52 is moved in the upward direction of FIG. 2, until it reaches a position in which the center axis $X_o$-$X_o$ of the Y table 53 is substantially aligned with the X axis line $X_1$-$X_1$ passing through the axis of rotation $O_2$-$O_2$ Of the second transporter unit 63. The X table 53 is moved as far as possible to the left in FIG. 2. The stage waits in this state.

When the second loading chamber reaches about the same level of vacuum as the working chamber, the door 452 of the shutter 45 operates to open the access ports 437 and 325. The arm then extends, causing the end of the arm, which is holding the wafer, to approach the stage in the working chamber 31, and it places the wafer on the wafer seat 551 of the stage 50. When this placement of the wafer is completed, the arm retracts, and the shutter 45 closes the access ports 437 and 325.

The above describes system operation in terms of transporting a wafer from a cassette c to the stage. Once the wafer has been loaded on the stage, and its processing completed, it is transported from the stage and returned to a cassette c in an operation that is the reverse of that described above. Also, because a plurality of wafers can be loaded in the wafer rack 47, while one wafer is being transferred between the wafer rack and the stage by the second transporter unit, another wafer can be transferred between the cassette and the wafer rack by the first transporter unit. This provides a more efficient inspection process.

Examples of Modified Versions of the Working Chamber

Figure 6A:
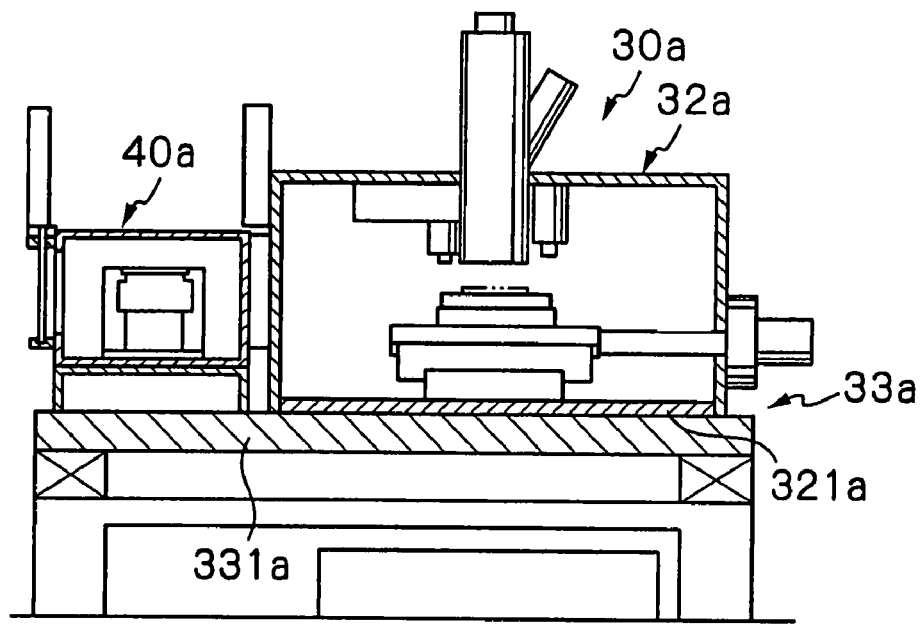
FIG. 6 (A) shows one variation of a method of supporting a wafer housing.
FIG. 6(B) shows another variation of a method of supporting a wafer housing.
Figure 6B:
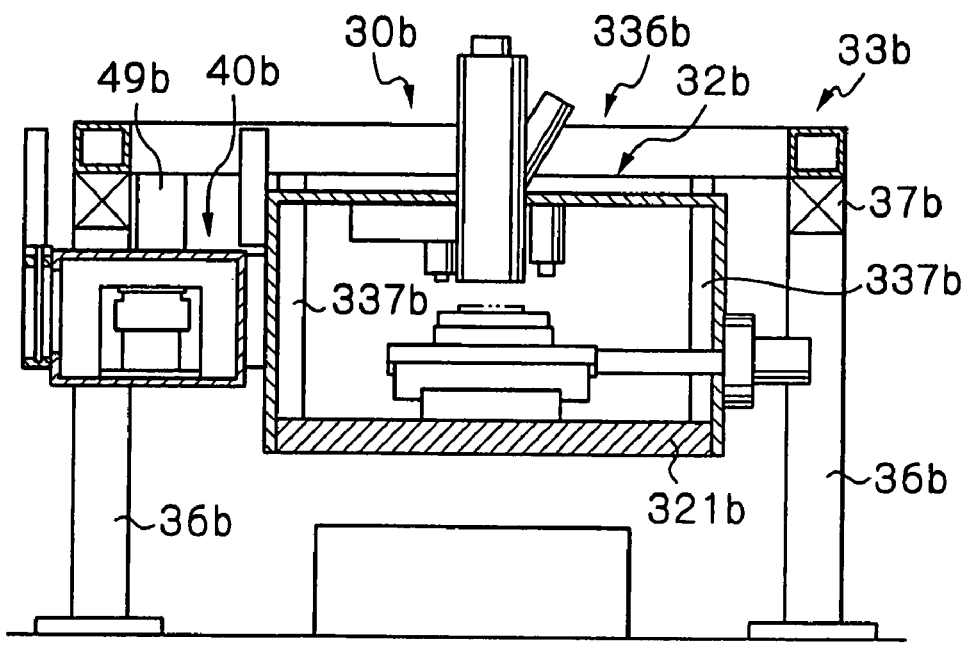

One example of a modification in terms of the way the main housing is supported is shown in FIG. 6. In the modified version shown in FIG. 6(A), a housing support device 33a is made of a thick rigid rectangular plate 331, on which a housing main unit 32a is mounted. Accordingly, the floor plate 321a of the housing main unit 32a is of thinner construction than the floor plate in the embodiment described above. In the modified version shown in FIG. 6(B), the housing main unit 32b and loader housing 40b are supported by suspending them from by the frame 336b of a housing support device 33b. A plurality of vertical frames 337b (fastened to the frame 336b) are fastened to the housing main unit 32b, with the bottoms of these vertical frames fastened to the four corners of a floor plate 321b of the housing main unit 32b, such that the sidewalls and top plate are supported by the floor plate. Placed between the frame 336b and a pedestal frame 36b is an vibration isolation device 37b. The loader housing 40 is also suspended by a hanger 49b fastened to the frame 336. Because the modified housing main unit 32b of FIG. 6(B) is supported by suspension, the main housing and the various equipment in contains (as a whole) has a lower center of gravity. The method of supporting the main housing and loader housing included in the above modification example is designed to prevent vibrations from being transmitted from the factory floor to the main housing or loader housing.

In another example of a modified version not shown in the drawings, only the housing main unit of the main housing is supported from below by a housing support device, the loader housing being supported above the floor by the same method as that used to support the adjacent minienvironment unit.

In yet another example of a modified version not shown in the drawings, only the housing main unit of the main housing is supported by suspending it from a frame, the loader housing being supported above the floor by the same method as that used to support the adjacent minienvironment unit.

Electron Optical System

Figure 7:
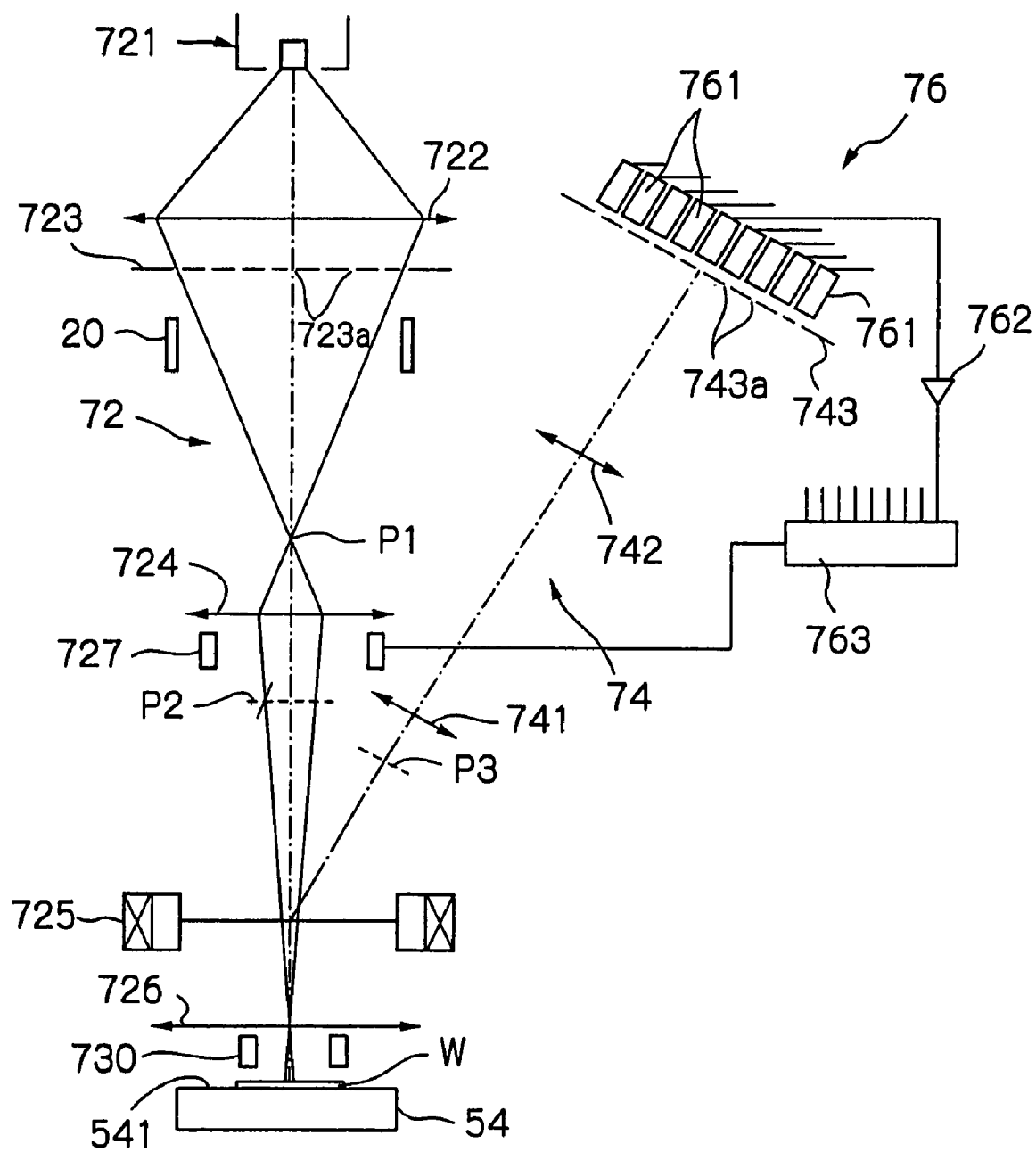
FIG. 7 is a schematic diagram of the electron optical system of the inspection apparatus of FIG. 1.
Figure 8:
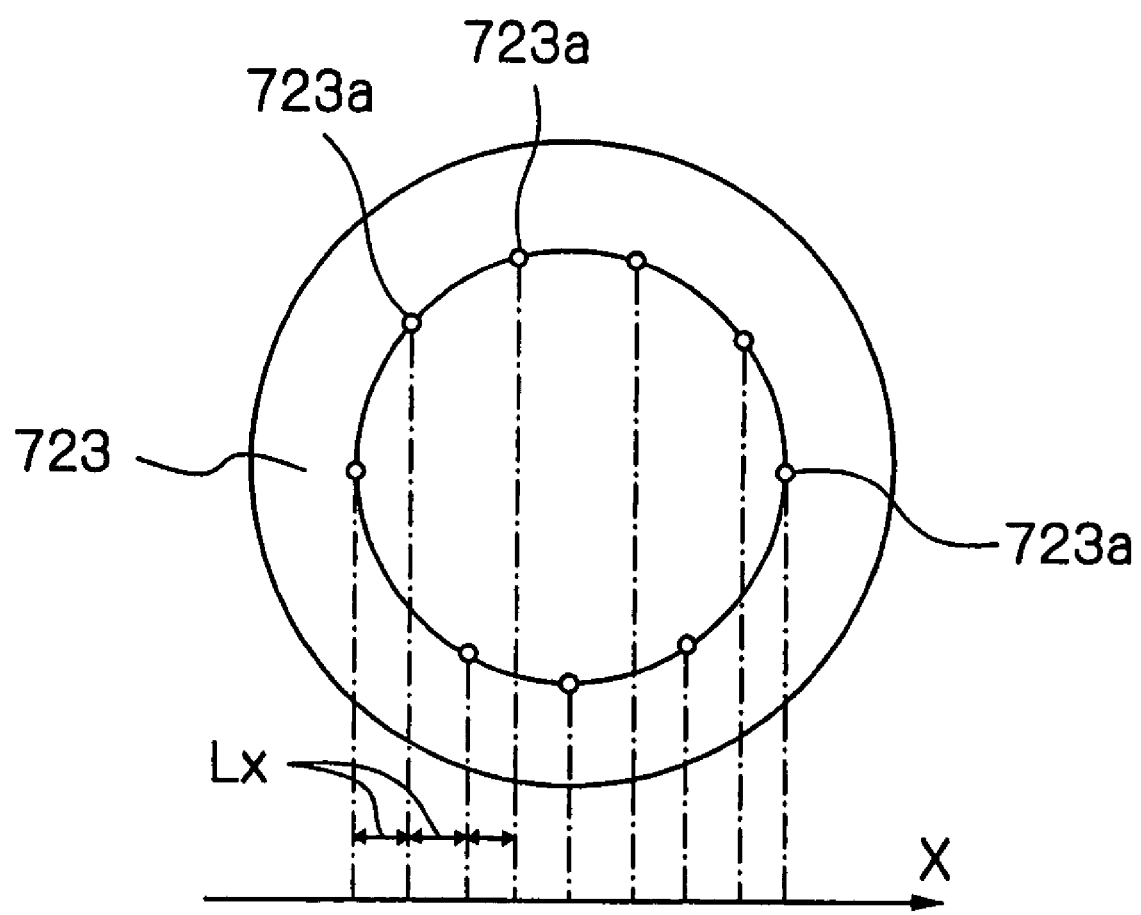
FIG. 8 is a drawing to show the positional relationships of the apertures of a multi-aperture plate used in the primary optical system of the electron optical system of FIG. 7.

An electron optical apparatus 70 comprises a column 71 installed in the housing main unit 32. Provided in the column 71, as shown schematically in FIGS. 7 and 8, are a primary electron optical system (hereinafter, 'primary optical system') 72, a secondary electron optical system (hereinafter, 'secondary optical system') 74, and a detector 76. The primary optical system 72 is the optical system that irradiates the surface of a wafer W (the sample) with electron beams. This primary optical system 72 comprises an electron gun 721, for emitting an electron beam;
an electrostatic condenser lens 722, for converging the primary electron beam emitted by the electron gun 721;
a multi-aperture plate 723 placed below the condenser lens 722 and having multiple apertures formed therein, for forming the primary electron beam into multiple primary electron beamlets;
an electrostatic demagnification lens 724, for demagnifying the primary electron beams;
a Wien filter (ExB separator) 725; and
an objective lens 726;

all of which, as shown in FIG. 7, are arranged in the above listed sequence with the electron gun 721 at the top, such that the optical axis of the primary electron beam emitted by the electron gun is perpendicular to the surface of a sample S (e.g., a wafer W).

The electron gun uses a thermionic electron beam source.

The emitter material is $LaB_6$, but another material may be used as long as it has a high melting point (a low vapor pressure at high temperatures) and low work function. There are two ways to obtain multiple beams: one is to draw one electron beam from one emitter (an emitter with one tip), and the other is to form multiple tips on an emitter and draw multiple beams from them. In this embodiment of the present invention, primarily the latter of these is used. An example of another type of electron beam source that could also be used is the thermal field emission electron beam. In a thermionic electron beam source, emission of electrons is obtained by heating the emitter material. In a thermal field emission electron beam source, a strong electric field is applied to the emitter material to obtain electron emission, and the electron beam emitter is also heated, to stabilize emission.

Figure 14:
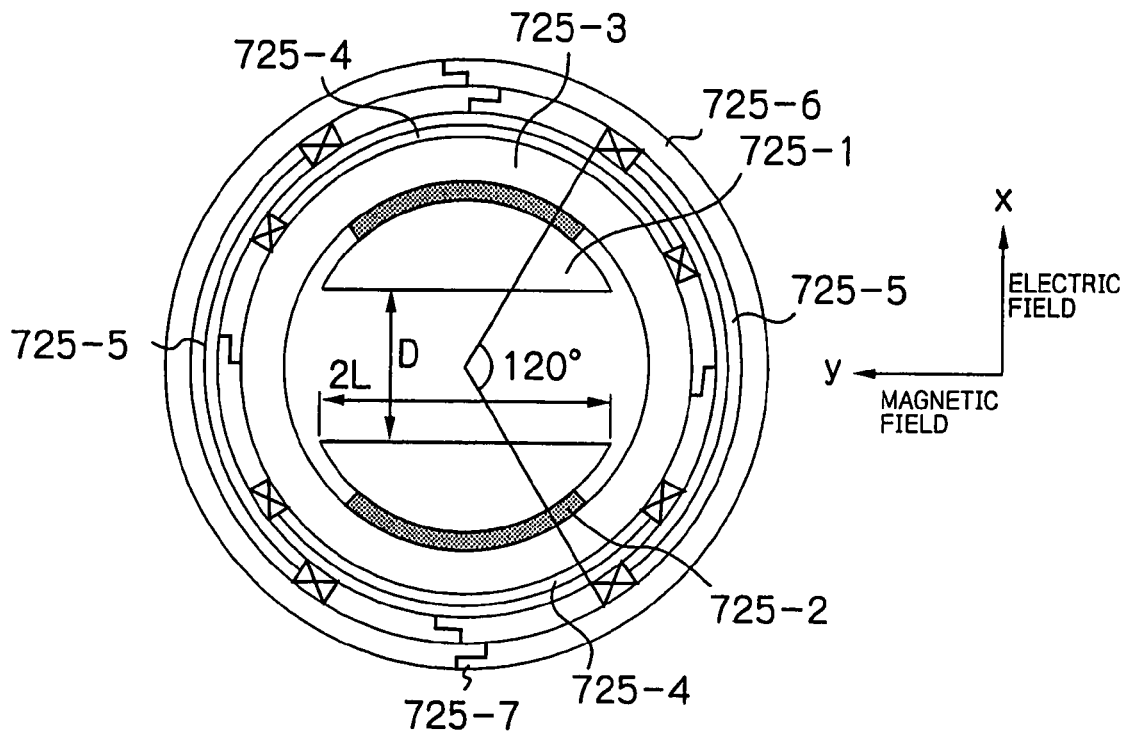
FIG. 14 is a cross-sectional plan view of a ExB separator.

An ExB separator, as shown in FIG. 14, is made up of an electrostatic and an electromagnetic deflectors. The electrostatic deflector comprises a pair of poles (electrostatic deflection poles) 725-1 in a vacuum chamber, for generating an electric field in the x-axis direction. These electrostatic deflection poles 725-1 are mounted on a vacuum bulkhead 725-3, with insulating spacers 725-2 therebetween. The distance D (the distance between these poles) is set to be less than 2 L (the length of the electrostatic deflection poles 725-1 in the y-axis direction). Establishing this relationship will provide a fairly large range over which the strength of the electric field about the z-axis (optical axis) is uniform. Ideally, however, a larger range of uniform electrical field strength will be obtained by setting D<L.

That is, since the electric field strength cannot be not uniform over a range extending from the ends of the poles to D/2, the region over which it will be substantially uniform is a central region extending to 2 L-D, excluding the regions nearest the ends, where the field strength will be non-uniform. Thus a relationship 2 L>D must be established for a region of uniform electric field strength to even exist, and a larger region can be obtained by setting L>D.

An electromagnetic deflector is provided outside of the vacuum bulkhead 725-3 for generating a magnetic field in the y-axis direction. This electromagnetic deflector comprises electromagnetic coils 725-4 and 725-5, for generating magnetic fields in the x- and y-axis directions, respectively. The magnetic field in the y-axis direction could be created by the coil 725-5 only, but the coil 725-4 is added to improve the orthogonality between the electric and magnetic fields. That is, the orthogonality between electric and magnetic fields is improved because the component of the magnetic field generating by the coil 725-4 in the -x axis direction cancels the component of the magnetic field created by the coil 725-5 in the +x axis direction.

Figure 15:
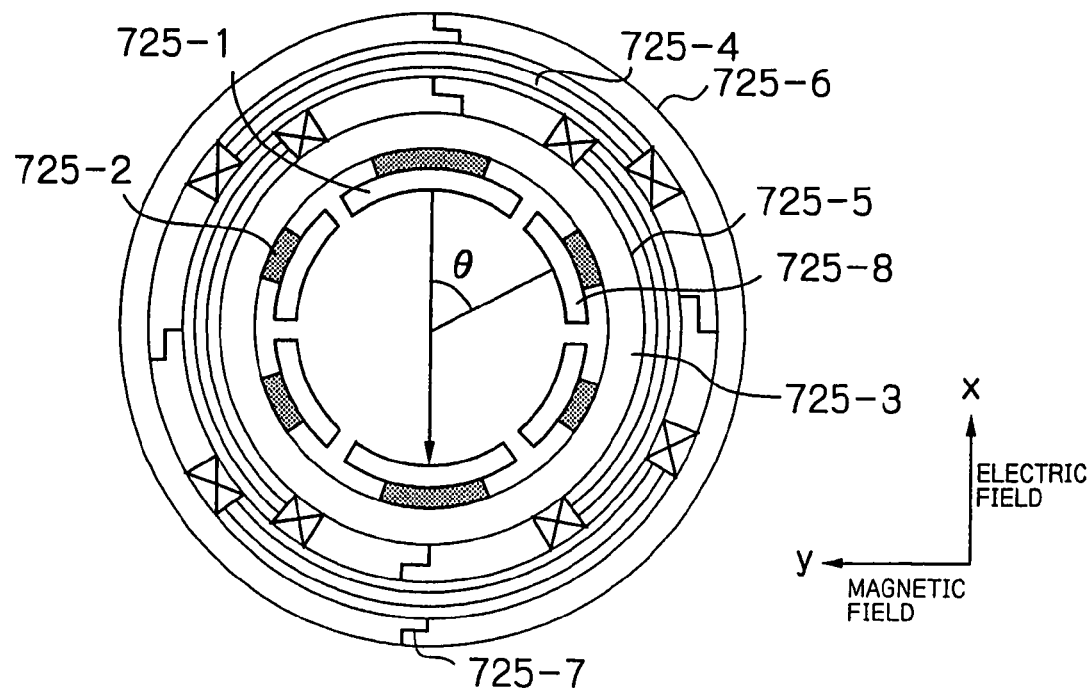
FIG. 15 is a cross-sectional side view of a ExB separator.

FIG. 15 shows another embodiment of the ExB separator of the present invention. This embodiment differs from the one shown in FIG. 14 in that it has six electrostatic deflection poles 725-1. Applied to each of these electrostatic deflection poles 725-1 is a voltage proportional to $K \cdot \cos \theta_i$ (i=0, 1, 2, 3, 4, 5), where k is a constant, and $\theta_i$ is the angle formed between a line from the center of the pole piece to the optical axis (z axis) and the direction of the electric field (x-axis direction in this case). The value of the angle $\theta_i$ is arbitrary.

In the embodiment shown in FIG. 15, as well, coils 725-4 and 725-5 are provided for generating magnetic fields in the x-axis and y-axis directions, and for improving orthogonality, the same as in the first embodiment. This embodiment, however, provides a larger region of uniform electric field strength than can be obtained in the embodiment of FIG. 14.

In the ExB separator shown in FIG. 14 and FIG. 15, the coils for generating magnetic fields are formed as saddle-type coils. Toroidal coils, however, could also be used.

To eliminate the effects of field curvature aberrations in the demagnification lens 724 and the objective lens 726, a plurality of apertures 723a (nine, in this embodiment) formed in the multi-aperture plate 723, are arranged in a circle having the optical axis at its center, spaced so as to lie at equal intervals Lx in the X direction of the projected image, as shown in FIG. 8.

The secondary optical system 74 comprises magnification lenses 741 and 742 (a two-stage electrostatic lens) through which secondary electrons separated from the primary optical system by the ExB separator 725 are passed; and a detector multi-aperture plate 743. The apertures 743a formed in the detector multi-aperture plate 743 correspond one-for-one with the apertures 723a formed in multi-aperture plate 723 of the primary optical system.

The detector 76 comprises a plurality of detector elements 761 (nine, in this embodiment), each of which is placed in close proximity to the corresponding apertures 743a of the multi-aperture plate 743 of the secondary optical system 74; and an image processor 763 that is electrically connected through A/D converters 762 to the detector elements 761 of the detector 76.

Electron Optical System Operation

Next, the operation of an electron optical apparatus 70 configured as described above will be described.

The primary electron beam emitted from the electron gun 721 is converged by the condenser lens 722 of the primary optical system 72 to form a crossover at a point P1. This primary electron beam that is converged by the condenser lens 722 is formed by the plurality of apertures 723a of the multi-aperture plate into a plurality of primary electron beamlets, which are then demagnified by the demagnification lens 724 to be projected at a position P2. After first being focused at the position P2, the beamlets are again focused by the objective lens 726 on the surface of a wafer W.

Figure 16:
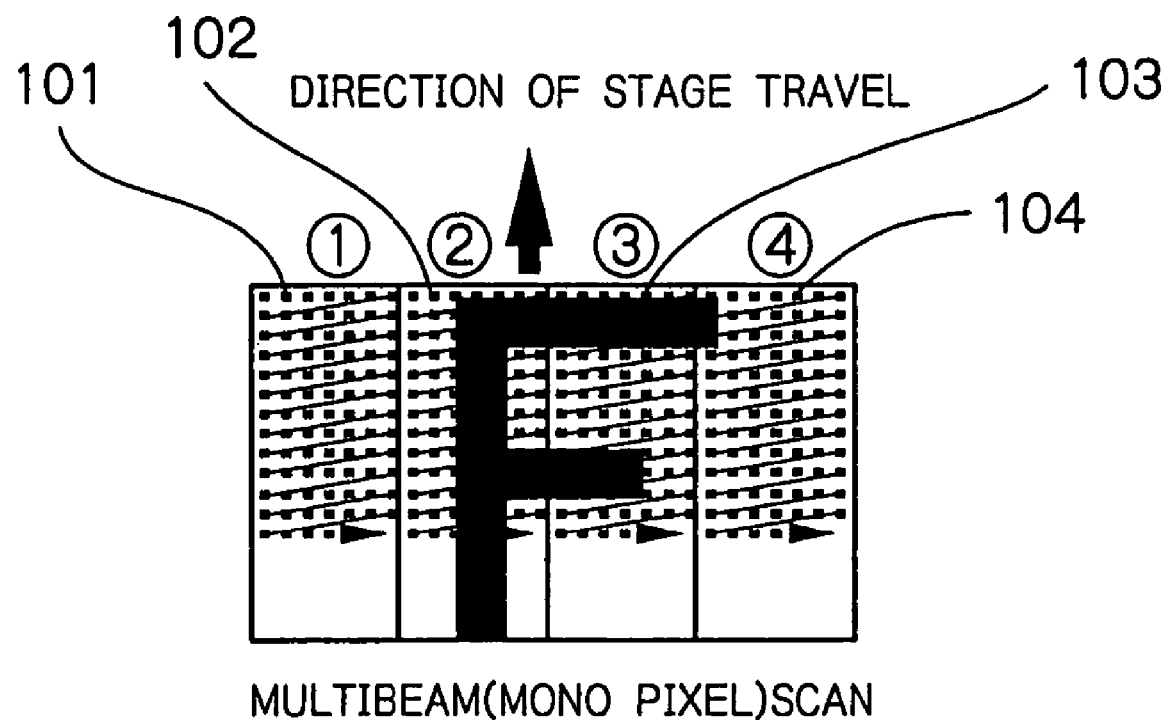
FIG. 16 shows how a sample (wafer) is scanned during irradiation by multiple primary beamlets.

The deflector 727 placed between the demagnification lens 724 and the objective lens 726 deflects the primary electron beamlets for scanning them over the surface of the wafer W. FIG. 16 shows an example of one way in which the surface of the wafer W may be scanned by the primary electron beam. In this example four equally spaced primary electron beamlets 101-104 scan from left to right in the drawing. When the beamlets reach the right ends of their scans, the stage on which the wafer is being supported moves upward (in the drawing) by a prescribed step distance, as the beamlets return to the left end of the scan. This process then repeats until the required region of the wafer has been scanned.

Thus the sample S (wafer W) is irradiated at a plurality of points by the plurality of primary electron beamlets (nine, in this embodiment), causing secondary electrons to be emitted from these points. These secondary electrons are attracted to, and tightly converged by, the electric field of the objective lens 726; and then are deflected by the ExB separator 725 to be injected into the secondary optical system 74. The image formed by the secondary electrons comes into focus at a position P3, which is nearer the deflector 725 than is the position P2. Although the energy of the primary electron beam at the wafer is 500 eV, the energy of secondary electrons is only a few eV.

Each of the secondary electron images focused at the position P3 is magnified by the two magnification lenses 741 and 742, is again focused at the corresponding aperture 743a of the multi-aperture detector plate 743, and passes through the aperture to be detected by the detector element 761 placed at its corresponding aperture 743a. The detector element 761 converts the detected electron beamlet to an electrical signal representative of the intensity of the secondary beamlet. Electrical signals thus converted are output from each of the detector elements 761, after which they are converted to a digital signal by an A/D converter 762, and input to the image processor 763. The image processor 763 converts its digital signal inputs to image data. The scan signal used to deflect the primary electron beam is also supplied to the image processor 763 to be used, along with its digital input, to form an image of the surface of the wafer. In a comparator (not shown), this image is compared to a standard pattern input to a settings unit (not shown) beforehand, thus to detect (evaluate) pattern defects in the inspected wafer.

In addition, the line width of a pattern formed on a wafer W can be measured by performing a registration operation to move the pattern to be measured near the optical axis of the primary optical system, performing a line scan to obtain a line width signal, and properly calibrating the signal.

Also, with respect to the image, it should be noted that although the above description covered the case in which the obtaining of only secondary electron images was selected, images can be obtained not only for secondary electrons, but also for scattered electrons, and back-scattered electrons as well.

Also, in a system such as described above, in which primary electron beamlets passed through the apertures of the multi-aperture plate 723 of the primary optical system are brought to a focus at the surface of the wafer W, and secondary electrons emitted from the wafer are imaged on the detector element 761, special emphasis must be placed on minimizing the effects of the following three types of aberration occurring in the primary optical system: coma, axial chromatic aberration, and field astigmatism.

Also, the separation between the primary beamlets is related to the secondary optical system in that crosstalk between beamlets can be eliminated by separating the primary beamlets from each other by a distance greater than the aberration of the secondary optical system.

Also, during operation of the electron optical system, evaporation of sample material, etc. takes place. Over time, this results in the accumulation of contamination material on various optical elements such as deflectors, the effects of which can degrade system operation. This accumulated contamination must therefore be removed on a periodic basis. This can be accomplished by using electrodes in the vicinity of areas having accumulations of contamination material, in a vacuum, to excite a plasma of hydrogen, oxygen or fluorine, thus to oxidize and remove only the contamination material.

Electron Optical System for Precharge Unit

As shown in FIG. 1, a precharge unit 81 is installed in the working chamber 31, near to the column 71 of the electron optical apparatus 70. The present inspection apparatus is a type of system in which inspection of a device pattern, etc., formed on the surface of a substrate, i.e., a wafer (the sample) is performed by scanning the wafer with electron beam irradiation, and using data from the secondary electrons produced by this electron beam irradiation to obtain information about the wafer surface.

During this process, depending on factors such as the material of the wafer and the energy of the irradiating electrons, 'charge-up' (accumulation of electrical charge on the surface of the wafer) can occur. In addition, the charge can be strong in some parts of the surface, and weak in others. When such charge variations exist over the surface, they produce variations in the secondary electron signal, and accurate information can no longer be obtained. Therefore, in the present embodiment, a precharge unit 81, comprising a charged particle irradiator 811, is provided, to prevent such charge variations. In order to avoid charge variations, before the prescribed location to be inspected on a wafer is irradiated with electrons, it is first irradiated with charged particles from the charged particle irradiator 811. The wafer is then checked for charge-up beforehand by forming an image of the wafer surface and evaluating that image, and the operation of the precharge unit 81 is then based on this evaluation.

Such charge variations can also be removed by blurring the primary electron beam in the precharge unit.

Precharging can also be used to inspect for electrical defect in a wafer inspection sample. Assume, for example, that a location originally intended to be electrically insulating has for some reason become conductive. In a comparison, the charge in the defective location will appear different from that in a location that is a properly insulated portion. Therefore, when the wafer is irradiated with the primary electron beam and inspected based on secondary electrons, it will be possible to check for electrical defects on the wafer.

Electrical Potential Application System for the Sample

The yield at which secondary electrons are emitted from a wafer is influenced by the electrical potential of the wafer. Based on this fact, the electrical potential application system for sample 83 (FIG. 9) controls the emission of secondary electrons by applying a potential of ± a few volts to the mount on which the stage carrying the wafer is installed. This electrical potential application system also serves to reduce the landing energy possessed by the irradiating electrons, putting the energy of the irradiating electrons at the wafer at roughly 100-500 eV.

Figure 9:
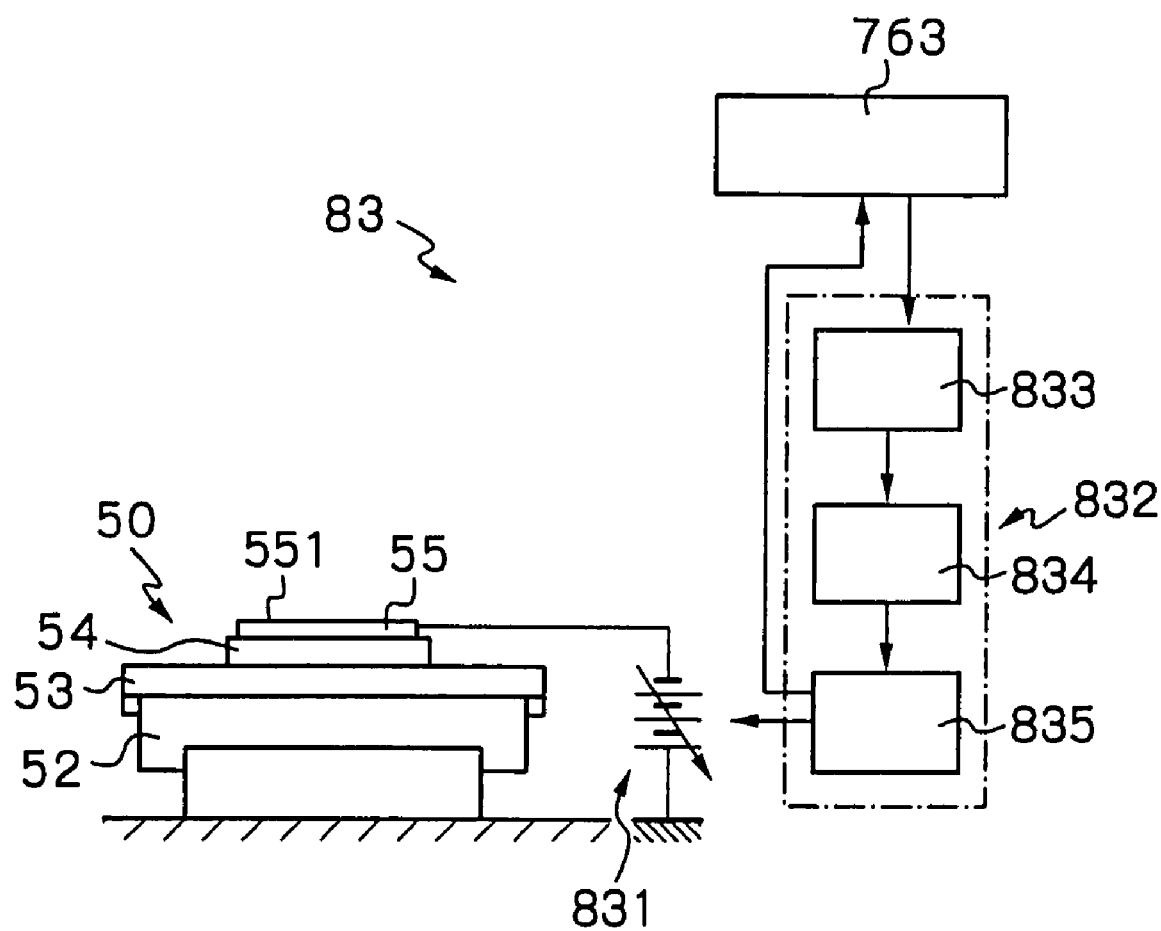
FIG. 9 shows an electrical potential application system.

As shown in FIG. 9, the electrical potential application system 83 comprises a voltage application device 831 electrically connected to a mounting surface 541 of the stage 50, and a charge-up investigation and voltage determination system (hereinafter, 'investigation and determination system') 832. The investigation and determination system 832 comprises a computer monitor 833 electrically connected to the image processor 763 of the detector 76 of the electron optical apparatus 70; an operator 834 for monitoring the monitor 833; and a CPU 835 that is controlled by the operator 834. The CPU 835 supplies signals to the above voltage application device 831 and to the deflector 727.

The above electrical potential application system is designed to find a potential at which it would not be likely for the sample (wafer) to charge up, and to apply that potential.

Calibration Mechanism for the Electron Optical System

Figure 10A:
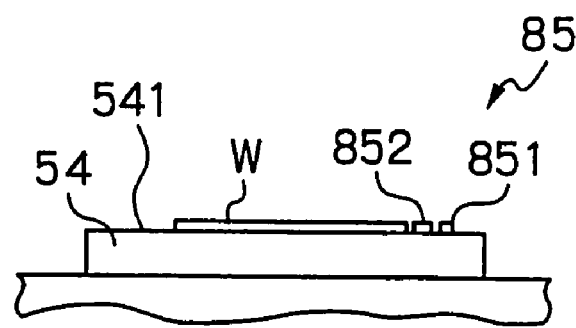
FIG. 10(A) shows a side view of an electron beam calibration mechanism.
Figure 10B:
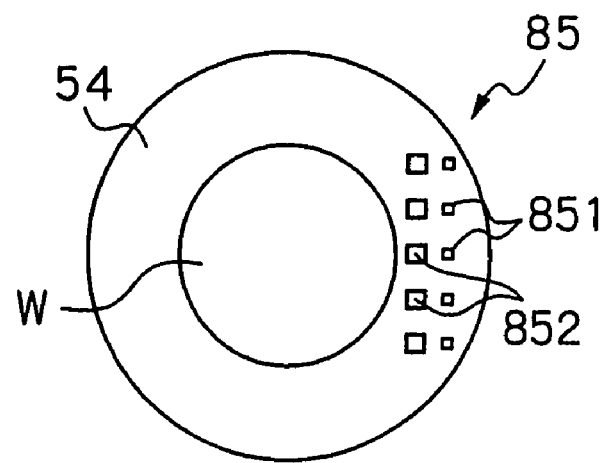
FIG. 10(B) shows a plan view of the mechanism of FIG. 10(A).

As shown in FIG. 10, a calibration mechanism 85 comprises a plurality of Faraday cups 851 and a plurality of Faraday cups 852 placed at a plurality of locations at the side of the wafer-mounting surface 541, on the aforementioned turntable, for measurement of beam current. The Faraday cups 851 are for fine beams (approximately $\phi 2$ µm), and the Faraday cups 852 are for broad beams (approximately $\phi 30$ µm). The fine-beam Faraday cups 851 are used to measure beam profiles while rotating the turntable in steps. Total beam current is measured by the broad-beam Faraday cups 852. The Faraday cups 851 and 852 are placed such that their top surfaces are at the same level (height) as the top surface of a wafer W placed on the wafer-mounting surface 541. In this configuration, the primary electron beam emitted by the electron gun is always monitored. The reason for doing this is that the electron gun cannot always emit a constant beam, and variations in the amount of emission can therefore occur during use.

Alignment Control System

The alignment control system 87 is a system for positioning a wafer W with respect to the electron optical axis using the stage 50. It is designed to control operations such as rough alignment of the wafer in wide field observation using the optical microscope 871 (a less accurate measurement than one by the electron optical system); high magnification alignment using the electron optical systems of the electron optical apparatus 70; focus adjustment; setting of the inspection area; and pattern alignment. The reason for using an optical microscope to inspect the wafer at low magnification when performing wafer alignment is that it provides a convenient way of detecting the electron beam alignment marks for automatic inspection of the wafer pattern with the electron beam in narrow field observations of the pattern.

Figure 11:
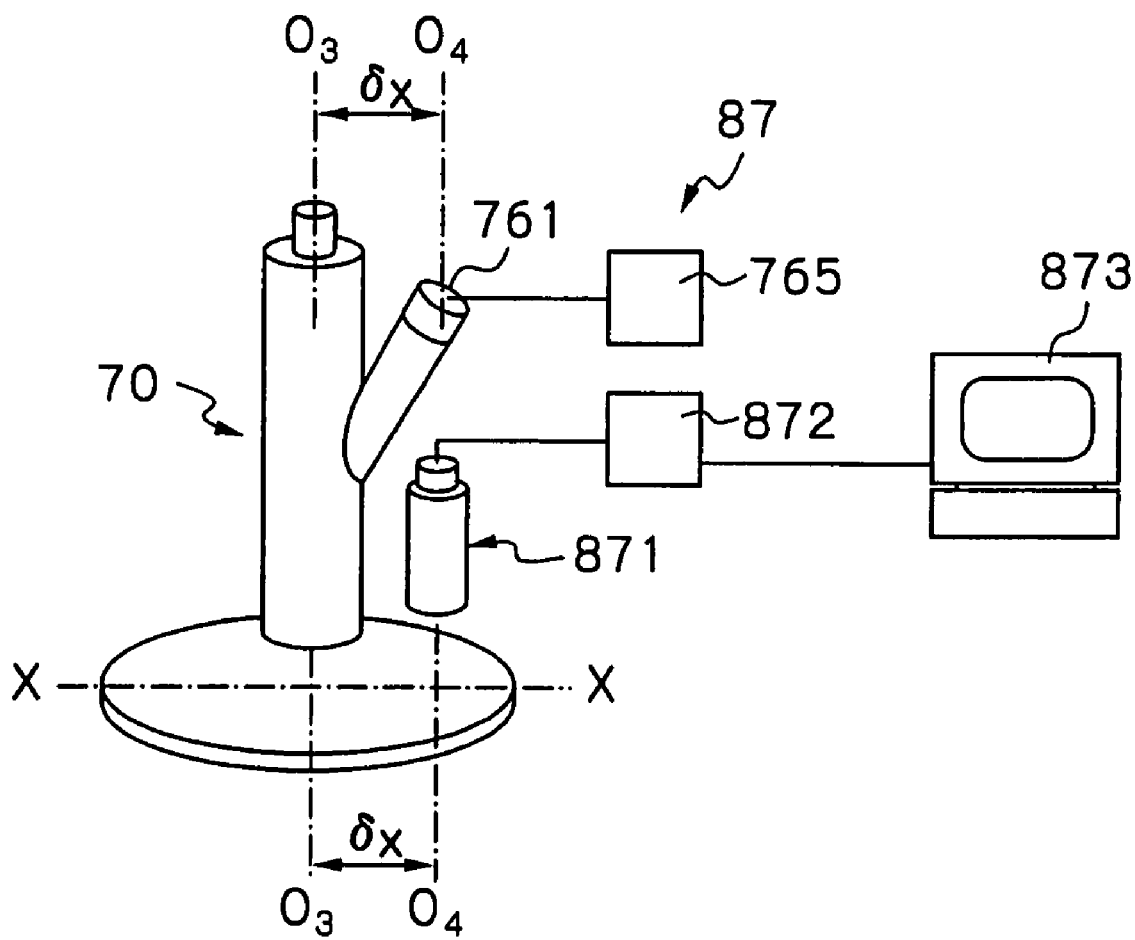
FIG. 11 is a simplified diagram of an alignment control system for wafers.

The optical microscope 871 is provided in the housing (it may be provided such as to be movable within the housing). A light source (not shown) for operating the microscope is also provided within the housing. The alignment control system 87 is shown schematically in FIG. 11. To observe the point to be observed (on the wafer), at low magnification, that point is moved into the field of the optical microscope by moving the x-stage 53 of the stage 50 in the X direction. A wide-field observation of the wafer is then performed using the optical microscope 871. The location to be observed on the wafer is found and displayed on a computer monitor 873 through a CCD 872, and the observation position is roughly determined. During this procedure, the magnification of the microscope may be changed between low and high magnification.

Next, the stage 50 is moved a distance corresponding to $\delta x$, the separation between the optical axis of the electronic optical apparatus 70 and the optical axis of the microscope 871, to thus move the observation point (on the wafer), determined in advance using the microscope, into the field of the electron optical apparatus. When so doing, since $\delta x$, the distance between the axis $O_3$-$O_3$ (the electron optical axis) and the axis $O_4$-$O_4$ (the optical axis of the microscope 871) is known in advance, the observation point can be moved to the observed position by moving by an amount equal to the value of $\delta x$. Also, although in this example, it was assumed that the positions of both axes are displaced only in the X axis direction, they may actually be displaced in both the X and Y axis directions. After the point to be observed has been moved to the observed position of the electron optical apparatus, an SEM photograph of the observed point is taken at high magnification by the electron optical system. The SEM photograph is then stored in memory and displayed on the monitor 765.

After the point on the wafer to be observed has been displayed at high magnification on the monitor by the electron optical system, the displacement of the position of the wafer in rotation about the center of rotation of the turntable 54 of the stage 50 (i.e. $\delta \theta$, the displacement of the wafer in rotation about the electron optical system optical axis $O_3$-$O_3$), is detected by a known method. The displacement in the X and Y directions of the position of a prescribed pattern with respect to the electron optical system is also detected. Then, wafer alignment is performed by controlling movement of the wafer stage 50 based on these detected values, along with separately obtained data on alignment marks provided on the wafer, and data on the wafer pattern shape.

Inspection Sequence (Summary)

Figure 13:
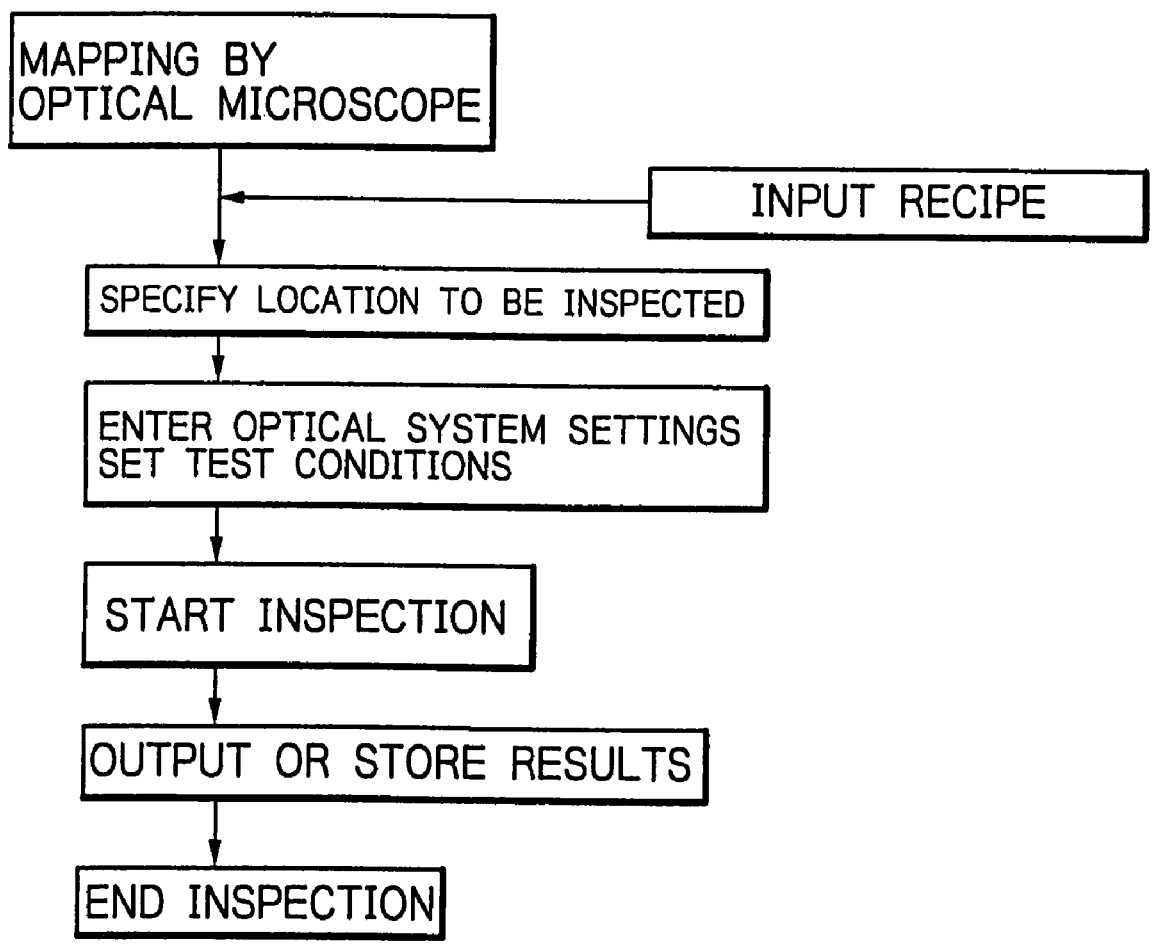
FIG. 13 shows steps for performing inspections using the electron optical system.

FIG. 13 summarizes the procedure for inspecting wafers (samples) using the electron optical apparatus. First, using the optical microscope, the positions of dies are checked, and heights of locations are detected and stored, as required. Next, recipe data is entered into the system for the wafer type being inspected (information on the last process completed, whether the wafer size is 20 cm or 30 cm, etc.), the locations to be inspected are specified, and optical system settings and inspection conditions are entered. Normally, defect inspection is performed in real time while acquiring images. Cell-to-cell comparisons, die comparisons, etc. are performed by a high speed data processing system provided with appropriate algorithms. Inspection results are output to a CRT display and/or stored in memory. Defects can also be automatically classified in real time as to type, i.e., particle defects, shape abnormalities (pattern defects), or electrical defects, which can be further classified in terms of defect size, and 'killer defects' (serious defects that will prevent the chip from being used). Electrical defect detection can be accomplished through detection of electrical potential contrast abnormalities. For example, when a location having poor continuity is irradiated with an electron beam (of approximately 500 eV) it will normally take on a positive charge, increasing its contrast, and thus making it distinguishable from good locations. The electron beam irradiation system used for this purpose may be a separate system, other than the one used for inspection. Such a separate system would be a low electrical potential energy electron beam irradiation system for enhancing the contrast due to difference in potential. Before irradiating the sample region with the inspection electron beam, it is irradiated with the low electrical potential energy electron beam. If a projection lithography technique capable of producing the required positive charge is used to irradiate the sample with the inspection electron beam itself, however, depending on the application, a special system for generating a low electrical potential electron beam may not be required.

Defects can also be detected from the differences in contrast produced when a potential that is negative or positive with respect to a reference potential is applied to a sample such as a wafer. The differences in contrast in this case are caused by differences in the ease with which currents flow through device elements in the forward and reverse directions. This technique can also be used with line width and alignment accuracy measurement systems.

Effects of the Inspection Apparatus in the Above Embodiment

In particular, the following effects can be brought to fruition through application of the inspection apparatus of the above embodiment:

a. High throughput processing of inspection samples can be achieved through effective functional combination of the various equipment components that make up the multi-beam inspection apparatus.
b. While samples are being inspected, monitoring for the presence of dust in controlled environment space can be conducted via sensors provided within the environment.
c. A precharge unit provided in the apparatus substantially reduces the influence of electrical charge on inspections, even on insulated wafers.

Maintenance of Vacuum in the Working Chamber (Stage Improvement 1)

When ultra-high-precision positioning of the stage that supports the wafer (the inspection sample in the apparatus of the present invention) is required, the structure for supporting the stage uses static pressure bearings that support the stage without touching it. During operation, high pressure gas is expelled from the bearings. To keep this high pressure gas from entering directly into the vacuum chamber, a differential pumping mechanism for expelling the gas is formed adjacent to the bearing, to maintain the proper vacuum in the vacuum chamber.

Figure 17A:
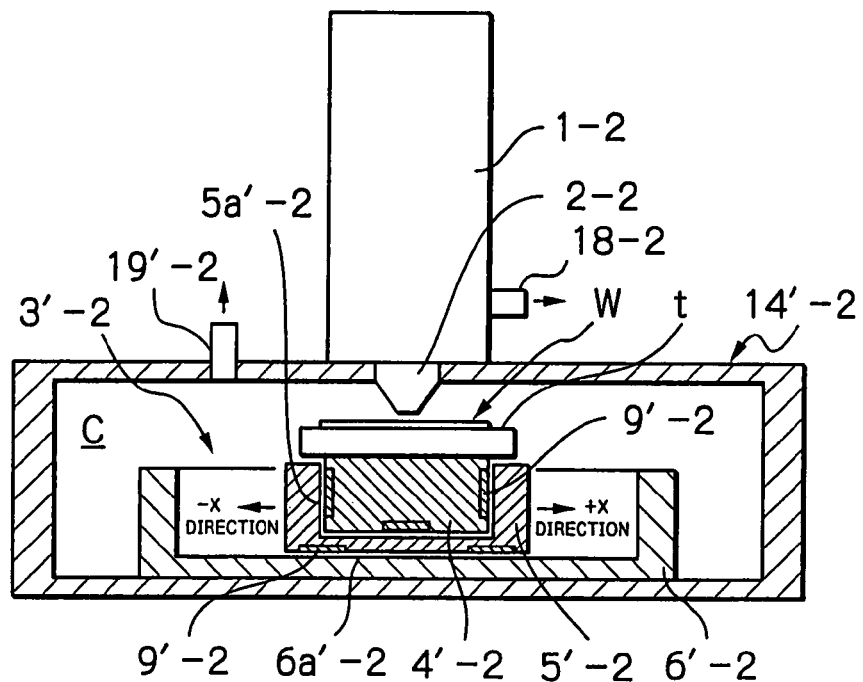
FIG. 17(A) shows a front view of the vacuum chamber and XY stage of a prior electron beam inspection apparatus.

An example of a prior stage for such a system is shown in FIGS. 17(A) and (B). In the configuration shown in the drawing, an electron beam irradiator 2-2 (the output end of a column 1-2) of an electron beam inspection apparatus that generates an electron beam for irradiating a sample is mounted on a housing 14'-2 that forms a vacuum chamber C. To form a vacuum in the column, the column is evacuated through a vacuum line 18-2. The vacuum chamber C is evacuated through a vacuum line 19'-2. The electron beam irradiates a sample (wafer) by passing through the output end 2-2 of the column 1-2, under which the sample is placed.

Figure 17B:
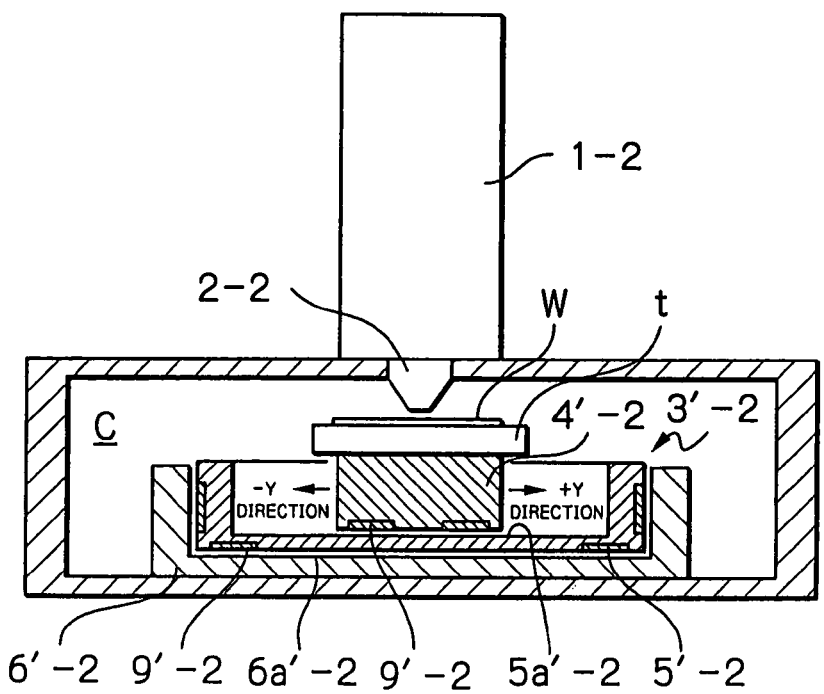
FIG. 17(B) shows a side view of the vacuum chamber and XY stage of FIG. 17.
Figure 18:
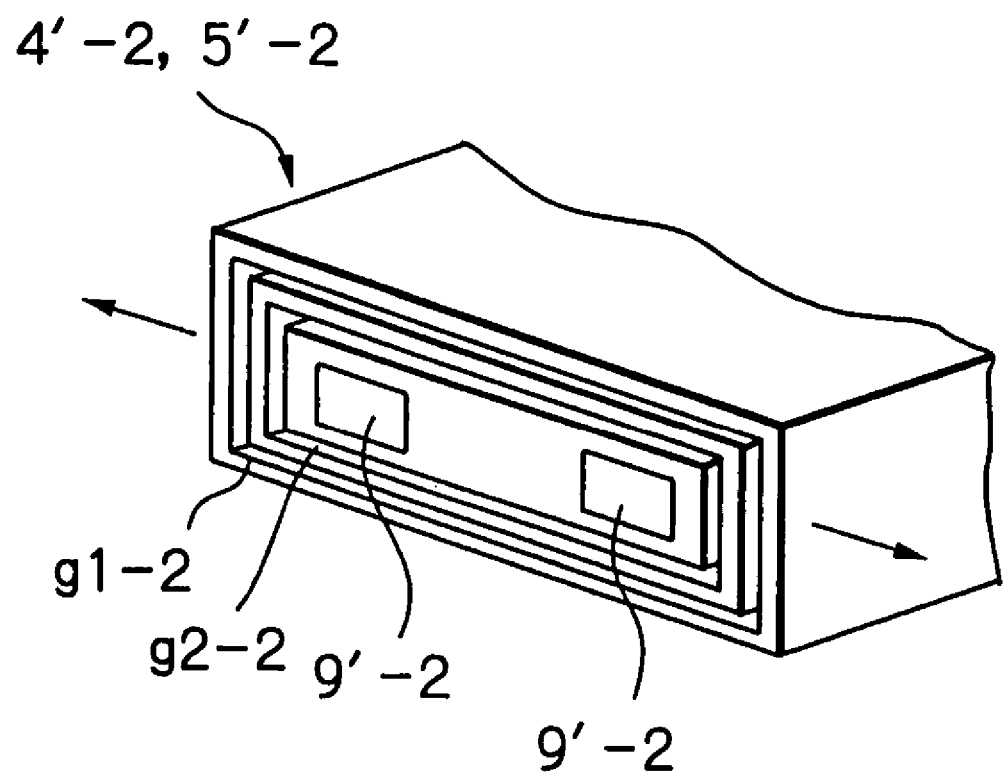
FIG. 18 shows a differential discharge device used in the XY stage of FIG. 17.

The wafer W is releasably retained on a sample table t by a known method, and the sample table t is installed on the top surface of a Y-movable section 4'-2 of an XY stage (hereinafter 'stage') 3'-2. Provided on this Y-movable section 4'-2, facing a guide surface 5a'-2 (comprising the left and right sides and the bottom in FIG. 17(A)) of an X-movable section 5'-2 of the stage 3-2, are a plurality of static pressure bearings 9'-2, for moving the stage in the Y direction (left and right in FIG. 17(B)) through the action of the static pressure bearings 9'-2, as an extremely narrow gap is maintained between the movable section and the guide surface. A differential gas discharge mechanism is also provided around the static pressure bearings, to prevent high pressure gas being supplied to the static pressure bearings from leaking into the vacuum chamber C. This mechanism is shown in FIG. 18. Double grooves (the grooves g1-2 and g2-2) are formed around the static pressure bearings 9-2. These grooves are constantly being evacuated by a vacuum pump, via a vacuum line (not shown). This configuration enables the Y-movable section 4'-2 to be non-contactingly supported in a vacuum such as to be movable in the Y direction. These double grooves g1-2 and g2-2 are formed in the surface in which the static pressure bearing 9'-2 of the movable section 4'-2 is provided, such as to surround the static pressure bearings.

As is evident from FIGS. 17(A) and (B), the shape of the X-movable section 5'-2, in which this Y-movable section 4'-2 is provided, is that of an open top box. Exactly the same kind of static pressure bearings and grooves are also provided in this X-movable section 5'-2, thus enabling it to be non-contactingly supported in a stage mount 6'-2 so as to be movable in the X direction.

By combining the movements of the Y-movable section 4'-2 and X-movable section 5'-2, the sample W can be moved to any location (horizontally) relative to the output end of the column (electron beam irradiator) 2-2, for irradiating the desired location on the sample with the electron beam.

A problem with the above system, in which static pressure bearings are combined with a differential pumping mechanism, however, is that the differential pumping mechanism makes the stage larger and more complex than static pressure bearing-type stages used at atmosphere pressure. The stages are also more expensive, and less reliable.

Accordingly, the present invention eliminates the differential discharge mechanism of the XY stage to provide a simple configuration while still providing an electron beam inspection apparatus in which the vacuum in the working chamber is maintained at the required level.

Electron Beam Inspection Apparatus With an Improved Stage

Following is a description of an embodiment of the electron beam inspection apparatus of the present invention with an improved stage. Items in the drawing of the improved stage that are the same as items of the prior stage shown in FIG. 17(A) and FIG. 17(B) will retain the same reference numbers in this description. Also, for the purposes of this specification, the term 'vacuum' shall be understood to mean vacuum as it is commonly understood in the art.

Figure 19:
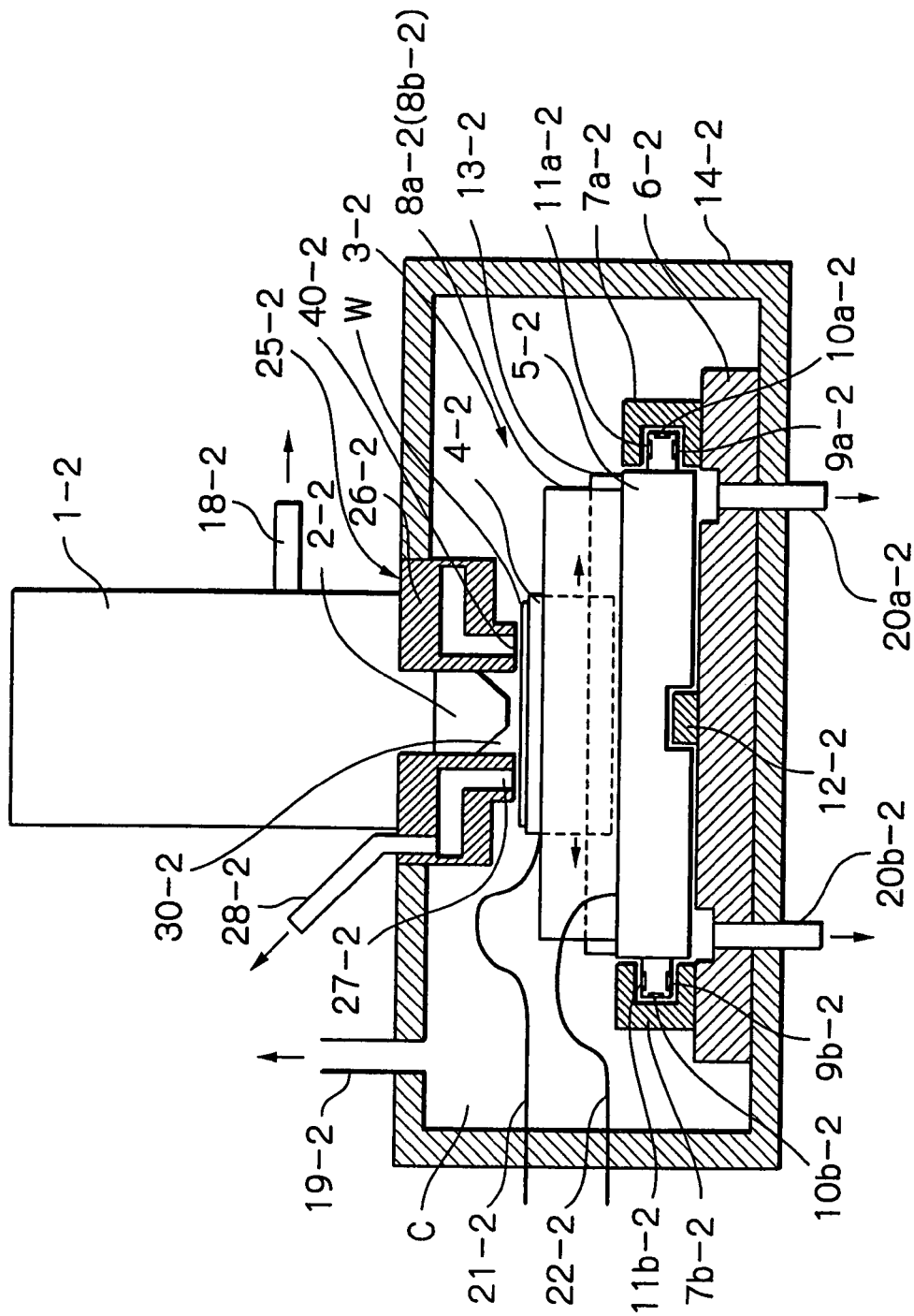
FIG. 19 shows the vacuum chamber and XY stage in one embodiment of the electron beam inspection apparatus of the present invention.

A first embodiment of the electron beam inspection apparatus with an improved stage is shown in FIG. 19. An electron beam irradiator 2-2 (the output end of a column 1-2) that emits an electron beam toward a sample is installed in a housing 14-2 that forms a vacuum chamber C. An XY stage 3-2 is configured such that a sample W placed on a table that is movable in the X-direction (the left-right direction of FIG. 19) can be placed directly under the column 1-2. The sample W can then be positioned by the high-precision XY stage 3-2 such as to cause the electron beam to accurately irradiate any desired location on the surface of the sample.

A mounting plate 6-2 of the XY stage 3-2 is attached to the floor plate of a housing 14-2, and a Y table 5-2 that is movable in the Y direction (the direction perpendicular to the page of FIG. 19) is placed on the mounting plate 6-2. A pair of Y-direction guides 7a-2 and 7b-2 having channels formed in one side thereof, are placed on the mounting plate 6-2 such that their channels face the Y table. Also, formed on the left and right side surfaces of the Y table 5-2 (left and right as shown in FIG. 19), are protrusions that protrude into the channels of the Y-direction guides 7b-2 and 7a-2. The channels extend nearly the entire length of the Y-direction guides. Provided on the top, bottom, and side surfaces of the protrusions that protrude into the channels, are static pressure bearings 11a-2, 9a-2, 11b-2, and 9b-2, of known construction. Through this configuration, the Y table 5-2 is non-contactingly supported in the Y-direction guides 7a-2 and 7b-2 by high pressure gas blown through these static pressure bearings, such that it can move smoothly back and forth in the Y direction. A linear motor 12-2 of known construction is placed between the mounting plate 6-2 and the Y table 5-2 for driving the Y-table in the Y direction. High pressure gas is supplied to the Y table by a flexible high pressure gas supply line 22-2, and high pressure gas is supplied through a gas duct (not shown) formed within the Y table to the static pressure bearings 9a-2 through 11a-2 and 9b-2 through 11b-2. High pressure gas supplied to the static pressure bearings is blown into gaps (of a few microns to a few tens of microns) formed between guide surfaces opposite the Y-direction guides, to provide accurate positioning of the Y table with respect to the guide surfaces, in the Z direction (up and down in FIG. 19) and X direction.

Placed on the Y table, such as to be movable in the X direction (left and right in FIG. 19), is an X table 4-2. A pair of X-direction guides 8a-2 and 8b-2 (only 8a-2 is shown), are provided on the Y table 5-2, with the X table 4-2 therebetween. These X-direction guides are of the same construction as the Y-direction guides 7a-2 and 7b-2 for the Y table. In these X-direction guides as well, channels are formed on the sides of the guides that face the X table. Also, protrusions that protrude into the channels are formed on the sides of the X table that face the X-direction guides. The channels extend nearly the entire length of the X-direction guides. Provided on the top, bottom, and side surfaces of the protrusions on the X-table 4-2 that protrude into the channels, are the same kind of static pressure bearings 11a-2, 9a-2, 10a-2, 11b-2, 9b-2, and 10b-2 (not shown). A linear motor 13-2 of known construction is placed between the X table 4-2 and the Y table 5-2 for driving the X-table in the X direction. High pressure gas is supplied to the X table 4-2 by a flexible high pressure gas supply line 21-2, for supplying high pressure gas to the static pressure bearings. This high pressure gas is blown from the static pressure bearings toward the guide surfaces of the X-direction guides for non-contactingly supporting the X table 4-2 and accurately positioning it with respect to the Y-direction guides. The vacuum chamber C is evacuated by vacuum pumps of known construction, connected to the vacuum lines 19-2, 20a-2, and 20b-2. The vacuum lines 20a-2 and 20b-2 are passed through mounting plate 6-2 so that their input ends (the ends inside the vacuum chamber) open at the surface of the mounting plate near locations where high pressure gas is expelled from the XY stage 3-2. This almost completely prevents pressure fluctuations from developing within the vacuum chamber due to the high pressure gas being blown out of the static pressure bearings.

A differential discharge mechanism 25-2 is provided around (encircling) the electron beam irradiator 2-2 (output end) of the column 1-2. This discharge mechanism ensures that the pressure within an electron beam irradiation space 30-2 will remain sufficiently low, even if the pressure within the vacuum chamber C is high. An annular member 26-2 of this differential discharge mechanism 25-2 is installed around (encircling) the electron beam irradiator 2-2. This annular member is positioned relative to the housing 14-2 such as to form an ultra-fine gap 40-2 (a gap of from a few microns to a few tens of microns) between the bottom surface of the annular member (the surface at the sample W end) and the sample. An annular channel 27-2 formed in the bottom surface of the annular member is connected to a vacuum pump (not shown) through a exhaust tube 28-2. High-pressure gas from the ultra-fine gap 40-2 is expelled through the annular channel 27-2 and the discharge outlet 28-2, as will be any gas molecules from the vacuum chamber C that penetrate into the space 30-2 surrounded by the annular member 26-2. This arrangement makes it possible to maintain the required low pressure within the electron beam irradiation space 30-2 so that electron beam irradiation can be performed without problems. Double or triple annular channels may be provided, depending on pressures within the chamber C and the electron beam irradiation space 30-2.

Dry nitrogen is commonly used as the high pressure gas supplied to the static pressure bearings. If possible, however, it is preferable to use an inert gas of higher purity. If gas containing traces of moisture or oil is used, molecules of these impurities can adhere to the inside surfaces of the housing that forms the vacuum chamber, the surfaces of components that make up the stage, and the surfaces of samples, and the level of vacuum within the electron beam irradiation space will be degraded.

In apparatus such as that described above, samples W are not normally placed directly on the X table, but rather on a sample holder that is capable of releasably holding the sample and making fine adjustments in the positioning thereof with respect to the XY stage 3-2. To simplify the description, however, since neither the use of such a sample holder nor the construction thereof is related to the gist of the invention of the present application, its description has been omitted.

Since static pressure bearing-type stage mechanisms designed for use at atmospheric pressure can be used substantially as-is in the above-described electron beam inspection apparatus, it is possible to realize a high precision XY stage for an electron beam inspection apparatus that is the same size, and is otherwise equivalent to, the high precision atmospheric pressure stages used in lithography systems, etc., and at about the same cost.

Moreover, the configuration and placement of the static pressure guides and actuator (linear motor) described above constitute only one possible embodiment; any static pressure guide or actuator that can be used in the atmosphere may be used here.

Next, a quantitative example of the size of the annular member 26-2 of the differential discharge mechanism, and the annular channel formed therein will be discussed with reference to FIG. 20. This example has double annular channels 27a-2 and 27b-2, separated from each other in the radial direction.

The flow rate of the high pressure gas to the static pressure bearings is normally around 20 L/min (converted to atmospheric pressure terms). If a vacuum chamber C is evacuated by a dry pump having a pumping speed of 20,000 L/min, through a cylindrical vacuum line 2 meters long and 50 mm in inside diameter, the pressure in the vacuum chamber will be about 160 Pa (approximately 1.2 Torr).

Figure 20:
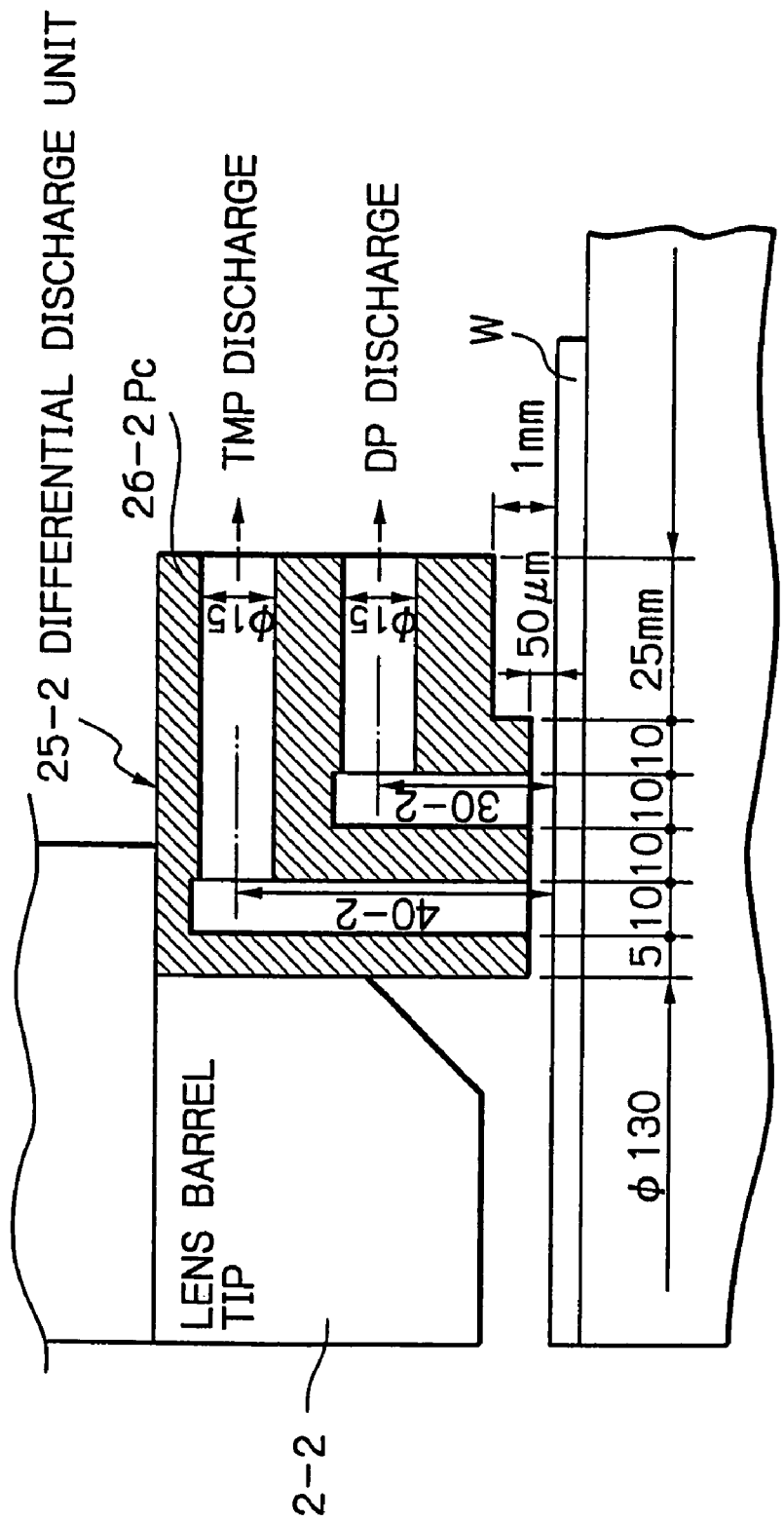
FIG. 20 shows an example of the operation of a differential discharge mechanism provided in the apparatus of FIG. 19.

Under these conditions, if the dimensions of the differential pumping mechanism annular member 26-2 and its annular channel, etc. are as shown in FIG. 20, then a pressure of $10^{-4}$ Pa ($10^{-6}$ Torr) can be obtained within the electron beam irradiation space 30-2.

A second embodiment is shown in FIG. 21. The vacuum chamber C formed by the housing 14-2 is connected to a dry vacuum pump 53-2 through vacuum lines 74-2 and 75-2. The annular channel 27-2 of the differential pumping mechanism 25-2 is connected, through a vacuum line 70-2 connected to the pumping outlet 28-2, to a turbomolecular pump 51-2 (an ultra-high vacuum pump). In addition, the interior of the column 1-2 is connected to a turbomolecular pump 52-2 through a vacuum line 71-2 connected to the its discharge outlet 18-2. These turbomolecular pumps 51-2 and 52-2 are connected through vacuum lines 72-2 and 73-2 to a dry vacuum pump 53-2.

In this drawing, a single dry vacuum pump is assigned double duty as the roughing pump for the turbomolecular pumps and also as the vacuum evacuation pump for the vacuum chamber. However, depending on factors such as the flow rate of the high pressure gas supplied to the XY stage static pressure bearings, the internal surface area and volume of the vacuum chamber, and the inside diameter and length of the vacuum lines, there may be cases in which a separate dry vacuum pump system would be appropriate.

High-purity inert gas ($N_2$, Ar, etc.) is supplied to the static pressure bearings of the XY stage 3-2 through the flexible lines 21-2 and 22-2. Molecules of these gases blown from the static pressure bearings are dispersed in the vacuum chamber and pumped through pumping outlets 19-2, 20a-2, and 20b-2, by the dry vacuum pump 53-2. Any of these molecules that manage to penetrate into the differential discharge mechanism or electron beam irradiation space are drawn out of the annular channel 27-2 or the output end of the column 1-2, to be discharged through the discharge outlets 28-2 and 18-2 by the turbomolecular pumps 51-2 and 52-2. After pumping from the turbomolecular pumps, the molecules are again pumped by the dry vacuum pump 53-2. In this manner, high-purity inert gas supplied to the static pressure bearings is collected and pumped by the dry vacuum pump.

The pumping outlet of the dry vacuum pump 53-2 is connected through the tube 76-2 to a compressor 54-2. The pumping outlet of the compressor 54-2 is connected to the flexible tubes 21-2 and 22-2 through the lines 77-2, 78-2, 79-2, and the regulators 61-2 and 62-2. Thus, after the high-purity inert gas pumped from the dry vacuum pump 53-2 is re-pressurized by the compressor 54-2 and adjusted to the proper pressure by the regulators 61-2 and 62-2, it is again supplied to the static pressure bearings of the XY table.

As mentioned above, the gas supplied to the static pressure bearings must be kept at the highest possible level of purity, with the least possible moisture and oil content. Therefore, the turbomolecular pumps, dry pumps, and compressor must be constructed to prevent entry of moisture or oil into the gas flow path. Also, a cold trap or filter (60-2), provided midway in the tube 77-2 connected to the pumping side of the compressor, can be effective in trapping impurities such as moisture or oil mixed in with the re-circulated gas, to prevent their being supplied to the static pressure bearings.

This recirculation and reuse of high-purity inert gas conserves gas, and also avoids the discharging of used inert gas into the room in which the equipment is installed, thus eliminating the possibility of having any inert gas asphyxiation accidents.

A high-purity gas supply system 63-2 is connected to the gas circulation tubing system. This system has two functions: it fills the entire gas circulation system, including the vacuum chamber C and vacuum evacuation lines 70-2 through 75-2 and pressurization lines 76-2 through 80-2, with high-purity inert gas when gas circulation is initiated; and it supplies additional gas if, for some reason, a reduction in the flow rate of the circulating gas occurs during operation.

It is also possible to have a single pump perform the functions of both the dry vacuum pump 53-2 and the compressor 54-2, by assigning, to the dry vacuum pump 53-2, the function of compressing the gas to greater than atmospheric pressure.

In addition, instead of using a turbomolecular pump as the ultra-high vacuum pump for evacuating the column, another type of pump such as an ion pump or getter pump may be used. When pooling pumps such as this are used, however, it will not be possible to construct a circulation tubing system in this part of the system. Also, instead of a dry vacuum pump, a diaphragm-type dry pump, or other type of dry pump may, of course, be used.

Effects of an Electron Beam Inspection Apparatus with an Improved Stage

The following effects can be brought to fruition through the use of an electron beam inspection apparatus of the present invention equipped with a stage such as described above.

a. Stable electron beam processing of a sample on a stage can be performed using a stage of the same construction as that of a static pressure bearing-type stage of the type normally used in the atmosphere (a static pressure bearing support stage without a differential pumping mechanism).

b. It will be possible to reduce detrimental effects on the level of vacuum in the electron beam irradiation region to an absolute minimum, thus providing for stable processing of samples by the electron beam.

c. An inspection apparatus with high precision stage positioning performance, and highly stable vacuum in the electron beam irradiation region can be provided at low cost.

d. Lithography apparatus with high precision stage positioning performance, and highly stable vacuum in the electron beam irradiation region can be provided at low cost.

e. It will be possible to form extremely fine-featured semiconductor circuits by using an inspection apparatus with high precision stage positioning performance and highly stable vacuum in the electron beam irradiation region to manufacture those circuits.

Maintenance of Vacuum in the Working Chamber (Stage Improvement 2)

In the description of the above improvement related to the maintenance of vacuum in the working chamber (Stage Improvement 1), a prior system having a stage comprising a differential discharge mechanism combined with static pressure bearings was described. In this system, when the stage moved, guide surfaces opposite the static pressure bearings moved back and forth between the high pressure gas atmosphere in the static pressure bearing portion and the vacuum environment in the chamber. When this occurred, during the time the guide surface was exposed to the high pressure gas atmosphere, gas was adsorbed on the surface; and during the time it was exposed to the vacuum atmosphere gas was released, in a continually repeating cycle. This produced a phenomenon in which the level of vacuum in the chamber was further degraded with each movement of the stage, making stable performance of electron beam processes such as lithography, wafer inspection, or micromachining impossible, and there were therefore problems with samples becoming contaminated.

It is an object of the present invention to overcome the above problem of the prior system by providing an electron beam inspection apparatus having a stage improved as described below.

Electron Beam Apparatus with an Improved Stage

First Embodiment

Figure 22A:
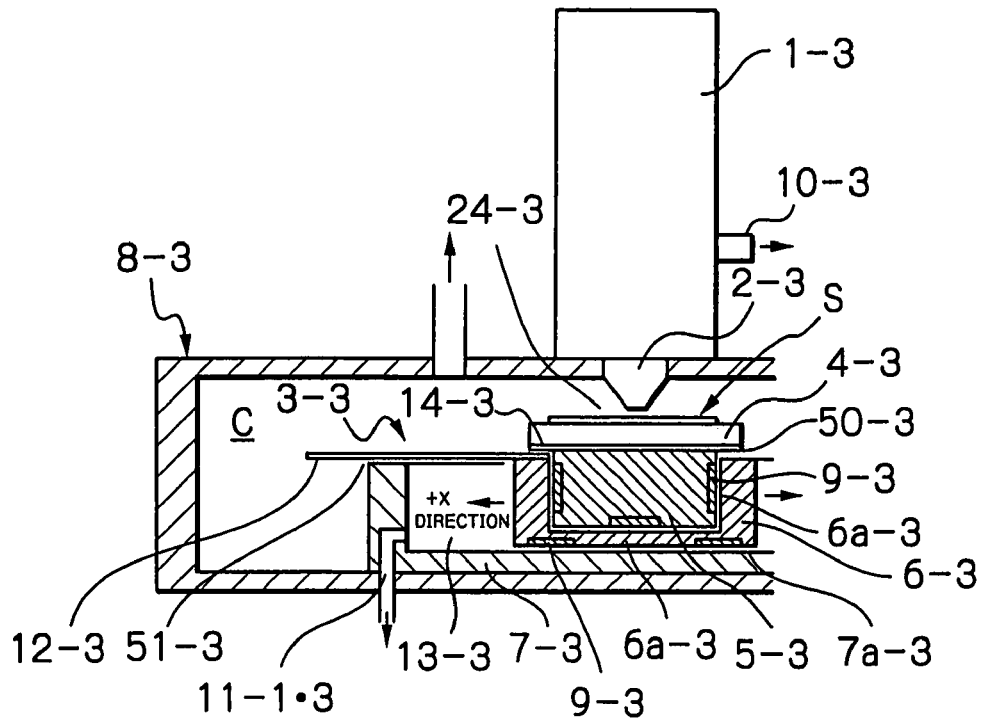
FIGS. 22(A) and (B), respectively, show front and side views of the vacuum chamber and XY stage in one embodiment of the electron beam apparatus of the present invention.
Figure 22B:
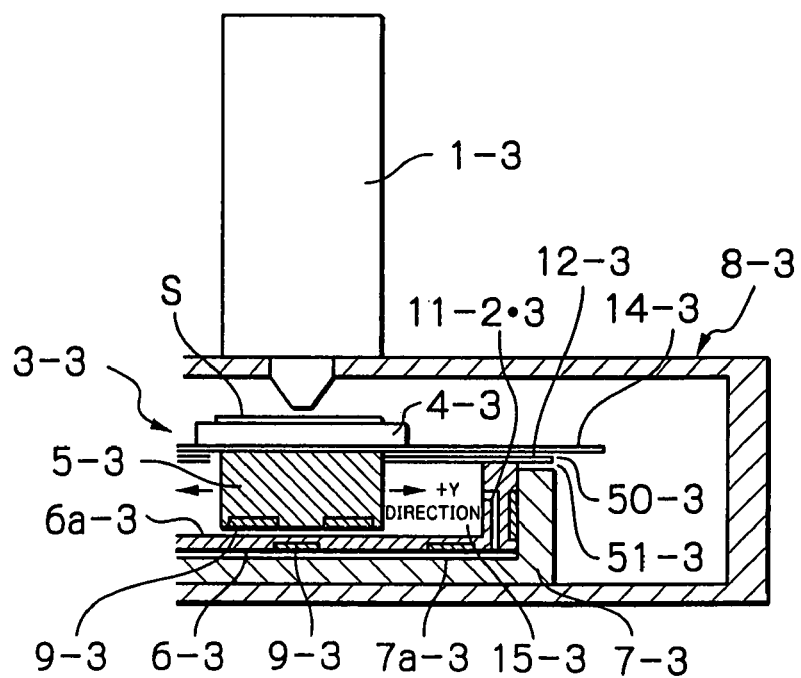

A first embodiment of the apparatus is shown in FIGS. 22(A) and (B). Installed on the top surface of a Y-movable unit 5-3 of a stage 3-3 is a diaphragm 14-3 made with a large, substantially horizontal, overhang in the +Y and −Y directions (the rightward and leftward directions of FIG. 22(B)), and with a constantly-low-conductance gap closure stop 50-3 disposed between the diaphragm and the top surface of an X-movable unit 6-3. Also, installed on the top surface of the X-movable unit 6-3, is a similar diaphragm 12-3 having an overhang in the +X and −X directions (the leftward and rightward directions of FIG. 22(A)), with a gap closure stop 51-3 sandwiched between the diaphragm and the top surface of a stage mount 7-3. The stage mount 7-3 is attached to the floor plate of a housing 8-3 by a known method.

The gap closure stops 50-3 and 51-3 are always formed such as to close the opening, regardless of the location into which a sample seat 4-3 is moved. Therefore, any gas expelled from guide surfaces 6a-3 and 7a-3 during movement of the movable units 5-3 and 6-3 will be blocked from entering into the space C by the gap closure stops 50-3 and 51-3. This minimizes pressure fluctuations in the proximity of a space 24-3 (the space in which the sample is irradiated by the electron beam).

Although not shown in FIGS. 22(A) and (B), formed in the side and bottom surfaces of the Y-movable unit 5-3 of the stage 3-3 and the bottom surface of the X-movable unit 6-3, around a static pressure bearing 9-3, are differential pumping channels as shown in FIG. 2. Because these channels are evacuated to a vacuum state, gas expelled from the guide surfaces while the gap closure stops 50-3 and 51-3 are re-forming, is pumped mainly through these differential pumping channels. This makes the pressure in the stage (in the spaces 13-3 and 15-3) higher than the pressure in the chamber C. Also, if in addition to discharging the spaces 13-3 and 15-3 through the differential pumping channels, separate vacuum-evacuated locations are provided, the pressure in the spaces 13-3 and 15-3 can be reduced, thereby minimizing any pressure increase in the region 24-3 near the sample. Vacuum evacuation paths 11-1.3 and 11-2.3 are provided for this purpose. The pumping path 11-1.3 passes through the stage 7-3, and the housing 8-3, to the exterior of the housing 8-3. The discharge path 11-2.3 is formed in the X-movable unit 6-3, with its outlet in the bottom surface thereof.

Also, when the diaphragms 12-3 and 14-3 are installed, the chamber has to be enlarged to prevent interference between the chamber C and the diaphragms. This can be overcome, however, by using a design or material for the construction of the diaphragms that will enable them to extend and retract. In this embodiment, an accordion-type flexible rubber construction is employed, with the ends of the diaphragms in the directions of motion thereof fastened to the X-movable unit 6-3 (if it is a diaphragm 14-3), or to the inside wall of the housing 8-3 (if it is a diaphragm 12-3).

Second Embodiment

Figure 23:
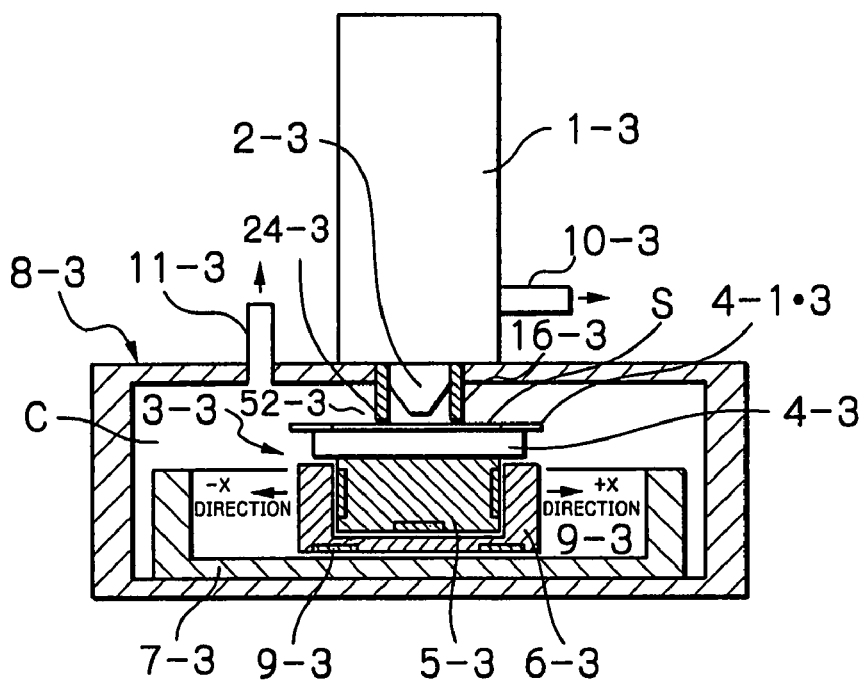
FIG. 23 shows the vacuum chamber and XY stage of another embodiment of the electron beam apparatus of the present invention.

A second embodiment of the apparatus is shown in FIG. 23. In this embodiment, a cylindrical diaphragm 16-3 is placed around the electron beam irradiator 2-3 (the output end of the column), between the column and the top of the sample S, for forming a gap closure stop. In this configuration, if gas escapes from the XY stage, increasing the pressure in the chamber C, because the diaphragm interior 24-3 is partitioned off by the diaphragm 16-3, and is being evacuated through the vacuum line 10-3, a pressure difference can develop between the space inside the chamber c and the diaphragm interior 24-3, and any increase in pressure in the space within the diaphragm interior 24-3 can therefore be kept small. As for the size of the gap between the diaphragm 16-3 and the surface of the sample, it varies depending on the approximate pressure to be maintained in the chamber C and around the irradiator 2-3, but generally, a gap of from a few μm to a few mm is appropriate. Also, communication between the diaphragm 16-2 interior and the vacuum line is established by a known method.

Also, in some electron beam irradiation systems, high voltage on the order of several kV is applied to the sample S, and discharge could therefore occur if conductive material is placed near the sample. In such systems, discharge between the diaphragm 16-3 and the sample S can be avoided by making the diaphragm 16-3 of an insulator material such as ceramic.

A ring member 4-1.3 placed around the sample S (wafer) is a planar adjustment component attached to the wafer seat 4-3. It is set to the same height as the wafer, in order to form an ultra-fine gap 52-3 fully around the bottom edge of the diaphragm 16-3. This permits operation even in cases where the electron beam irradiation must be performed near the outer edge of a sample such as a wafer. Because of this, regardless of where, on the sample S, the point being irradiated by the electron beam is located, the bottom edge of the diaphragm 16-3 will always form a gap 52-3 of a set size, thus ensuring that the pressure in the space 24-3 around the output end of the column can be held stable.

Third Embodiment

Figure 24:
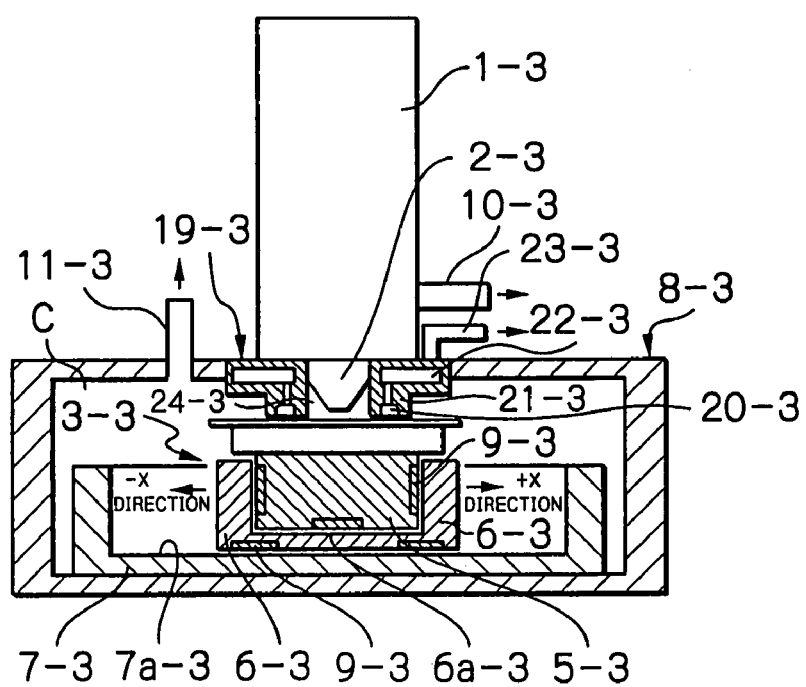
FIG. 24 shows the vacuum chamber and XY stage of a different embodiment of the electron beam apparatus of the present invention.

A third embodiment, shown in FIG. 24 uses essentially the same configuration as that described above (Stage Improvement 1, for improving the maintenance of stable vacuum in the working chamber). In this embodiment, a diaphragm 19-3 with a built-in differential discharge structure is provided around the electron beam irradiator 2-3 of the column 1-3. The diaphragm 19-3 is cylindrical in shape, and has a circular channel 20-3 formed inside, with a pumping path 21-3 extending upward from the circular channel. This discharge path connects to a vacuum line 23-3 through an internal space 22-3. An ultra-fine gap of from a few tens of μm to a few mm is formed between the bottom end of the diaphragm 19-3 and the top surface of the sample S.

In this configuration, when gas is emitted from the stage during its movement, raising the pressure in the chamber C, and thus urging a flow of gas into the electron beam irradiator 2-3 (output end of the column), because the diaphragm 19-3 has closed the gap between itself and the sample S, reducing the conductance therethrough to an extremely low value, the flow of gas is impeded and the flow rate reduced. In addition, because inflowing gas is emitted through the circular channel 20-3 to the vacuum line 23-3, almost no gas flows into the space 24-3 around the electron beam irradiator 2-3, and the pressure at the electron beam irradiator 2-3 can therefore be maintained constant at the desired level of high vacuum.

The differential pumping structure provided in the diaphragm 19-3 is as shown in FIG. 19 through FIG. 21.

Fourth Embodiment

Figure 25:
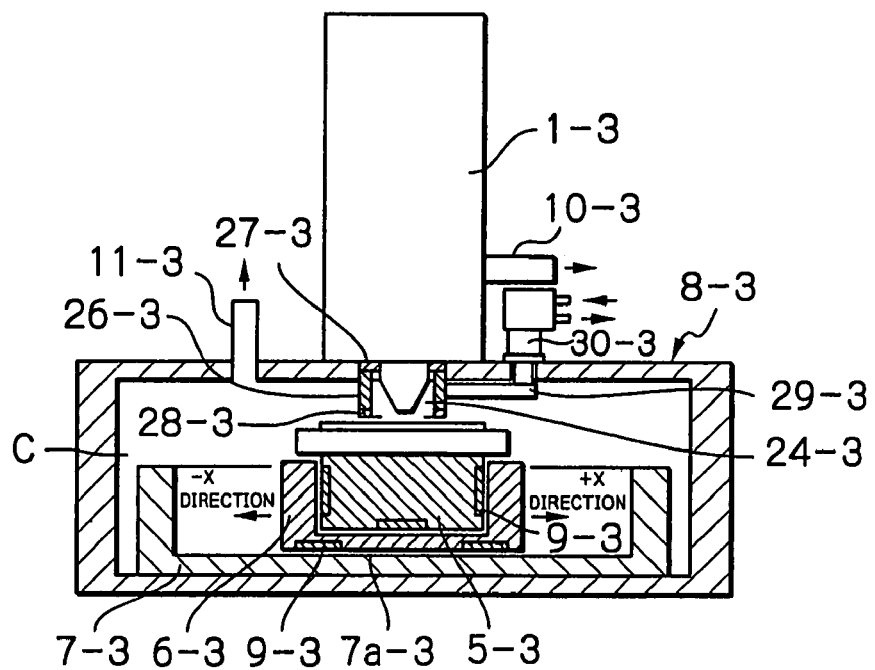
FIG. 25 shows the vacuum chamber and XY stage of yet another embodiment of the electron beam apparatus of the present invention.

A fourth embodiment is shown in FIG. 25. A diaphragm 26-3 is provided around a chamber C and an electron beam irradiator 2-3, for separating the electron beam irradiator 2-3 from the chamber C. This diaphragm 26-3 is connected through a support member 29-3 (made of a material that is a good conductor, such as copper or aluminum) to a refrigeration unit 30-3, which cools it to between −100° C. and −200° C. A member 27-3, for blocking thermal conduction between the chilled diaphragm 26-3 and the column, is made of a material of poor thermal conductivity, such as a ceramic or resin. Also, a member 28-3, made of a non-insulating ceramic, etc., is formed at the bottom end of the diaphragm 26-3, to prevent discharge between a sample S and the diaphragm 26-3.

Through such a configuration, gas molecules attempting to flow from the chamber C to the electron beam irradiator are blocked by the diaphragm 26-3, and any gas that does manage to enter is frozen onto the surface of the diaphragm 26-3. Low pressure can therefore be maintained at the electron beam irradiator 24-3.

For the refrigeration unit, a wide variety of refrigeration units such as a chiller using liquid nitrogen, an He refrigeration unit, or a pulse tube-type refrigeration unit, etc. may be used.

Fifth Embodiment

Figure 26:
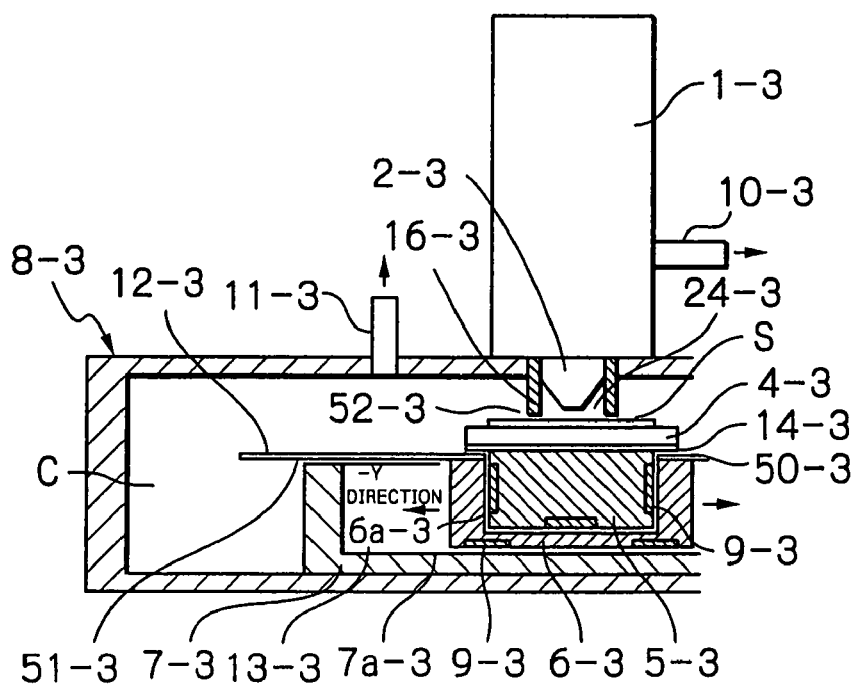
FIG. 26 shows the vacuum chamber and XY stage of another embodiment of the electron beam apparatus of the present invention.

A fifth embodiment is shown in FIG. 26. Provided on the two movable units of the stage 3-3 are the same diaphragms 12-3 and 14-3 as are shown in FIG. 22. Therefore, regardless of where the sample stage 4-3 is moved, these diaphragms, through the gap closure stops 50-3 and 51-3, will partition off the inner space 13-3 from the chamber C. In addition, formed around the electron beam irradiator 2-3, is a diaphragm 16-3 like the one shown in FIG. 23, for partitioning off the inside of the chamber C from the electron beam irradiator 2-3 space 24-3, through a gap closure stop 52-3. Through this configuration, when gas adsorbed during stage movement is discharged into the space 13-3, raising the pressure in this portion, any increase in pressure in the chamber C can be suppressed, and any pressure increase within the space 24-3 can be even further suppressed. In this manner, the pressure in the electron beam irradiation space 24-3 can be maintained in a low pressure state. Also, a differential pressure mechanism such as that as shown in FIG. 24 for the diaphragm 16-3, can be used for the diaphragm 19-3. Also, by using a diaphragm 26-3 cooled by a refrigeration unit as shown in FIG. 25, the space 24-3 can be stably maintained at an even lower pressure.

Effects of an Electron Beam Apparatus with an Improved Stage (2)

In an electron beam inspection apparatus such as described above, the following effects can be obtained:

a. The stage system is capable of providing high precision positioning performance in a vacuum while also making it difficult for the pressure near electron beam irradiation position to rise. Thus more precise processes can be performed on the sample by the electron beam.

b. Almost none of the gas emitted by the static pressure bearing wafer support system can pass through the diaphragm into the region of electron beam irradiation. This makes the vacuum at the location being irradiated by the electron beam more stable.

c. Because it is harder for discharged gas to penetrate into the region in which electron beam irradiation region is taking place, it is easier to hold stable vacuum in this electron beam irradiation region.

d. The vacuum chamber interior is partitioned by low conductance barriers into three chambers: an electron beam irradiation chamber, a static pressure bearing chamber, and intermediate chamber. Also, the vacuum evacuation system is configured such that the pressures in the respective chambers increase from chamber to chamber in the following order: electron beam irradiation chamber (lowest pressure), intermediate chamber (intermediate pressure), and static pressure bearing chamber (highest pressure).

Pressure changes induced in the intermediate chamber are further reduced by a diaphragm, and pressure changes induced in the electron beam irradiation chamber are reduced by an additional step by another diaphragm, ultimately reducing pressure fluctuations to a level at which they are virtually a non-problem.

e. Increased pressure during stage motion can be kept at a low level.

f. Increased pressure during stage motion can be kept at an even lower level.

g. Because an inspection apparatus having both highly accurate stage positioning performance and stable vacuum in its electron beam irradiation region can be realized, an inspection apparatus featuring high inspection performance with no sample contamination problems can be provided.

h. Because a lithography system having both highly accurate stage positioning performance and stable vacuum in its electron beam irradiation region can be realized, a lithography system featuring high inspection performance with no sample contamination problems can be provided.

i. It will be possible to form extremely fine semiconductor circuits through the use of apparatus having highly accurate stage positioning performance and stable vacuum in the electron beam irradiation region.

Improving Throughput (Electron Optics With Multiple Optical Systems (Columns))

In the above embodiment of the electron optical system of the inspection apparatus, an electron beam emitted from a single electron source was passed through an aperture plate having multiple apertures in order to form multiple beams (multibeam beamlets). These multiple beams were used to improve throughput in a column with a single optical system for performing wafer inspections. In the present aspect of the invention, however, multiple columns (optical systems) are provided. These multiple optical systems make it possible to inspect a number of different areas (and thus a larger total area) at the same time, to thus provide an electron beam optical apparatus capable of an even greater improvement in throughput.

First Embodiment of Electron Optical Apparatus With Multiple Optical Systems (Columns)

Figure 28:
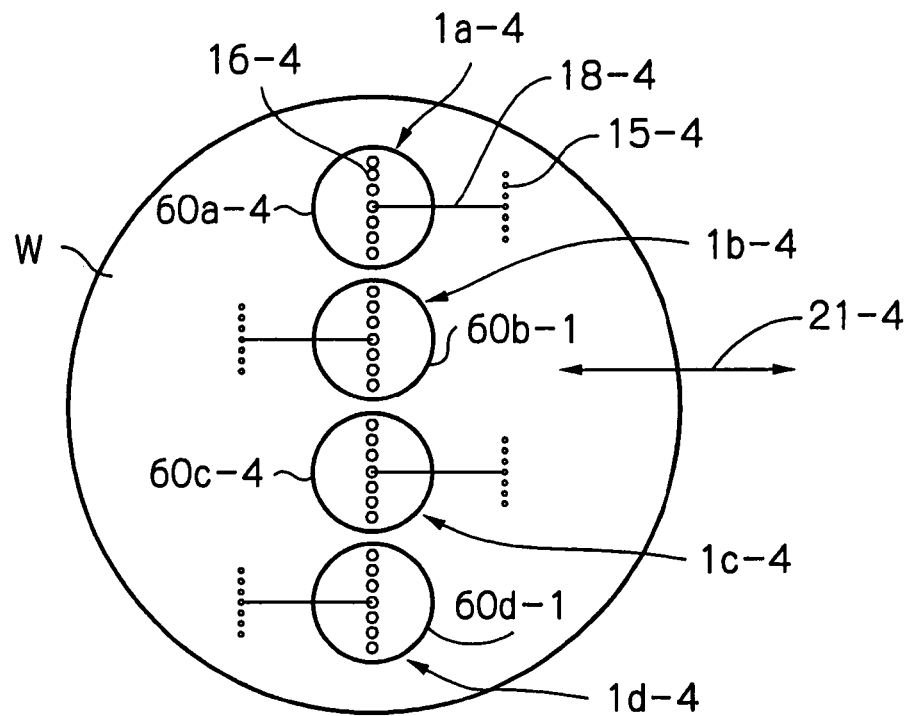
FIG. 28 shows a first placement configuration of multiple optical systems in the multiple column electron optical system of the present invention.

In this first embodiment, as shown in FIG. 28, four electron optical systems (columns) 1a-4, 1b-4, 1c-4 and 1d-4 (with the maximum diameters 60a-4, 60b-4, 60c-4 and 60d-4, respectively) are used to scan the surface of a wafer W for inspection. The four optical systems are placed over the wafer along a line perpendicular to the direction of motion 21-4 of a stage 48-4 (i.e., the wafer W).

Each of the electron optical systems 1a-4, 1b-4, 1c-4, and 1d-4, which all have the basic configuration shown in FIG. 7(b), comprises an electron gun 1-4;
a condenser lens 2-4;
a multi-aperture plate 3-4;
an aperture stop 4-4
a condenser lens 5-4;
an ExB separator 7-4;
electrostatic deflectors 6-4 and 8-4;
an objective lens 10-4;
magnification lenses 12-4 and 13-4;
a detector aperture plate 14-4;
a detector 15-4;
a deflector 20-4;

a stage 48-4;
a controller 50-4; and
a display 52-4.

Figure 27A:
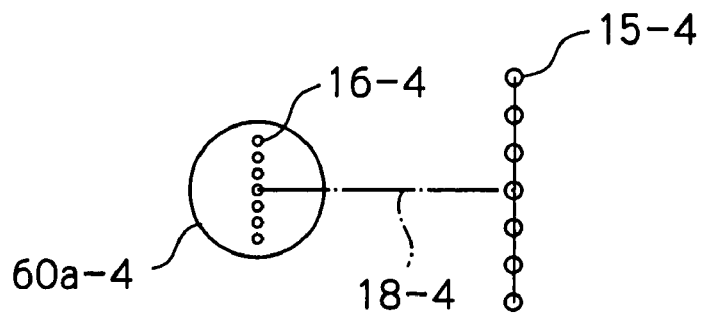
FIGS. 27(a)) and (b), respectively, show top and side view schematic representations of the optical system of one of the columns of a multiple column electron optical system of the present invention.
Figure 27B:
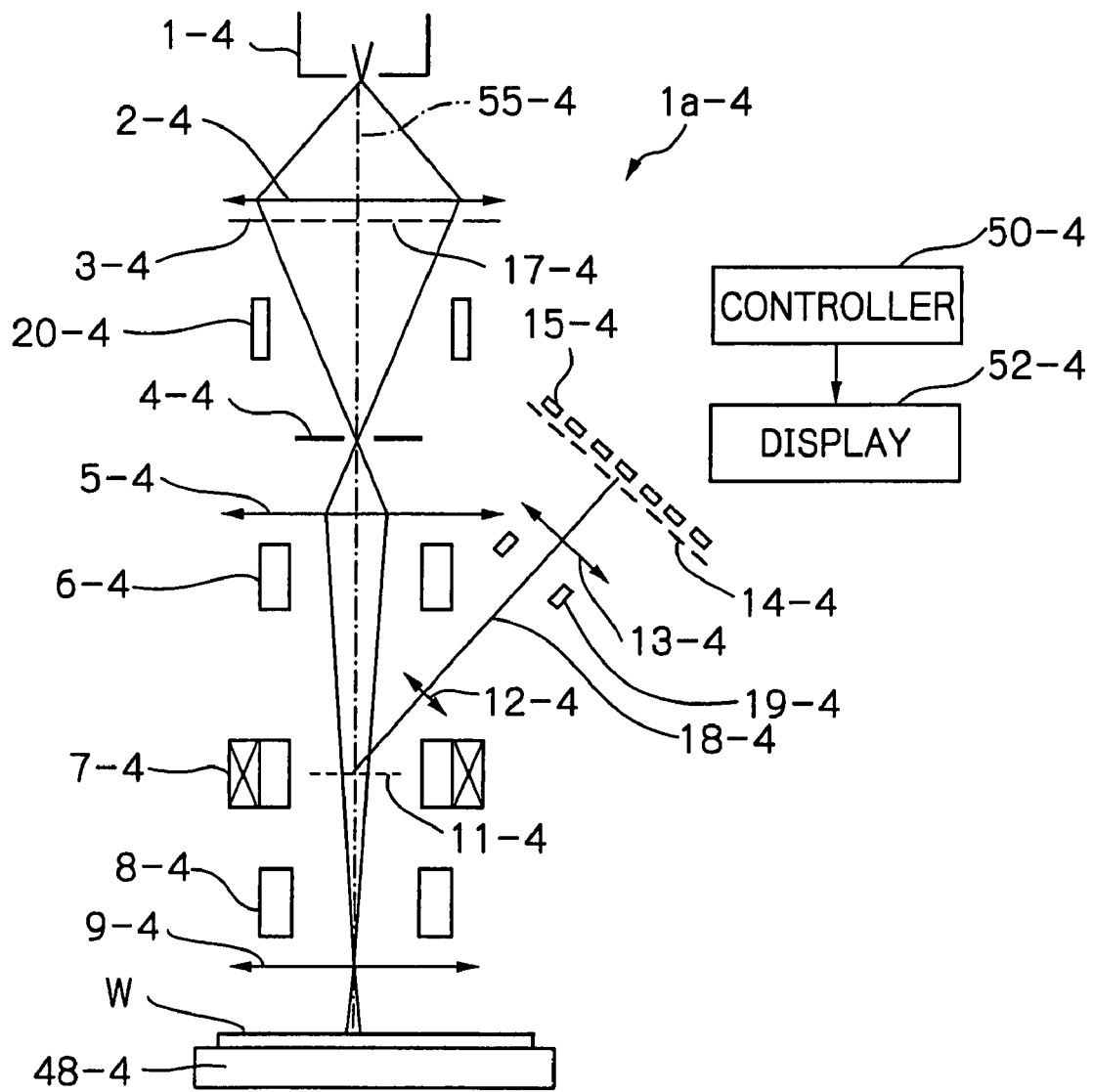

FIG. 27(*a*)) is a top view showing typical positional relationships between the primary electron beam irradiation system (primary optical system) and the secondary electron beam detection system of the optical system 1*a*-4 (one of the four optical systems in FIG. 28). Here, the outline 60*a*-4 represents the maximum diameter of the primary electron beam irradiation system, and each of the equally spaced circles on the diameter line of the maximum diameter outline 60*a*-4 represents one of the multi-aperture regions 16-4 of a primary electron beamlet that has passed through one of the apertures 17-4 of the multi-aperture plate 3-4. The line 18-4 represents the optical axis of the secondary electron detector. The secondary electron beamlet emitted from the wafer by electron beam irradiation of the multi-aperture region 16-4 is deflected by the ExB separator 7-4. Then it passes along the optical axis 18-4, where it is magnified, and is then detected by its corresponding detector element in the detector 15-4. Corresponding positional relationships between the primary electron beam irradiation system and the secondary electron detection system are defined so that each beamlet will be detected by a specific one of the multiple detector elements of the detector 15-4. As will be understood more clearly from the drawings, each of the multi-aperture regions 16-4 (i.e. each of the multiple apertures 17-4), is paired with a specific one of the multiple detector elements, such as to prevent the occurrence of crosstalk between the beamlets along the way.

Each of the other optical systems that make up the total electron optical system of the present embodiment (1*b*-4, 1*c*-4, and 1*d*-4) also has a primary electron beam irradiation system, an ExB separator, and a secondary electron detection system as described above. The controller 50-4 and stage 48-4 can be used in common by all of the optical systems. The secondary electron beam image processing circuits, etc., constitute some of the functions of the controller 50-4. If necessary, however, rather than imbedding these circuits entirely within the controller, they may be provided in the individual optical systems. These multiple optical systems 1*a*-4, 1*b*-4, etc. are all placed in a line over the same wafer such that each irradiates a different region of the wafer with primary electrons, and each detects secondary electrons from its own region.

To prevent optical systems from interfering with each other, the secondary optical axes 18-4 of the optical systems are aligned with the direction of motion of the stage 21-4 (i.e. perpendicular to the line along which the optical systems are placed) such that adjacent axes are directed away from the line in opposite directions. This arrangement causes each axis to be aligned with a multiple aperture region 16-4 and an element of the detector 15-4, and perpendicular to the direction of stage motion 21-4.

With optical systems placed as shown in FIG. 28, if we assume a maximum diameter of 40 mmφ for a primary electron beam irradiation system, it would be possible to place five optical systems over an 8-inch (approximately 20-cm) wafer. Since this would put much of the peripheral portions of the optical systems off the wafer, however, the practical limit is four optical systems. However, if a maximum diameter of 30 mmφ is feasible, this number can be increased to around six.

Next, the operation of this electron beam optical apparatus will be described. A single primary electron beam emitted from the electron gun 1 in each of the optical systems 1*a*-4 through 1*d*-4 is converged by the condenser lens 2-4 to form a crossover image at the aperture stop 4-4. Along the way, the primary electron beam of each optical system illuminates the multi-aperture plate 3-4, which forms seven beamlets (in this embodiment) as they pass through the apertures 17-4. Images of these multiple beamlets are formed on a main surface 11-4 of the ExB separator 7-4 by the condenser lens 5-4, and are again formed as demagnified images on the wafer W, by the objective lens 9-4. At this time, seven beam spots on the wafer are irradiated for each optical system (see FIG. 28), and secondary electrons are emitted from each of these spots. The electrostatic deflectors 6-4 and 8-4 deflect the beamlets perpendicular to the direction of stage motion 21-4, over an area slightly larger than the separation between adjacent beamlets. This deflection enables the irradiated spots on the wafer to be scanned along the direction of the row of beams without interruption. As the beams are being scanned in this manner, the stage 48-4 is controlled in continuous synchronous motion, through successive periodic sweeps of prescribed width in the direction of stage motion 21-4, thus making it possible to scan the entire inspection surface of the wafer. For example, if we assume that the width that can be scanned in the direction of the row of beams by the four electron optical system is 2 mm, then in 20 consecutive sweeps of the stage, it will be possible to evaluate an area 160×160 mm in size (with all four optical systems).

The multiple secondary electron beamlets emitted from the irradiated spots are accelerated substantially perpendicularly upward to arrive at the ExB separator 7-4, where they are deflected at a prescribed angle with respect to the optical axis 55-4 by ExB fields that exist in the separator, and continue along the optical axis 18-4 of the secondary optical system. The separation between these multiple secondary electron beamlets is increased by magnification lenses 12-4 and 13-4, and they pass through the detector aperture plate 14-4 to be detected by the multiple detector elements 15-4. At the same time, mispositioning of the secondary electron beamlets due to deflection of the primary electron beam by the deflectors 6-4 and 8-4 is offset by the correction deflector 19-4. In other words this correction is made such that regardless of what occurs during the primary electron beam scan, each of the secondary electron beamlets will always pass through its own particular aperture of the detector aperture plate 14-4 to be detected by its own detector element behind that aperture. The multiple detector elements 15-4 output signals indicative of the intensity of the secondary electron beam to the controller 50-4. The controller 50-4 receives the output signals from the detector elements 15-4 serially, in synchronization with primary electron beam-deflector control and stage 48-4 motion control, and ultimately obtains therefrom, an image of secondary electron beam intensity distribution over the entire inspection surface of the semiconductor wafer W.

The controller 50-4 compares actual detected secondary electron beam images with the secondary electron beam image of a defect-free wafer, that is stored in memory in advance, in order to automatically detect defective portions. Also, when a wafer has a large number of identical dies, defective portions may also be detected by comparing the detected images of the inspected dies against each other.

When performing inspections, in addition to displaying the detected images on the display 50-4, portions judged defective can be marked with defect indicators. Operators can then make a final check and evaluation of the wafers W to determine whether it actually has defects.

Figure 30:
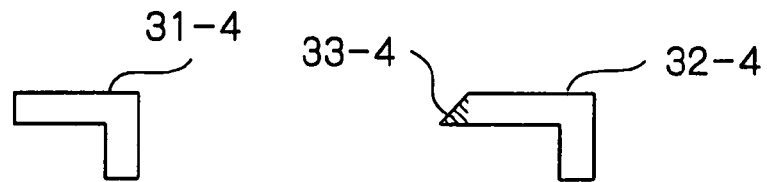
FIG. 30 is a drawing to aid the description of a pattern defect detection method.

Specific examples of defect inspections are shown in FIGS. 30 though 32. First, shown in FIG. 30 is a die 31-4 that was the first one inspected, and another die 32-4 that was the second on inspected. If the image of a separate die inspected third is judged to be similar or identical to the first die 31-4 inspected first, then the portion 33-4 of the second inspected die 32-4 is judged defective, and the defective portion of it is inspected.

Figure 31:
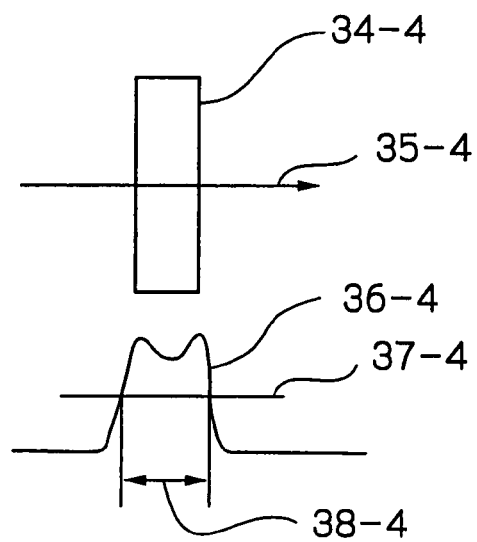
FIG. 31 is a drawing to aid the description of a line width measurement method.

FIG. 31 shows an example of measurement of the line width in a pattern formed on a wafer. The signal 36-4 represents the actual secondary electron intensity signal obtained when an actual wafer pattern 34-4 was scanned in a direction 35-4. The line 37-4 indicates a threshold level calibrated in advance for the signal 36-4. The width (38-4) of the portion of that signal that continuously exceeds the threshold is then measured as the line width of the pattern line 34-4. When the measured line width of a pattern falls outside of a prescribed range, that pattern is judged to be defective.

Figure 32:
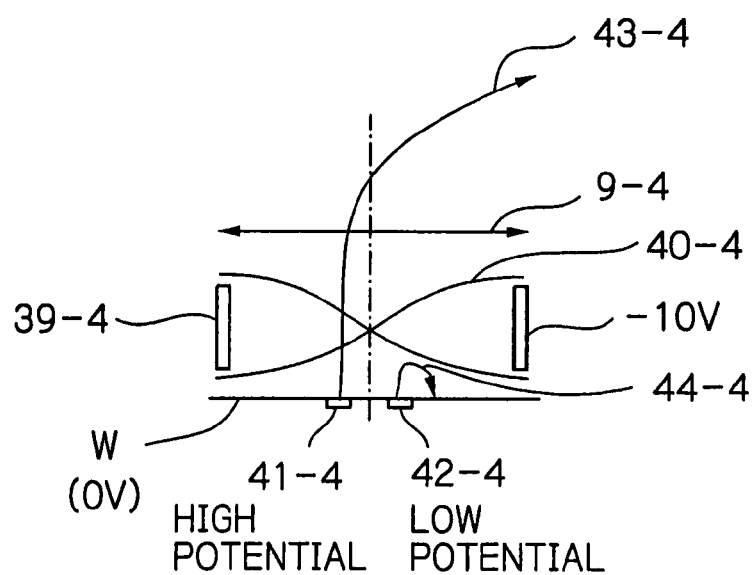
FIG. 32 is a drawing to aid the description of an electrical potential contrast measurement method.

FIG. 32 shows an example of measurement of electrical potential contrast of a pattern formed on a wafer W. An axially symmetrical electrode 39-4 (FIG. 32) is placed in the configuration shown in FIG. 27(*b*), between the objective lens 9-4 and the wafer. A voltage is applied to this electrode 39-4 such as to place it at a potential of −10 V, for example, with respect to the wafer (which is at 0 V potential). The −2 V equipotential plane will be assumed to have the form indicated by the curve 40-4. Also, the potential on the pattern 41-4 is assumed to be −4 V, and that on the pattern 42-4 is assumed to be 0 V. Under these conditions, since the secondary electrons emitted from the pattern 41-4 (at −4 V) will have an upward velocity equivalent to 2 eV of kinetic energy at the equipotential plane 40-4, they will pass through this potential barrier 40-4, and escape from the electrode 39-4 along the trajectory 43-4, to be detected by the detector 15-4.

Secondary electrons emitted from the 0 V pattern 42-4, however, cannot overcome the −2 V potential barrier, and will therefore return to the wafer surface along the trajectory 44-4, without being detected. The detected image of the pattern 41-4, then, will be clear, and that of the pattern 42-4 will be dark. In this manner, potential contrast is obtained. If the brightness of the detected image and potential are calibrated in advance, the pattern potential can be measured via the detected image. Also, defective portions of a pattern can be found by analyzing the potential distribution of the pattern.

A blanking deflector 20-4 is provided is the configuration of FIG. 27(*b*). This deflector can be used to generate a pulsed beam with short pulse duration by causing the deflector 20-4 to deflect the primary electron beam away from the aperture portion of the aperture stop 4-4 in a repeating cycle of a prescribed period, such that the beam will pass through the aperture for only a short portion of each cycle, and will be blocked the rest of the time. If such a narrow-pulse pulsed beam is used to measure the potentials on a wafer, as described above, time domain analyses of device operation can be performed with high time resolution. In other words the present electron optical system can be used as a multibeam EB tester.

In this first embodiment, the stage 48-4 operation has few return operations. This results in wasted time associated with stage movement (wasted time that can be reduced).

Second Embodiment

Figure 29:
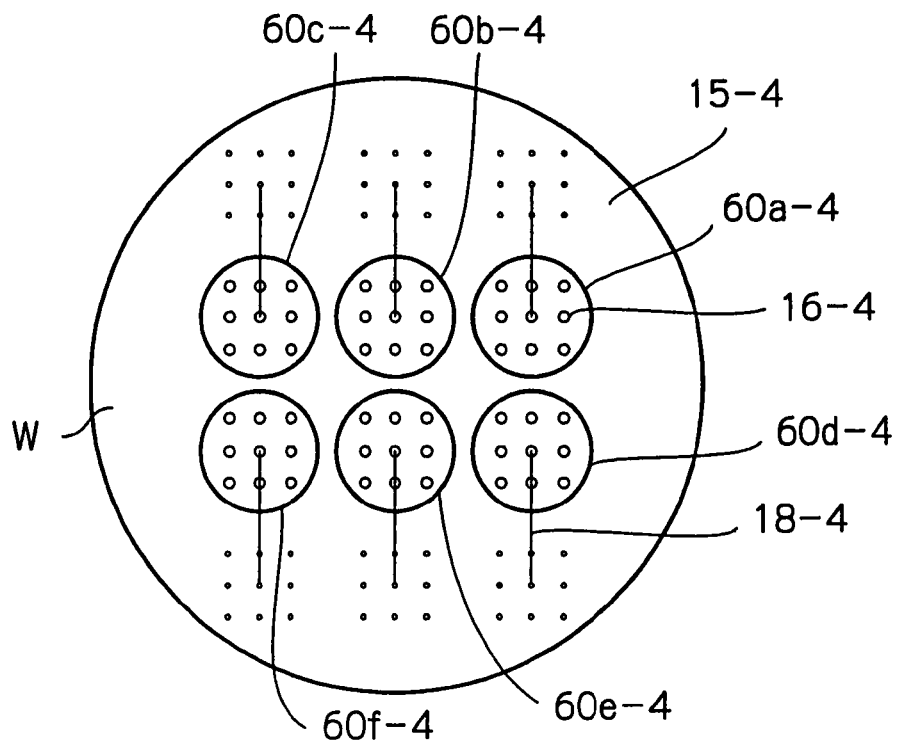
FIG. 29 shows a second placement configuration of multiple optical systems in the multiple column electron optical system of the present invention.

The electron beam optical apparatus of the second embodiment is related to a configuration in which multiple optical systems are arranged in a 2-row, m-column (m>1) pattern. FIG. 29 is a top view showing an example in which six optical systems are configured in a 2-row, 3-column pattern. The specific constituent elements of the electron optical system and the individual optical systems are substantially the same as in the first embodiment, and they are therefore assigned the same reference symbols here, they will not be described in detail.

In FIG. 29, the maximum diameters of the six optical systems of the primary electron beam irradiation system are indicated by the outlines **60*a*-4 through 60*f*-4. To prevent these multiple optical systems from interfering with each other, the optical axes 18-4** of the secondary optical systems (the paths of the secondary electron beams) are lined up in the row direction, pointing toward the outer edge of the wafer. The preferred number of columns (m) is around 3 or 4, but two columns, or four, may also be added, outside of these.

The multi-aperture regions 16-4 and the detector 15-4 are configured in a 3-row, 3-column array as the maximum number of beamlets and detector elements can be included in one optical system without encountering excessive aberration. The stage 48-4 is operated in a repeating series of step movements to move it within the horizontal plane. Scanning is performed the same way as in the first embodiment.

In this second embodiment, the number of optical systems (columns) is increased, and each optical system has more beamlets and detector elements, and it therefore further improves semiconductor wafer inspection process throughput.

(Effects of the Multiple Optical System (Column) Electron Optical System)

As described in detail above, provided according to the multiple optical system electron beam optical apparatus of the present invention, are a plurality of optical systems that are capable of performing irradiation of primary electrons and detection of secondary electrons separately, for inspecting different regions on the sample. This provides an excellent effect in that throughput can be greatly improved while maintaining high resolution.

Alignment of the Electron Optics of the Multibeam Inspection Apparatus

The axes of the optical systems of the multibeam inspection apparatus described above require alignment. The electron beam inspection apparatus of the present invention has an alignment system for this purpose. That system is described below.

(Primary Optical System Alignment)

Figure 33:
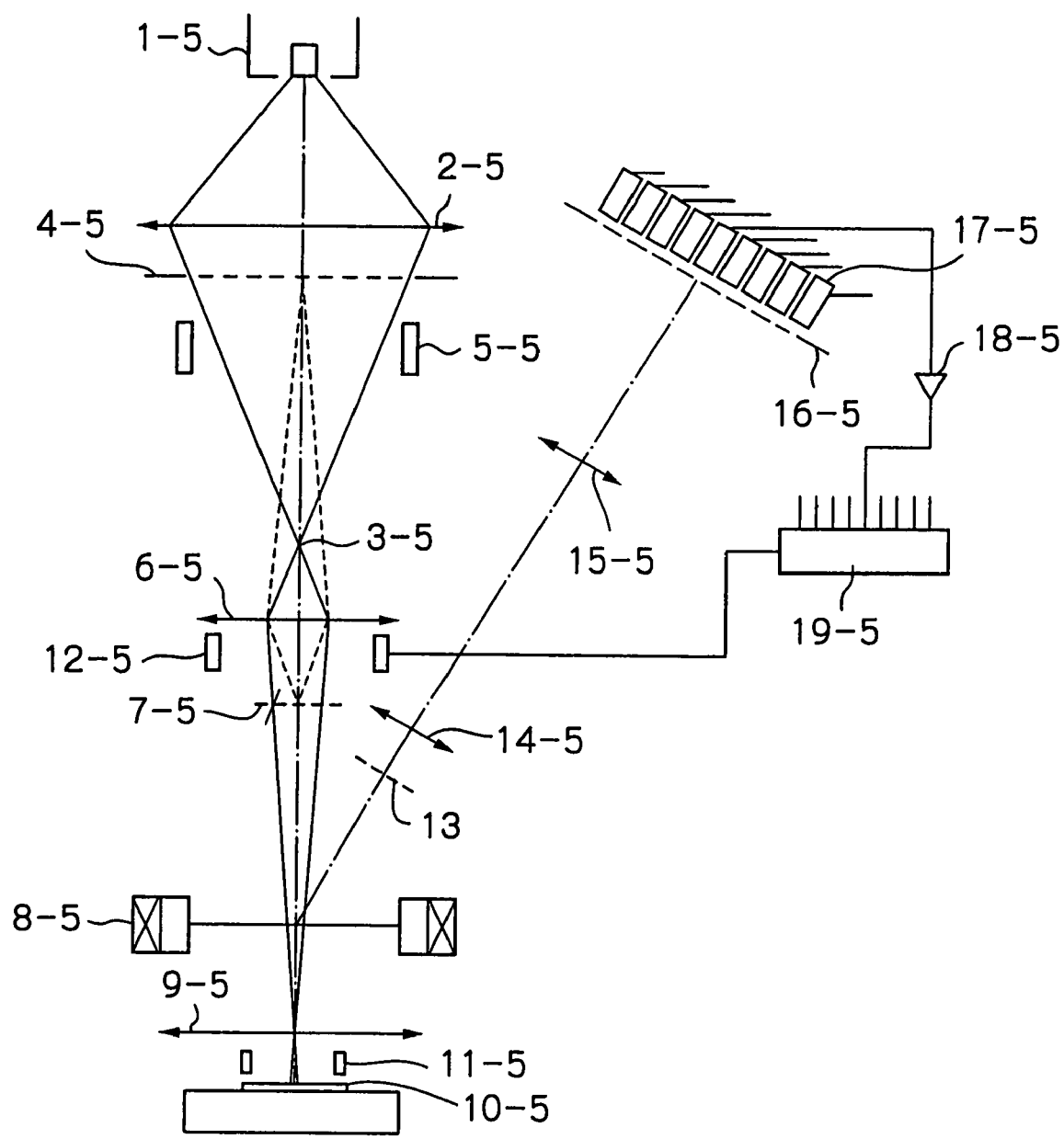
FIG. 33 is a drawing to aid the description of an electron optical system axial alignment method.

FIG. 33 shows an electron optical system that will be used to describe alignment according to the present invention. The configuration and operation of this system are essentially the same as in the multibeam inspection apparatus described above, and their descriptions will therefore not be repeated here.

As in the above systems, this electron optical system has a primary optical system comprising an electron gun 1-5; a condenser lens 2-5; a demagnification lens 6-5; two electrostatic deflectors 5-5 and 12-5; an axially symmetrical electrode 11-5; and an objective lens 9-5. It also has a secondary optical system comprising two magnification lenses 14-5 and 15-5. Alignment of the primary optical system will be described first. The alignment we will now be discussing consists of aligning the axis lines of the multibeam beamlets with the optical axis of the optical system.

Axial alignment of the lenses of the primary optical system (i.e., the axial alignment of the condenser lens 2-5, the demagnification lens 6-5, and objective lens 9-5) basically involves making adjustments so that the amount of movement of at least two of the beam positions on the surface of the sample caused by a small change in the excitation voltages of the lenses will be the same. Here, the two beams used for the alignment are equidistant from the multibeam center (for example, two beamlets positioned on a circle centered on the point indicated on the drawing).

Figure 34:
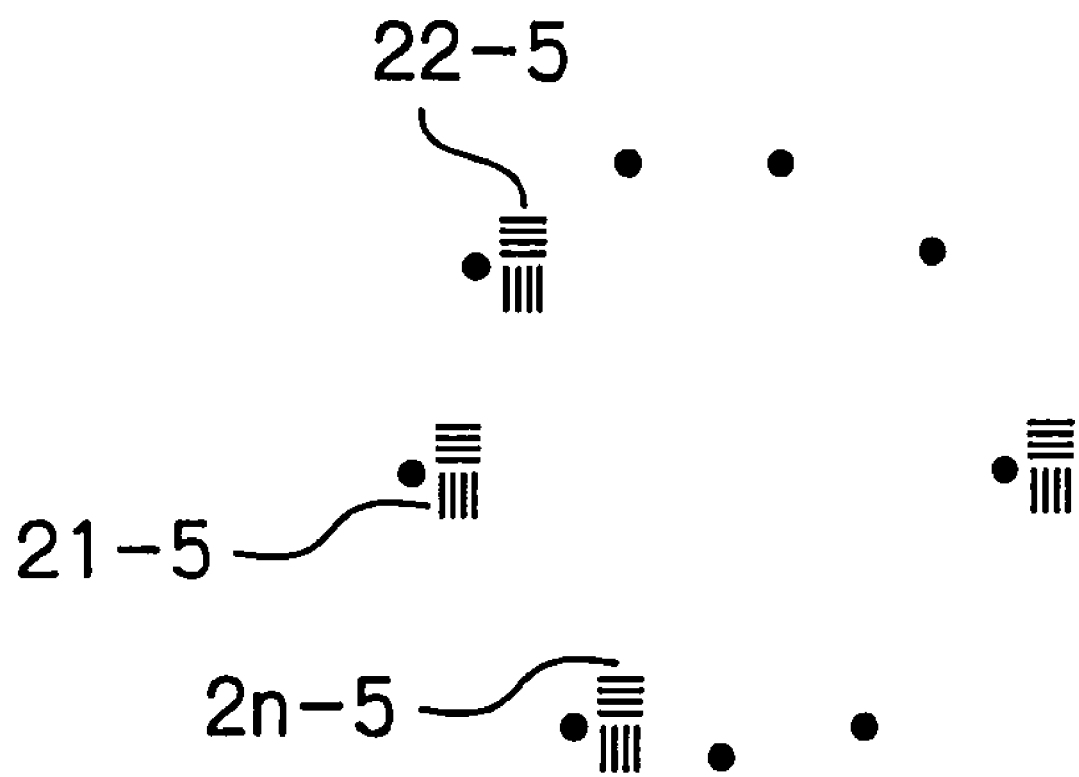
FIG. 34 shows alignment marks provided on a sample used in the alignment method of FIG. 33.

The axial alignment of the objective lens 9-5 can be performed as follows: First, as shown in FIG. 34, marks (21-5, 22-5, . . . 2n-5) made up of combinations of X-lines and Y-lines (indicating irradiation reference locations for each beamlet) are provided at locations on the surface of a sample 10-5 at which the multiple primary electron beamlets (indicated by the black dots) are imaged, and the beam focus conditions (the lens excitation voltages at which the beam is properly focussed) are measured for each mark. For these measurements, the signal contrast when multiple primary beamlets are scanned in the X direction, and the signal contrast when the beams are scanned in the Y direction are measured at a minimum of three objective lens excitation voltages, and the results plotted in a graph of change in contrast vs. excitation voltage. The convergence condition can then be determined from the graph obtained: For example, if $V_{ox}$ is the excitation voltage at which the contrast in the X direction is the greatest, and $V_{oy}$ is the excitation voltage at which the contrast in the Y direction is the greatest, then the convergence condition would be $(V_{ox}+V_{oy})/2$. The axially aligned condition for the objective lens 9-5 is then determined as the condition at which the least difference exists between the convergence conditions of at least two electron beamlets (e.g., two beamlets diametrically opposite each other on a circle centered on the optical axis). In other words, when the difference between convergence conditions is minimum, the beams will pass through the objective lens at points at which the difference in the distances, from the optical axis, of the two beams, is minimum.

Performing axial alignment of the multibeam electron optical system as described above makes it possible to use multiple electron beams to increase the throughput of various inspection processes (defect inspections, critical dimension checks, etc.) without sacrificing accuracy.

(Secondary Optical System Alignment)

Figure 35:
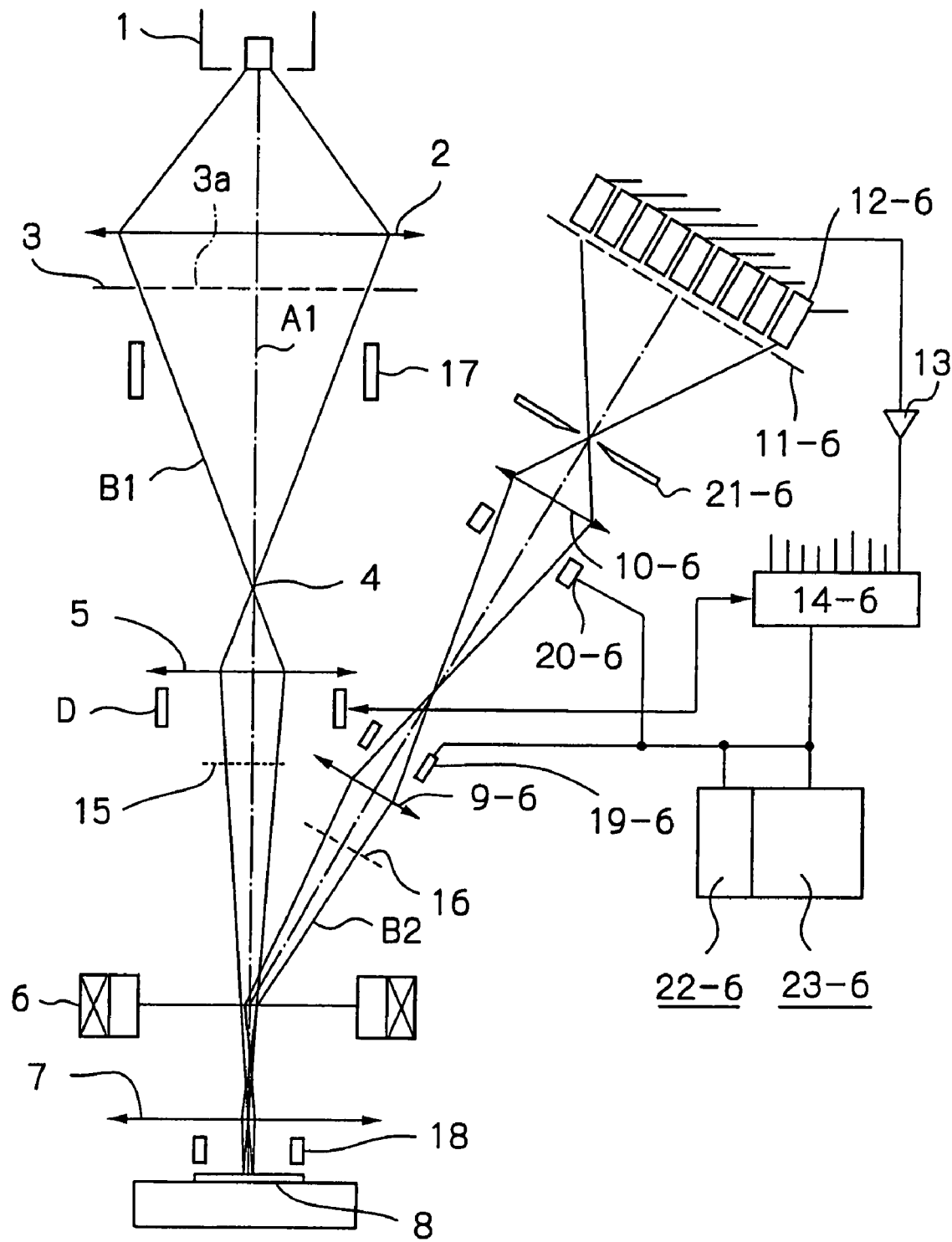
FIG. 35 is a diagram (of an electron optical system) to aid the description of the alignment of a secondary optical system.

Alignment of the secondary optical system will now be described. FIG. 35 shows the same kind of electron optical system as described above. As shown, the secondary optical system of this electron optical system comprises a first magnification lens 9-6, a second magnification lens 10-6, a multi-aperture plate 11-6, a detector 12-6, a first deflector 19-6, a second deflector 20-6, and a crossover aperture stop 21-6. The secondary optical system axial alignment described will be for the case in which this aperture stop 21-6 is placed at a crossover located between the second magnification lens 10-6 and the detection multi-aperture plate 11-6.

In the system of FIG. 35, the signal from a scan signal generator 22-6 is superimposed on a deflection signal from a deflection signal generator 23-6, and the resulting signal is applied to the two-stage deflector made up of the first deflector 19-6 and the second deflector 20-6. These two deflector stages 19-6 and 20-6, which are placed orthogonal to the optical axis, have two alignment modes: one mode in which they are axially aligned with the second magnification lens 10-6, and another mode in which they are axially aligned with the aperture stop 21-6. In the two modes, the signal strength ratio of the signals applied to the two deflectors (19-6 and 20-6) from the scan signal generator 22-6 and the deflection signal generator 23-6 are set to predetermined values for the alignment mode being used, and the deflectors 19-6 and 20-6 are then controlled according to this ratio. For example, to perform axial alignment with the second magnification lens 10-6, the deflector 19-6 output might be set to 1 and the deflector 20-6 output to -1.5; whereas for axial alignment with the aperture stop 21-6, the signal strength ratio would be determined such as to put the center of the principal plane of the second magnification lens 10-6 at the center of deflection.

Figure 36A:
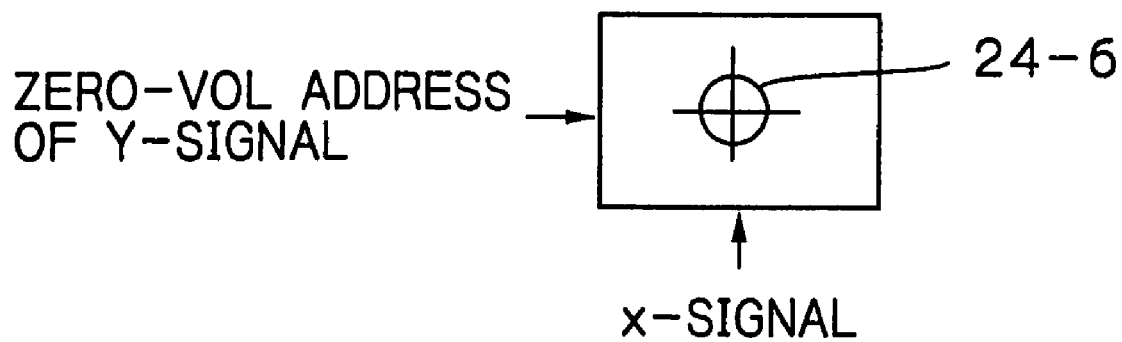
FIG. 36(a) shows the positional relationship between an aperture stop image and addresses at completion of axial alignment of an optical system.

The image processor 14-6 forms images in synchronization with the scanning of the electron beamlets over the aperture stop 21-6 by the deflectors 19-6 and 20-6. The scan signal is applied to the deflectors 19-6 and 20-6, and also to an image forming circuit in the image processor 14-6. When a signal from one of the elements of the multibeam detector 12-6 is applied to the image processor 14-6 as image data, of the detector element addresses corresponding to the scan signal of the image forming circuit of the image processor 14-6, the only addresses for which strong signals will be input to the image processor 14-6 from the detector 12-6 are those addresses that correspond to electron beams that have passed through the aperture stop 21-6. Thus when the axes are aligned, an aperture stop image 24-6 will be formed as shown in FIG. 36(a).

Figure 36B:
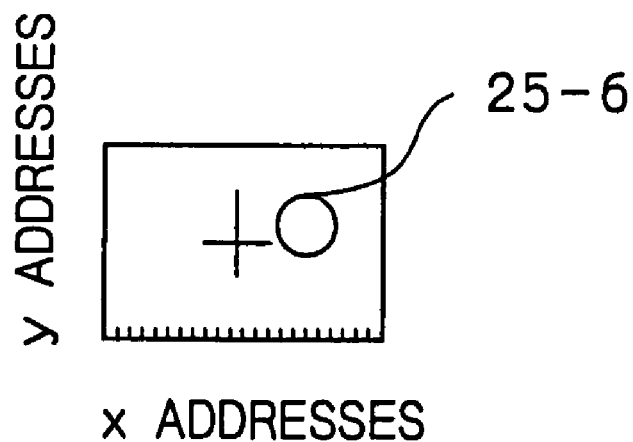
FIG. 36(b) shows the positional relationship between an aperture stop image and addresses during axial alignment of an optical system.

If the axes are misaligned, however, the signal aperture stop image 25-6 will be formed when the scan signal x,y address is strong-offset from the 0,0 location, as shown in FIG. 36(b). When this is the case, the outputs supplied to the deflectors 19-6 and 20-6 from the deflection signal generator 23-6 are changed as required to cause those deflectors to deflect the secondary electron beam B2 so that the aperture image coincides with the address at which the X and Y scan signals are both at 0 volts, as shown in FIG. 36(a). When this is accomplished, the axial alignment is complete. In other words, the beam now passes through the center of the aperture stop. In this configuration, the deflection signal generator 23-6 includes the deflection signal generating device, as well as a device for changing the output of the deflection signal generating device and supplying it to the deflectors. This alignment procedure can be performed automatically, entirely without human intervention.

In this electron optical system, the following effects can be brought to fruition by performing the axial alignment as described above:

Axial alignment with respect to the aperture stop can be performed automatically.

Because the deflectors used for normal beam scanning are also used for axial alignment, only half as many deflectors are required.

It makes it possible to perform axial alignment of a multi-beam system.

Because a secondary optical system aperture stop is provided between the ExB separator and the multibeam detector, the positioning of this stop can be determined independently of the primary optical system aperture stop.

(Axial Alignment of the Wien Filter/ExB Separator)

The ExB separator used in the electron optical system of the inspection apparatus described above is configured to form mutually orthogonal electric and magnetic fields in a plane perpendicular to the surface of the sample. The operation of the ExB separator is such that all electrons for which the relationships between the electric and magnetic fields and the energy and speed of the electrons satisfy a given set of conditions, are sent straight through the separator without being deflected; and all other electrons are deflected. Within the ExB separator structure, there exists a region in which the distribution of electric and magnetic fields is uniform; and a region in which it is not. Therefore in order to perform defect inspections with good accuracy using an electron beam inspection apparatus with multiple beamlets, the axis of each of those beamlets has to be aligned with the axis of the ExB separator. That is, the region of the ExB separator over which the distribution of electric and magnetic fields is uniform has to be determined, and adjustments made so that each of the electron beamlets passes through that region.

When an ExB separator is used in a multibeam electron beam inspection apparatus, however, the region, of the ExB separator, over which the electric and magnetic fields are uniform, and the region, of the ExB separator, through which the multiple beams pass, both encompass areas of about the same size. Therefore, if alignment of electron beamlets with the axis of the ExB separator is inadequate, some of the beamlets may fall outside of the region of uniform electric and magnetic field distribution. This can degrade the beam characteristics, resulting in greater distortion at the edge of the field, and increased blurring of the image.

The present invention provides a method for performing axial alignment of multiple beams with the ExB separator, for the purpose of eliminating the blurring and distortion of the image due to the use of an ExB separator in the multibeam electron beam inspection apparatus. Alignment of multiple beams with the axis of the ExB separator is described below.

Figure 37:
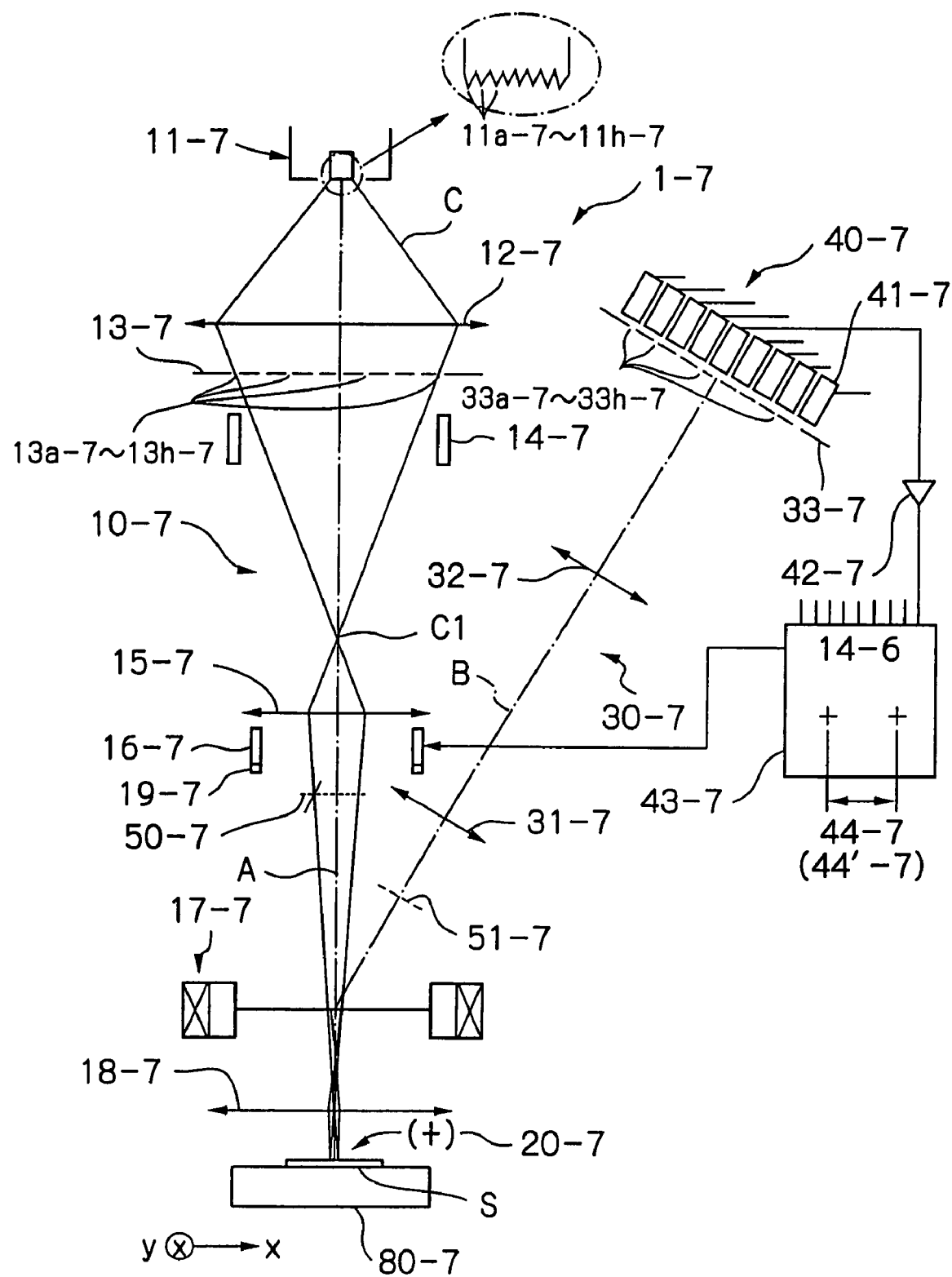
FIG. 37 shows the optical system of a typical electron beam apparatus. The drawing is provided to aid the description of axial alignment with the axis of a Wien filter (ExB separator) according to the present invention.

The optical system of the electron beam inspection apparatus 1 shown in FIG. 37 has essentially the same configuration as that of the inspection apparatus described above. It comprises a primary optical system 10-7, a secondary optical system 30-7, a detector 40-7, and an X-Y stage 80-7 for moving an inspection sample in the X and Y directions. A primary optical system 10-7, which is the optical system used to irradiate the surface of a sample (i.e., a wafer W), comprises an electron gun 11-7, for emitting an electron beam;
an electrostatic lens 12-7, for converging the electron beam emitted by the electron gun;
a first multi-aperture plate 13-7 having formed therein, a plurality of small openings (in this embodiment, 8 openings 13a-7 through 13h-7), arranged in a straight line);
an electrostatic deflector 14-7;
an electrostatic demagnification lens 15-7, for deflecting multiple beamlets that have passed through the first multi-aperture plate 13-7;
an electrostatic deflector 16-7 for deflecting the multiple beamlets;
an ExB separator 17-7;
an electrostatic objective lens 18-7; and
an axial alignment device 19-7 for performing axial alignment of the electron beams;

all of which, as shown in FIG. 37, are arranged in the above listed sequence with the electron gun 11-7 at the top, such that the optical axis A of the electron beam emitted by the electron gun is perpendicular to the surface of a sample S. Also, formed in a straight line on a cathode within the electron gun, are a plurality of pointed tips (in this embodiment, for example, 8 tips 11a-7 through 11h-7, as shown in FIG. 37).

The secondary optical axis 30-7 comprises
two electrostatic magnification lenses (31-7 and 32-7) placed along an optical axis B that slants away from the optical axis A near the ExB separator 17-7 of the primary optical system 10-7; and
a second multi-aperture plate 33-7 having a plurality of small openings (in this embodiment, 8 openings 33a-7 through 33h-7), formed therein such as to match the number and arrangement of the apertures of the first multi-aperture plate 13-7.

The detector 40-7 has a separate detector element 41-7 for each of the apertures of the second multi-aperture plate 33-7. Each of the detector elements 40-7 is connected through an amplifier 42-7 to an image processor 43-7. In addition, the same signal as that applied to the electrostatic deflector 16-7 is also applied to the image processor 43-7.

All of the above constituent elements of the system may be implemented using commonly known components, and their construction will therefore not be described in detail.

Next, the operation of an electron beam inspection apparatus 1-7 configured as indicated above will be described. Electron beams are emitted in 8 directions from the plurality of tips (11a-7 through 11h-7) on the cathode of the single electron gun 11-7. The emitted electron beam C is converged by the electrostatic lens 12-7, to form a crossover C1. The electron beam C that is converged by the electrostatic lens 12-7 irradiates the first multi-aperture plate 13-7, passing through a plurality of small apertures (apertures 13a-7 through 13h-7, formed in a straight line in the X direction, for example) in the first multi-aperture plate 13-7, to be formed thereby into 8 multibeam beamlets. These electron multibeam beamlets are demagnified by the electrostatic demagnification lens 15-7 and projected at positions indicated by the points 50-7. After being converged at the points 50-7, the beamlets are again converged at the sample W by the electrostatic objective lens 18-7. The multibeams leaving the first multi-aperture plate 13-7 are deflected by the electrostatic deflector 16-7 (placed between the electrostatic demagnification lens 15-7 and the electrostatic objective lens 18-7) such as to simultaneously scan the beamlets across the surface of the sample W.

Thus 8 spots on the sample W are irradiated by the 8 converged beamlets. Secondary electrons emitted from these 8 spots are attracted and narrowly converged into secondary electron beamlets by the electric field of the electrostatic objective lens 18-7. The converged secondary electron beamlets are then deflected by the ExB separator 17-7 to inject them into the secondary optical system. Secondary electron images are formed at the points 51-7, which are closer to the electrostatic objective lens 18-7 than are the points 50-7. The reason for this difference is that the energy of each secondary electron beamlet (only a few eV) is very small in comparison to the 500 eV energy possessed by each primary electron beamlet. The thus-imaged secondary electrons are propelled along the secondary optical axis B and injected into the electrostatic magnification lenses 31-7 and 32-7. The secondary electrons passed through these magnification lenses are imaged at the locations of the plurality of apertures (33a-7 through 33h-7) of the secondary multi-aperture plate 33-7. The electrons passed through these apertures are detected by corresponding detector elements 41-7 of the detector 40-7.

When this occurs, the secondary electrons emitted from the sample W by the electron beamlet that passed through the aperture 13a-7 of the first multi-aperture plate 13-7, pass through the aperture 33a-7 of the second multi-aperture plate 33-7; the secondary electrons emitted from the sample S by the electron beamlet that passed through the aperture 13b-7 of the first multi-aperture plate, pass through the aperture 33b-7 of the second multi-aperture plate 33-7; the secondary electrons emitted from the sample S by the electron beamlet that passed through the aperture 13c-7 of the first multi-aperture plate, pass through the aperture 33c-7 of the second multi-aperture plate 33-7, and so on. In other words, secondary electrons emitted from the surface of the sample by primary electron beamlets pass through apertures in the second multi-aperture plate 33-7 that correspond to respective apertures of the first multi-aperture plate 13-7, to be injected into the respective corresponding detector elements 41-7.

Each of the respective detector elements 41-7 converts its detected secondary electrons into an electrical signal representative of the secondary electron intensity. Each of these electrical signals output by the detector is then amplified by an amplifier 42-7, and input to the image processor 43-7, where it is converted to image data. The image processor 43-7 also receives the scan signal used to deflect the primary electron beams. Based on the information provided by the both the electron intensity and scan signals, the image processor 43-7 can create an image of the surface of the sample W. By then comparing this detected image with a reference standard pattern, defects on the surface of the sample W can be detected.

Thus in the above system, electron beamlets passed through the apertures of the first multi-aperture plate 13-7 are converged at the surface of the sample W, causing secondary electrons to be emitted from the sample W, and detected by the detector elements 41-7. In such a system it is especially important to minimize the effects of three types of aberration: distortion, field curvature aberration, and field astigmatism caused by the primary optical system.

The sample w is scanned in two dimensions by applying scan signals to the electrostatic deflector 16-7 and the magnetic field of the ExB separator 17-7, and a scanning electron microscope signal is displayed in the display of the image processor 43-7. A mark 20-7 (the + symbol in FIG. 37) is provided on the surface of the sample W This size of this mark 20-7 is 5 microns, while the mutual separation between the spots at which the 8 electron beamlets are imaged is on the order of 100 microns. Thus the mark 20-7 can be scanned with a single beamlet, and its image displayed by the image processor 43-7.

A method for performing axial alignment of the multiple electron beams will now be described. The axial alignment device 19-7 is used to align the electron beams with the axis of the ExB separator 17-7. First, the position of the X-Y stage 80-7 is determined such that, of the 8 electron beamlets, only the beamlet formed by the right-most aperture 13h-7 of the first multi-aperture plate 13-7 will scan the mark 20-7 on the sample. Then, scan signals are applied to the magnetic fields the electrostatic deflector 16-7 and the ExB separator 17-7 as required to two-dimensionally scan the mark 20-7. As the scan proceeds, the detector element 41-7 detects, and the image processor 43-7 displays, an image of the mark 20-7. During scanning, the voltage applied to the ExB separator 17-7 is periodically varied between a reference voltage and a voltage equal to the reference voltage+10 volts. The positional displacement magnitude 44-7 corresponds to the amount of deflection, of the beamlet passed through the aperture 13h-7, by the ExB separator 17-7 (due to the change in the deflection voltage applied thereto). The value of this positional displacement magnitude 44-7 is stored in memory.

Next, the position of the X-Y stage 80-7 is determined such that only the beamlet formed by the left-most aperture 13a-7 of the first multi-aperture plate 13-7 will scan the mark 20-7. The mark 20-7 is scanned, the result of the scan is detected by the detector element 41-7, and the mark 20-7 image is displayed by the image processor 43-7. The electron beamlet formed by the aperture 13a-7 is on the opposite side of the optical axis A of the primary optical system 10-7 from that of the above beamlet formed by the aperture 13h-7, and is separated from the optical axis A by the same distance. The locations of these two beamlets, then, are separated by the maximum possible distance. With the beamlets in this state, voltage applied to the ExB separator 17-7 is periodically varied between a reference value and a value equal to the reference value+10 volts. Here too, the image processor 43-7 displays the images of two marks separated from each other, this time by a positional displacement magnitude 44'-7. This positional displacement magnitude 44'-7 corresponds to the amount of deflection of the beamlet passed through the aperture 13a-7 by the ExB separator 17-7 (due to the change in the deflection voltage applied thereto). The value of this positional displacement magnitude 44'-7 is also stored in memory.

In addition, the voltage applied to the axial alignment device 19-7 is set to a number of different values, and for each new setting, the above operation with the beamlets that are passed through the apertures 13h-7 and 13a-7 is repeated, to obtain values of positional displacement 44-7 and 44'-7 for each voltage setting.

Then, the axial alignment device 19-7 voltage that yields the least difference between the values of positional displacement 44-7 and 44'-7 is determined, and the voltage is fixed at that value, thus completing the axial alignment for electron beamlets incident to the ExB separator. In this manner, multiple electron beamlets can be placed within that region of the ExB separator within which the magnetic and electric fields are uniform.

As a separate method for axial alignment of the multiple beamlets, instead of using beamlets arranged in a straight line, a plurality of beamlets (four in this embodiment) may be formed by providing a plurality of apertures (also four in this embodiment) in the first multi-aperture plate 13-7 and the second multi-aperture plate 33-7, respectively, at positions around and equidistant from, the optical axis A of the primary optical system, and the optical axis B of the secondary optical system, respectively. Because all four beamlets will then be separated from the optical axis A by the same distance, when the beams are properly aligned, a given change in the voltage applied to the ExB separator 17-7 should produce the same amount of positional displacement for each of the four beamlets. To accomplish this, an axial alignment operation must be performed individually for four of the eight beamlets.

As an alternative method, a mark may provided at each of the four points upon which the four beamlets are incident, the marks displayed on four monitors in the image processor 43-7, and the positional displacement values 44-7 and 44'-7 for all four beamlets measured at the same time.

Also, instead of using the image processor 43-7 to measure the positional displacement of the mark 20-7, the measurement may be performed automatically, and the alignment also performed by computer control. When this is done, however, better results will be obtained by using line-and-space patterns in the X and Y directions for the mark 20-7, rather than the + signs used above. In the electron beam inspection apparatus as described above, the following effects can be brought to fruition by performing the above axial alignment:

(1) The individual multibeam electron beamlets can be stably positioned within a region having uniform distribution of the electric and magnetic fields of the ExB separator, such that all beamlets can be tightly converged.

(2) If the individual multibeam beamlets are arranged in a straight line, a satisfactory axial alignment can be performed by aligning only two beamlets positioned symmetrically about the optical axis of the primary optical system.

(3) It is possible to determine whether there is sufficient margin within the region of uniform distribution of the electric and magnetic fields of the ExB separator to allow passage therethrough of all of the multibeam beamlets.

(4) Axial alignment of electron beamlets incident to the ExB separator can be performed in a wobbler-like operation in which symmetrical positions of the magnetic fields of the lenses are found, and the beamlets moved in the directions of these positions.

Alignment of Multibeam Beamlets with Multi-aperture Plates.

To obtain high brightness, the electron gun used in the multibeam system must emit a highly directive beam. To obtain sufficiently intense beamlets from a highly directive beam irradiating the multi-aperture plate, however, the large area of high beam intensity emitted from the electron gun must accurately overlay the aperture locations on the multi-aperture plate. Also, to efficiently evaluate the pattern of an inspection sample, the direction, on the sample surface, in which the multiple beamlets incident thereto are aligned, must be accurately aligned with the axis coordinates.

In light of the above, the present invention is configured to ensure that the high intensity region of the beam from the beam emission source incident to the multi-aperture plate, will be properly aligned with the aperture locations of the multi-aperture plate, and that the arrangement and orientation the multiple beamlets obtained therefrom will be accurately aligned with the orientation of the pattern on the surface of the sample.

Figure 38:
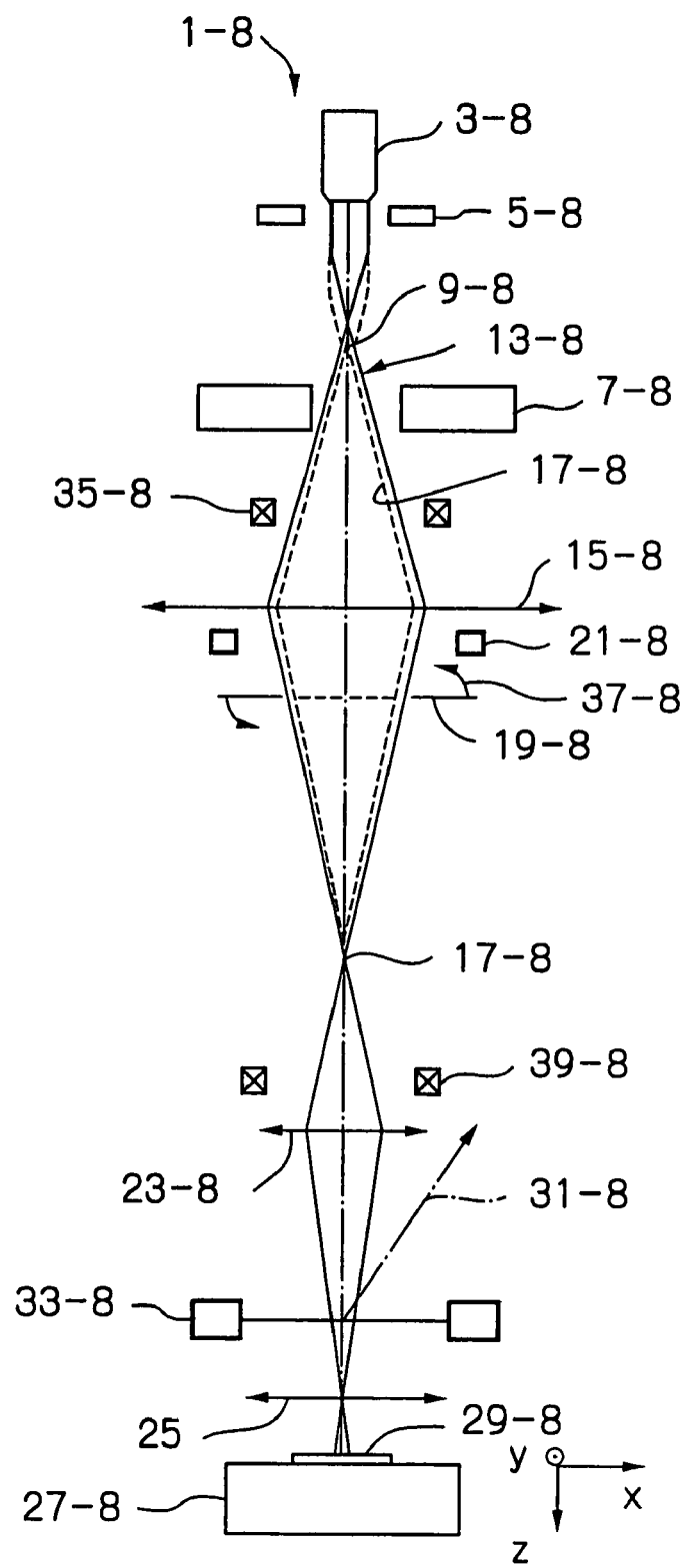
FIG. 38 is a schematic diagram of an example a main portion of an electron beam apparatus of the present invention.

An embodiment of this invention is described below. Shown in FIG. 38 is an electron gun 1-8. The electron gun 1-8 comprises a cathode 3-8, a Wehnelt electrode (beam converging electrode) 5-8, and an anode 7-8. The cathode 3-8 is made of monocrystalline $LaB_6$ formed in the shape of a truncated cone having a plurality of tips (i.e., beam-emitter tips, formed side by side along a circle on an end surface of the cathode facing the anode). When a negative bias voltage (negative with respect to the cathode) applied to the Wehnelt electrode 5-8 is increased (made more negative), a beam crossover 9-8 formed by the electron gun is shifted nearer the cathode, and the path of the beams emitted from the beam-emitter tips arranged along a circle on an end surface of the cathode shift away from the path 11-8 (indicated by the dotted line in the drawing), toward the path 13-8 indicated by the solid line. Conversely, if the negative bias voltage on the Wehnelt electrode 5-8 is decreased (made less negative), the beam path shifts away from the solid line, and toward the dotted line.

Figure 39:
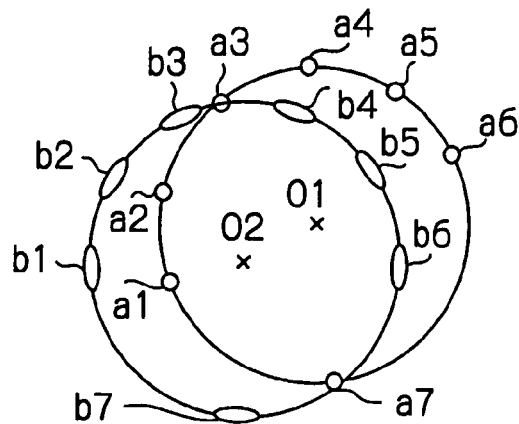
FIG. 39 shows the correspondence relationships between the electron beamlets and the apertures of the multi-aperture plate of the apparatus of FIG. 38 prior to adjustment.

After emerging from the normally grounded anode 7-8, the beam is converged by a condenser lens 15-8 to form a crossover 17-8. Provided on the electron gun side of the crossover 17-8 is a multi-aperture plate 19-8 having multiple apertures therein for shaping the irradiating beam into multibeam beamlets. When the multi-aperture plate 19-8 is irradiated with beams from the electron gun 1-8, the center O1 of the multi-aperture plate, and a point O2 central to all of the beamlets incident thereto, are axially aligned by an axial alignment coil 21-8. That is, if the center O1 of the multi-aperture plate and the point O2 central to all of the beams incident thereto are misaligned as shown in FIG. 39, then the small apertures a1-a7 of the multi-aperture plate 19-8 will not be properly aligned with the large regions of high beam intensity b1-b7 of the beams irradiating the multi-aperture plate. Consequently, there will be differences in beam intensity between the multibeam beamlets emerging from the multi-aperture plate 19-8. Therefore, the axial alignment coil 21-8 is used to parallel-shift all of the beams as required to adjust the point O2 (which is central to all of the beams incident to the multi-aperture plate 19-8) into alignment with the center O1 of the multi-aperture plate, such that the beamlets emerging from the apertures a1-a7 of the multi-aperture plate will all be of uniform beam intensity.

Figure 40:
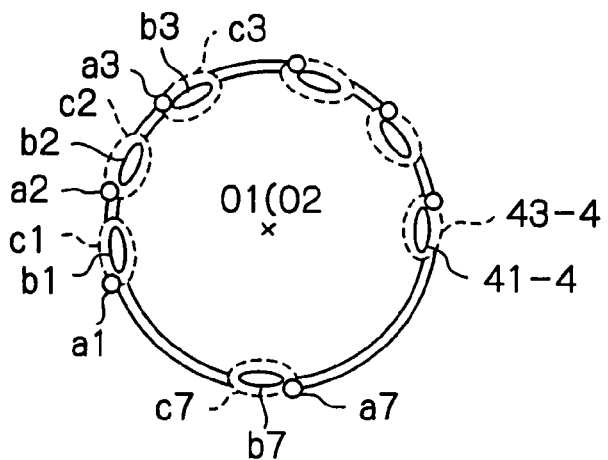
FIG. 40 shows the correspondence relationships between the electron beamlets and the apertures of the multi-aperture plate of the apparatus of FIG. 38 after axial alignment.
Figure 41:
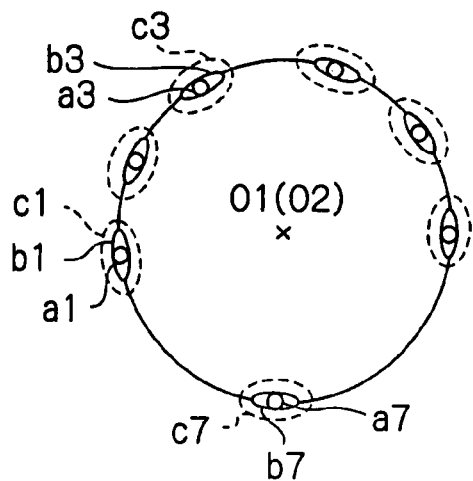
FIG. 41 shows the correspondence relationships between the electron beamlets and the apertures of the multi-aperture plate of the apparatus of FIG. 38 after adjustment according to the present invention.

FIG. 40 shows the relationships between the multibeam beamlets that have undergone the above alignment adjustment by the alignment coil 21-8, and the corresponding apertures of the multi-aperture plate. As can be seen from this drawing, it is not enough to simply align the point O2 central to all of the beams incident to the multi-aperture plate 19-8 with the center O1 of the multi-aperture plate. In the state shown in FIG. 40, for example, the high beam intensity regions b1-b7 (regions of high beam intensity of the beams incident to the multi-aperture plate) are not properly aligned with the aperture positions a1-a7 of the multi-aperture plate 19-8, and it is apparent that the alignment at this point is inadequate. That is, there is radial displacement 41-4, and an azimuth displacement 43-4 between the apertures a1-a7 of the multi-aperture plate and the high-beam-intensity regions b1-b7, which in some cases aligns the apertures with regions of not-so-high beam intensity c1-c7b of the beams incident to the multi-aperture plate. Therefore, the present invention has provisions for making fine adjustments in the radial and azimuth directions as required to properly align regions of high beam intensity b1-b7 with the apertures a1-a7 of the multi-aperture plate.

Radial displacement can be corrected by adjusting the bias voltage applied to the Wehnelt electrode 5-8. That is, the high-beam-intensity-regions b1-b7 can be moved radially outward by increasing the negative voltage applied to the Wehnelt 5-8; or radially inward by decreasing this negative voltage. The above adjustment procedure applies for the example shown in the drawings, in which the electron gun 1-8 forms the crossover 9-8. When the electron gun does not form a crossover, however, and instead forms a single diverging beam, reducing the negative bias voltage applied to the Wehnelt 5-8 will move the high-intensity-beam-regions radially outward, while increasing this bias moves them radially inward. In this manner it is possible to make adjustments to radially align the high-beam-intensity-regions b1-b7 of the beams incident to the multi-aperture plate 19-8 with the apertures a1-a7 of the multi-aperture plate.

Adjustment of the alignment in azimuth can be done in two different ways: One way is to use a rotation lens 35-8 provided between the electron gun 1-8 and the multi-aperture plate 19-8 to perform rotation about the optical axis of the multiple beams incident to the multi-aperture plate 19-8. The other way is to provide a rotation mechanism 37-8 on the multi-aperture plate 19-8 for rotating the multi-aperture plate 19-8 about the optical axis. In this manner it is possible to make adjustments to align, azimuth-wise, the high-beam-intensity-regions b1-b7 of the beams incident to the multi-aperture plate 19-8 with the apertures a1-a7 of the multi-aperture plate.

Also, by providing a rotation lens 39-8 between the multi-aperture plate 19-8 and the sample 29-8, and using it to adjust the multibeam beamlets emerging from the multi-aperture plate 19-8 in rotation about the optical axis, the orientation of the beamlet array on the surface of the sample can be accurately aligned with one of the coordinate axes (e.g. the x coordinates) of the sample, thus enabling more efficient scanning of the surface of the sample.

Also, provided below the demagnification lens 23-8 are deflectors for scanning the surface of the sample. Alignment of the directions of deflection of these deflectors with a coordinate axis of the sample is performed separately. If the rotation lens 39-8 were to be provided below these deflectors, this would shift their directions of deflection; so this rotation lens should be provided above the demagnification lens 23-8.

Also, the example shown in the drawings uses a rotation lens 35-8 provided between the electron gun 1-8 and the multi-aperture plate 19-8; a rotation lens 39-8 provided between the multi-aperture plate 19-8 and the sample 29-8; and in addition, a rotation mechanism 37-8 for rotating the multi-aperture plate 19-8 about the optical axis. However, when it comes to adjusting the states of the high-beam-intensity-regions b1-b7 of the beams incident to the multi-aperture plate 19-8, the positions of the apertures a1-a7 of the multi-aperture plate, and the orientation of the beamlet array on the surface of the sample, where appropriate, the functions of the rotation lenses 35-8 and 35-9 and the rotation mechanism 37-8 may be combined.

From the above, the following operational effects can be obtained:

(1) The radial positions of the high intensity beams generated by the electron gun can be aligned with the radial positions of the apertures of the multi-aperture plate, to thus obtain high intensity multi-beam beamlets.
(2) The azimuth positions of the high-beam-intensity regions in rotation about the optical axis can be aligned with the azimuth positions of the apertures of the multi-aperture plate, to thus obtain high intensity multi-beam beamlets.
(3) The orientation of the multibeam beamlet array can be accurately aligned with the coordinate axes of the surface of the sample, to thus enable more accurate evaluations to be performed.

Misalignment between the Secondary Electron Beam Image and a Standard Image

In the inspection apparatus considered up to this point, the possibility existed for positional displacement to arise between a secondary electron beam image acquired by irradiating, with a primary electron beam, a region to be inspected on a sample, and a standard image prepared in advance, thus degrading the defect detection accuracy of the apparatus.

This positional displacement between the detected and standard images became an especially large problem when the scan region of the primary electron beam was sufficiently shifted with respect to the wafer to cause a portion of the inspected pattern to fall outside of the detected images of secondary electron beams. Moreover, this was a problem that could not be solved by technology that simply optimized the matching region within the detected image. This could be a fatal weakness, especially for inspection of high precision patterns.

To address the above problem, the present invention is configured to prevent degradation of defect detection accuracy due to positional displacement between the detected image and the standard image. An embodiment of this aspect of the invention is described below.

Figure 42:
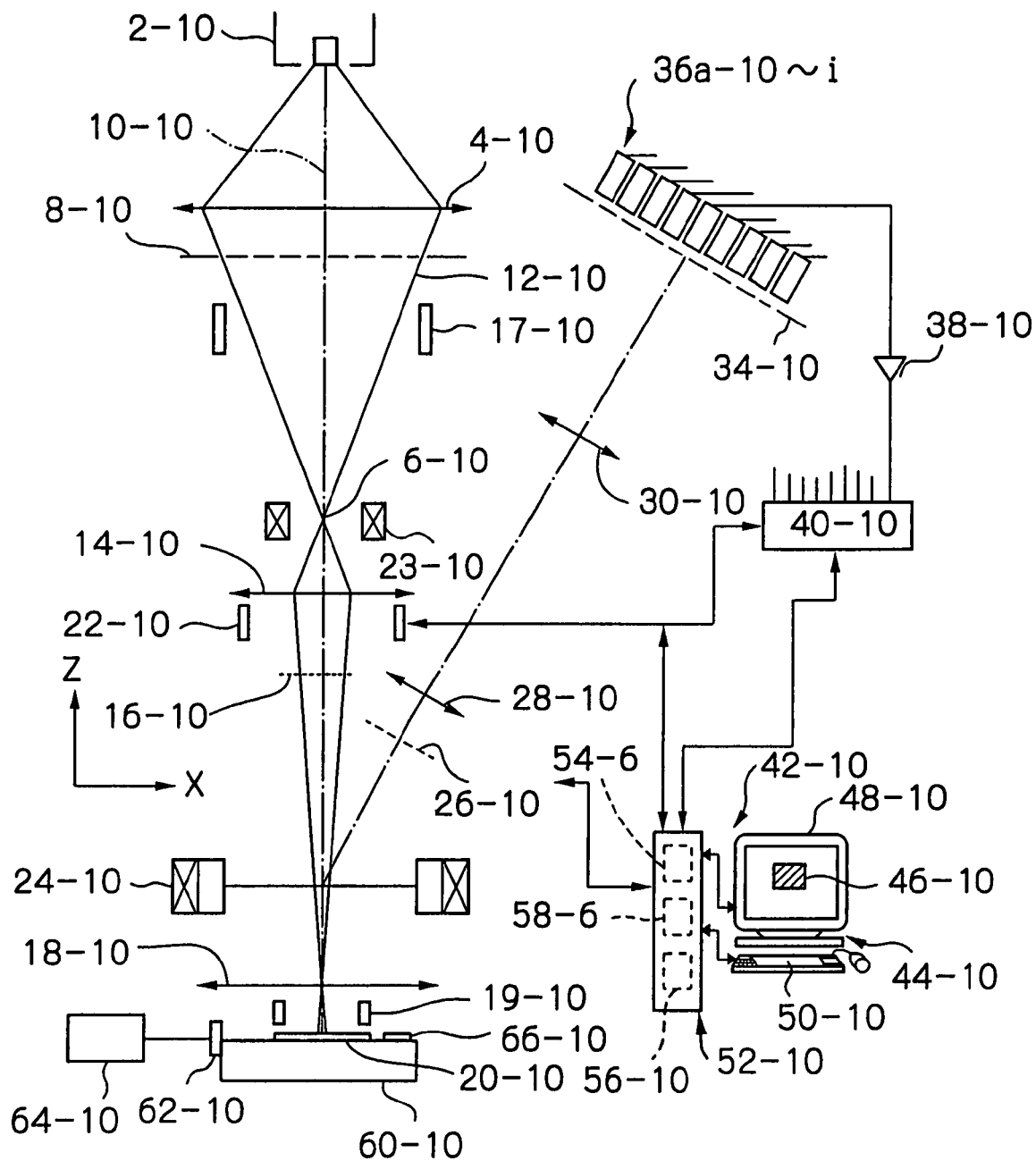
FIG. 42 is a schematic diagram of a defect inspection apparatus configuration according to the present invention, comprising a system for preventing positional displacement between a reference standard image and an image to be inspected. The diagram is also used to describe calibration of the electron beam inspection apparatus with respect to deviation between an actual irradiated point and a design point, according to the present invention.
Figure 43:
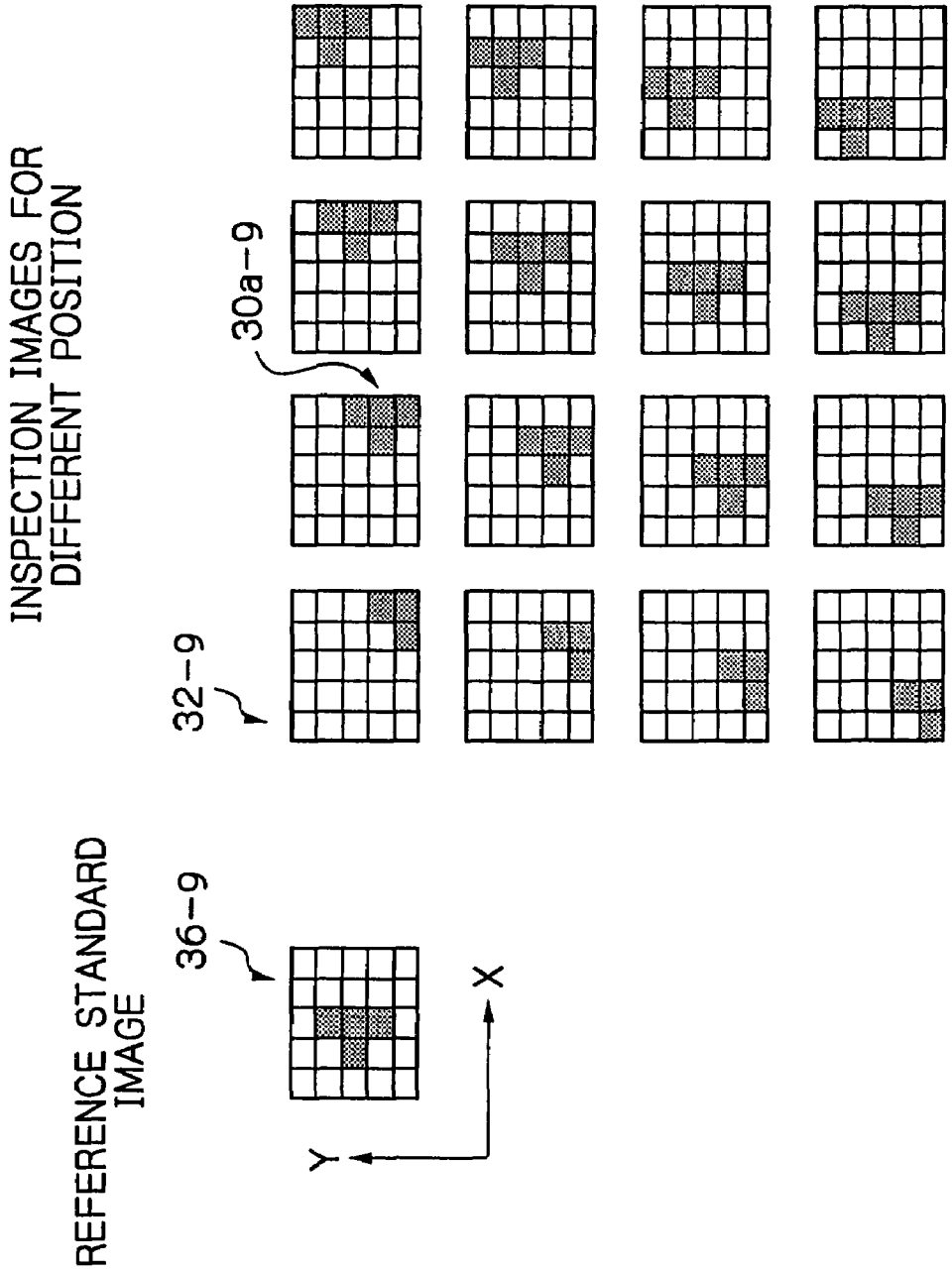
FIG. 43 shows an example of multiple inspection images acquired by the defect inspection apparatus of FIG. 42, and a reference standard image.

FIG. 42 shows a schematic representation of the configuration of the defect inspection apparatus of the present invention. This defect inspection apparatus comprises an electron gun 2-10, for emitting primary electron beam;
an electrostatic lens 8-10, for converging and shaping the emitted primary electron beam;
a multi-aperture plate 12-10;
an ExB deflector 24-10, for directing the shaped primary electron beam substantially perpendicularly incident to a semiconductor wafer W;
an objective lens 18-10, for forming a primary electron beam image at the surface of the wafer W;
a stage 60-10, provided in a sample chamber (not shown) capable of being evacuated to a vacuum state, said stage being configured to be movable within a horizontal plane with a wafer W loaded thereon;
electrostatic lenses (28-10 and 30-10) for guiding a secondary electron beam emitted from the surface of the wafer W to a secondary electron detector 36-10;
a detector 36-10 for detecting the guided secondary electrons; and
a controller 42-10 for controlling the entire apparatus, as well as an image forming circuit 40-6 for forming a detected image based on a secondary electron signal detected by the detector 36-10, and executing a process for detecting defects on the wafer W based on that image.

Figure 47:
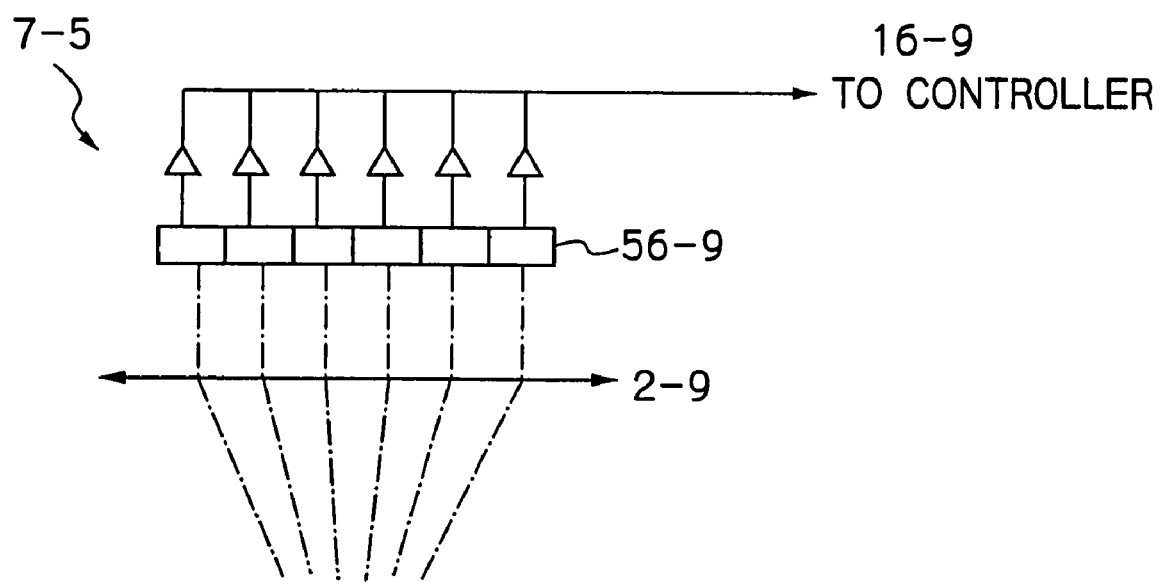
FIG. 47 shows an example of a specific configuration for the detector of the defect inspection apparatus of FIG. 42.

The detector 36-10 receives the secondary electrons collected by the electrostatic lenses 28-10 and 30-10 and coverts them to electrical signals. As shown in detail in FIG. 47, for example, the detector 36-10 has the same number of detector elements as there are multibeam beamlets, and outputs the same number of secondary electron signals in parallel to the image forming circuit 40-10. The two-dimensional images formed by the image forming circuit 40-10 are transferred to the controller 42-10.

The controller 42-10 may be a general-use personal computer (or workstation), as shown in FIG. 42 (or may be implemented in dedicated hardware as part of the defect detection apparatus). The controller 42-10, as shown in FIG. 42, comprises a main control unit 52-10 for executing various control and computation processes in accordance with a prescribed program;
a monitor 48-10 for displaying the results of processes executed by the main control unit 52-10; and
an input device 50-10 (such as a keyboard or mouse) for inputting commands entered by an operator.

The main control unit 52-10 comprises various circuit boards not shown in the drawing (CPU RAM, ROM, hard disk, video board, etc.). Within computer memory (RAM or hard disk), a secondary electron image memory area 54-6 is allocated for storage of digital image data (secondary electron images of a wafer W formed from electrical signals received from the detector 36-10).

Included on the hard disk is a reference standard image memory 56-10, for storage, in advance, of reference standard images of wafers (wafers with no defects). Also stored on the hard disk, in addition to a control program for controlling the overall defect inspection apparatus, is a defect detection program 58-6 for reading secondary electron image data from the memory area 54-6, and automatically detecting defects on a wafer W, based on that image data, in accordance with prescribed algorithms. This defect detection program 58-6 (later to be described in detail) has functions for performing a matching process to compare the actual detected secondary electron beam image with a reference standard image read from the reference standard image memory 56-10; for automatically detecting defects; and for displaying a warning to alert an operator when defects are detected. At this time, a secondary electron image 46-10 may also be displayed on the monitor 48-10.

Figure 44:
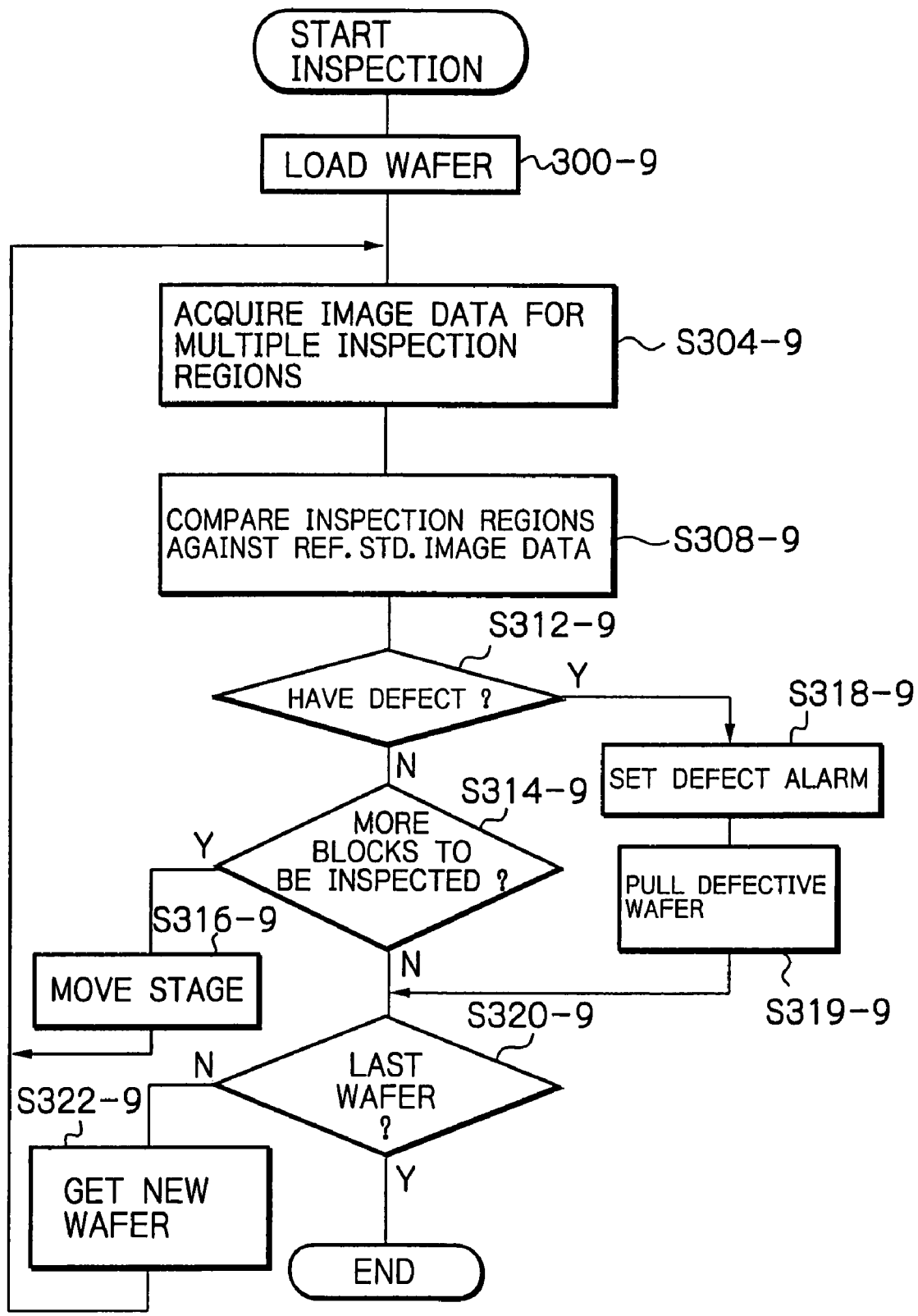
FIG. 44 is a flow chart for a main routine for performing inspection of wafers using the defect inspection apparatus of FIG. 42.

Next, the an example of the operation of the above defect inspection apparatus will be described with reference to the flow charts of FIGS. 44-46. First, in the main routine flow, as shown in FIG. 44, the sample (wafer W) is loaded on the stage 60-10 (Step 300-9). This loading may be accomplished in a mode wherein a loader (not shown) capable of holding a large number of wafers W, automatically loads wafers on the stage 60-10, one wafer at a time.

Next, images are acquired (Step 304-9) for each of multiple inspection regions that are partially overlapping but offset position-wise with respect to each other in the XY plane of the wafer W. These multiple inspection regions for which images are to be acquired might be, for example, rectangular regions on the wafer inspection surface 34-9 such as those indicated by the reference numbers 32a-9, 32b-9, . . . 32k-9, etc., in FIG. 48, where the different regions are displaced from each other position-wise around a wafer inspection pattern 30-9 yet remain partially overlapped. For example, in this step, inspection images 32-9 might be acquired for 16 different inspection regions, as shown in FIG. 42. Each small rectangular grid box within each of these 16 images corresponds to 1 pixel. However, a 'block' (an area larger than a pixel) may also be defined as the unit. The shaded grid boxes correspond to the image of the pattern on the wafer W. A detailed flow diagram for this step (Step 304-9), to be discussed later, is shown in FIG. 45.

Next, image data for each of the inspection regions acquired in Step 34-9 is compared with the corresponding reference standard image data stored in the secondary electron image memory area 54-6 (Step 308-9 of FIG. 3), and a decision is made as to whether defects exist in the inspection areas of the wafer covered by the above inspection regions (Step 312-9). This step involves a byte-for-byte image data matching process to be described in detail later based on the process flow diagram of FIG. 46.

If a YES decision is made in Step 312-9, based on the results of the comparison check made in Step 308-9 (i.e., if a decision is made that a defect does exist in the inspection areas of the wafer surface covered by the above inspection regions) a defect warning notice is output to alert the operator (Step 318-9). This may be done, for example, by displaying an appropriate message on the monitor 48-10. An enlarged view of the defective pattern (46-10) may be displayed at the same time. The defective wafer may also be immediately removed from the sample chamber 3-9 and stored in a separate location from where defect-free wafers are stored (Step 319-9).

If a NO decision is made in Step 312-9, based on the results of the comparison check made in Step 308-9 (i.e., if no defects exist in the currently inspected portion of the wafer W), a decision is made as to whether there are any inspection regions in the current sample that still remain to be inspected (Step 314-9). If there are such regions (YES at Step 314-9), drive is applied to the stage 60-10 to position the next inspection region of the wafer W under the irradiation region of the primary electron beam (Step 316-9). Execution then returns to Step 302-9, to repeat the process for the next region.

If there are no more regions left to inspect on the current wafer (NO in Step 314-9), or if execution has proceeded past the 'pull defective wafer' step (Step 319-9), execution then proceeds to Step 320-9. In this step, a decision is made as to whether the current sample (the wafer W), is the last one left to be inspected; i.e., whether there are any un-inspected wafers left in the loader (not shown). If the answer in Step 320-9 is NO (this is not the last wafer), the wafer just inspected is stored in its proper location, and a new wafer takes its place on the stage 60-10 (Step 322-9). Execution then returns to Step 302-9, and the same inspection process is repeated for the new wafer. If the answer in Step 320-9 is YES (this is the last wafer.), the last inspected wafer is stored in its proper location, and the process ends.

Next the process flow for Step 304-9 will be described with reference to the flow diagram of FIG. 45. First, the image number 'i' is set to an initial value of '1' (Step 330-9). The image number is an identification number assigned to the image of each inspection region, in the sequence in which those regions are to be inspected. Next, the system determines an image index position $(X_i,Y_i)$ for the region of the image number i just set (Step 332-9). The image index position defines the coordinates of a specific point within the inspection region (e.g., its center) that is to be used to demarcate the region. At the current point in the inspection process, i=1, the image index position is designated $(X_1,Y_1)$, which corresponds, for example, to the center position of the inspection region 32a-9 shown in FIG. 7. Image index positions are determined in advance for all of the inspection image regions, and saved, for example on the hard disk of the controller 16-9, to be read-out in Step 332-9.

Figure 45:
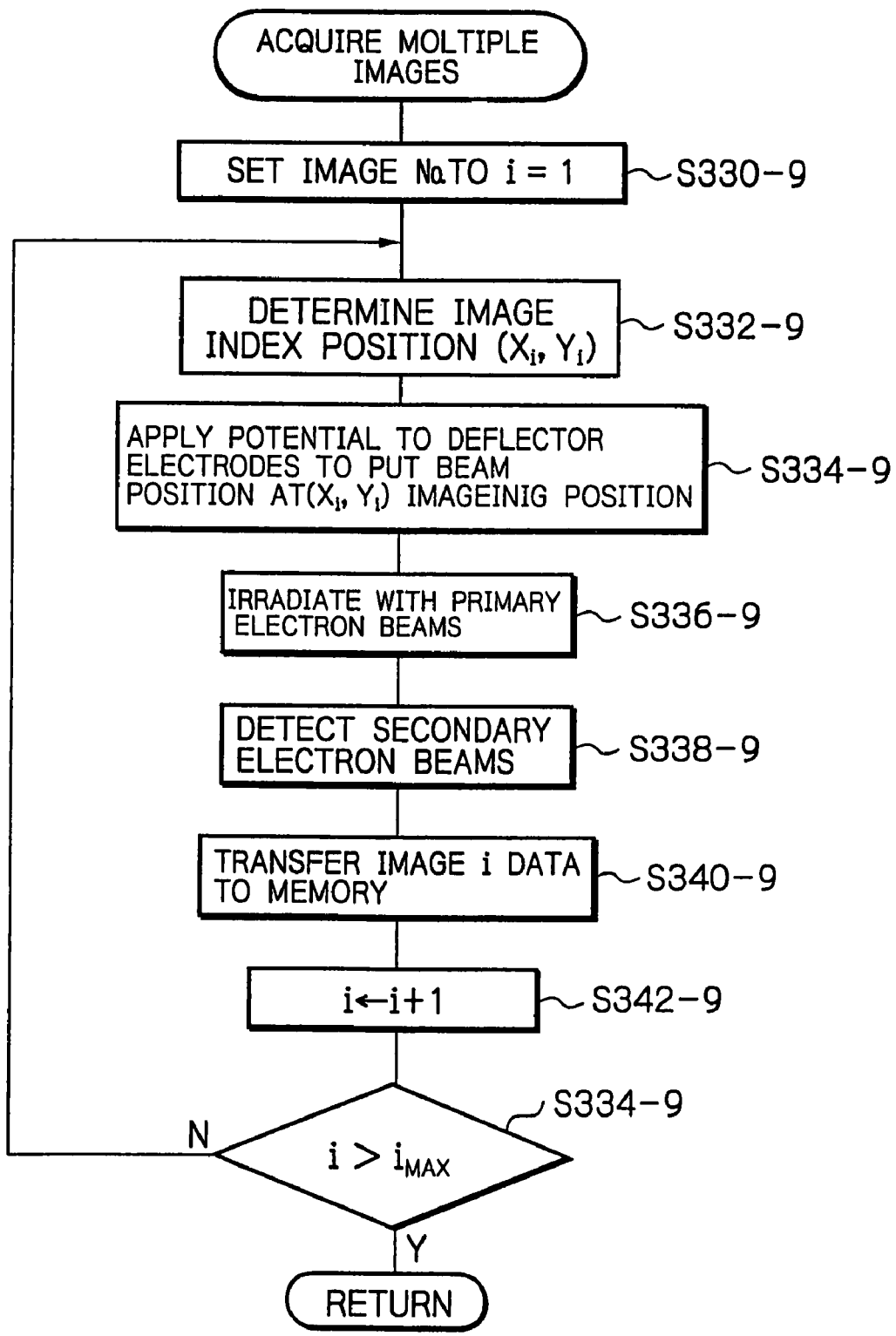
FIG. 45 is a detailed subroutine flow diagram for the step of acquiring data for multiple inspection images (Step 304-9) in the main routine of FIG. 44.

Next, in Step 334-9 of FIG. 45, a deflection control function of the controller 42-10 applies electrical potentials to the deflection poles 22-10 and 24-10 as required to properly deflect the primary electron beam passing through the objective lens 18-10 of FIG. 42 for irradiating the inspection image region having the image index position $(X_1,Y_1)$, as determined in Step 332-9.

Figure 48:
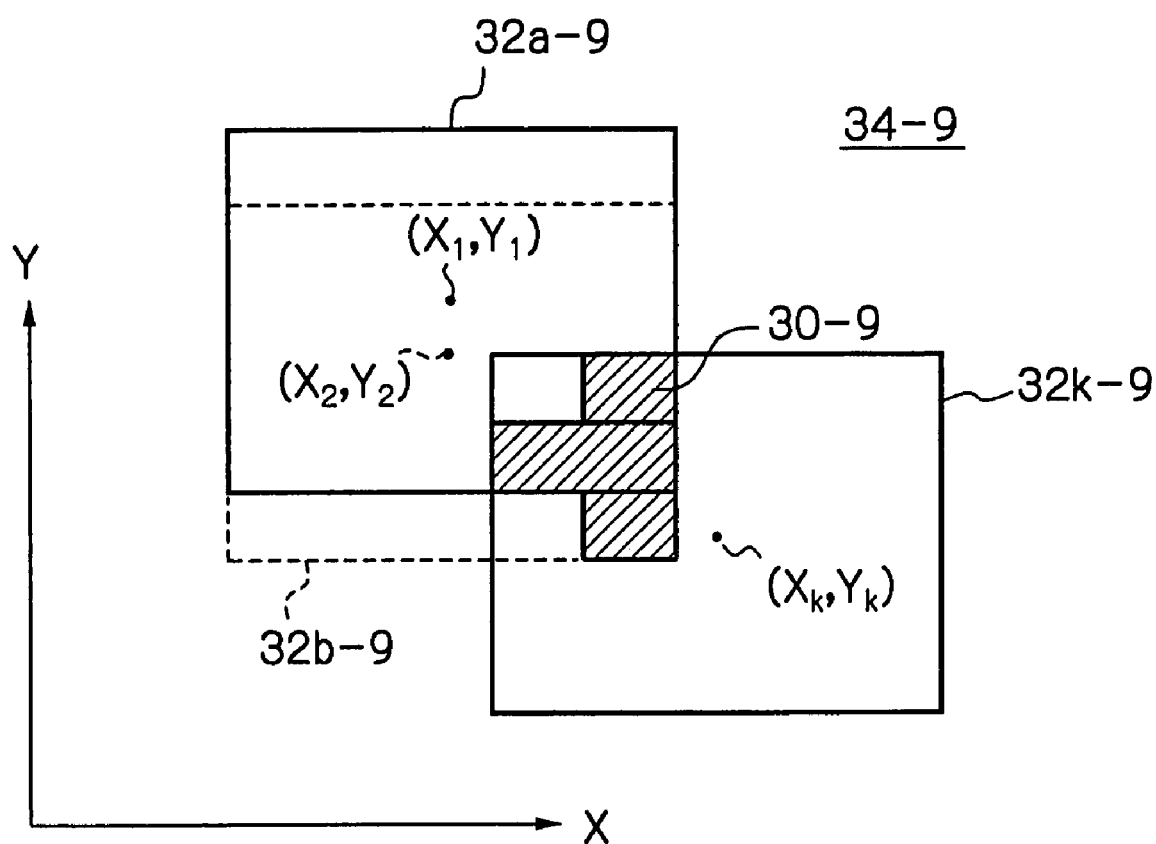
FIG. 48 is a drawing to illustrate a concept wherein the positions of multiple inspection regions on the surface of a semiconductor wafer are shifted such that they are offset from each other in position, but partially overlap.

Next, primary electron beams are emitted from the electron gun 2-10. These beams pass through the electrostatic lenses 4-6 and 14-10, the ExB deflector 24-10, the objective lens 18-10, and the deflection poles 22-10 and 24-10, to irradiate the surface of the loaded wafer W (Step 336-9). To perform this irradiation, the primary electron beams are deflected by the electrical fields created by the deflectors 22-10 and 14-10 as required to scan the entire inspection image region demarcated by the image index position $(X_1,Y_1)$ of the wafer inspection surface 34-9 (FIG. 48). In this example, when the image number i is equal to 1, the inspection region is 32a-9.

Secondary electron beams are emitted from the wafer surface in the inspection region irradiated by the primary electron beams. These secondary electron beams are imaged on the detector 36-10 by the electrostatic lenses 28-10 and 30-10. The detector 36-10 detects the converged secondary electron beams and outputs an electrical signal for each of its detector elements. These detector output signals are then converted to digital image data and output by the image-forming circuit 40-6(Step 338-9). The digital image data for the detected image number i is then transferred to the secondary electron image memory area 54-6 (Step 340-9).

In Step 342-9, the image number i is incremented by 1, and the resulting image number (i+1) is checked to determine whether it exceeds a given value $i_{max}$ (Step 344-9). This value $i_{max}$ is the total number of inspection images to be acquired, or '16' in the example of FIG. 42.

If a NO decision is made in Step 344-9 (if the image number i does not exceed the set value $i_{max}$), execution returns to Step 332-9, and the image index position for the incremented image number (i+1), i.e., $(X_{i+1},Y_{i+1})$ is determined. This image index position is at a location displaced from the image index position $(X_i,Y_i)$, determined in the preceding routine, by a prescribed distance in the X and/or Y directions $(\Delta X_i, \Delta Y_i)$. In the example of FIG. 7, the next image index position is shifted from the coordinates $(X_1,Y_1)$, in the Y direction only, to the point having the coordinates $(X_2,Y_y)$, where the inspection region then becomes the rectangular region 32b-9, as indicated by the dotted lines in the drawing. The value to use for $(\Delta X_i, \Delta Y_i,$ where i=1, 2, ..., $i_{max})$ can best be determined from empirical data on how far from the field of the detector 36-10 the pattern 30-9 of the wafer inspection surface 34-9 actually shifts, the number of regions to be inspected, and the surface area.

Steps 332-9 through 342-9 are repeated, in sequence, $i_{max}$ times (as many times as there are regions to be inspected). On the wafer inspection surface 34-9, as shown in FIG. 7, the location of these inspection regions is repeatedly shifted such that the different regions partially overlap, until the image index position becomes $(X_k,Y_k)$, (the index position after the inspection region has been changed k times), where the inspection region image becomes 32k-9.

In this manner, image data is acquired for each of the 16 inspection regions in the example of FIG. 42, and the data are stored in the memory 8-9. Thus as can be understood from FIG. 42, in this example, each of the images 32-9 (inspection images) of the inspection regions for which data has been acquired includes, either partially or entirely, the image 30a-9 of the pattern 30-9 on the wafer inspection surface 32-9.

If a YES decision is made in Step 344-9 (if the incremented image number i does exceed the set value $i_{max}$), Execution returns from this subroutine to the main routine (FIG. 44), and goes on to the comparison step (Step 308-9).

The image data transferred to memory in Step 340-9 is composed of 'beta' data (secondary electron intensity data) for each pixel detected by the detector 36-10. This data however, is subjected to a series of computations during the subsequent comparison step (Step 308-9 of FIG. 44), in which it is matched against the reference standard image data). This image data may be saved in different states, at different stages of the computation, in the memory area 58-6.

This computation process may include, for example, a normalization process in which the size data and/or density data of the inspection image is matched against the size and/or density of the reference standard image, processes in which discrete groups of less than a prescribed number of pixels is viewed as noise and excluded from the process, etc. In addition, instead of using raw beta data, data may be compressed (to the extent that will not degrade detection accuracy for inspection of high precision fine patterns), by converting it to characterization matrices made up of characteristics extracted from the detected patterns.

There a number of matrices that could be used for this purpose. One example would be an m×n characterization matrix arrived at by dividing each two-dimensional inspection region made up of M×N pixels into m×n blocks (m<M, n<N), and using, as matrix elements, values equal to the sums of the secondary electron intensities of the pixels contained in each block (or a normalized value arrived at by dividing each such value (i.e., the total electron intensity of each block) by the number of pixels in the entire region to be inspected). If this is done, the reference standard image data would be stored in the same form. Image data, as referred to in the present embodiment of the invention, includes, of course, raw beta data, in addition to image data in formats such as the above, wherein data characteristics are extracted according to an appropriate algorithm.

Next, the process flow for Step 308-9 will be discussed with reference to the flow diagram of FIG. 46. First, the CPU of the controller 42-10 reads reference standard image data out of the reference standard image memory section 54-6 (FIG. 42), and transfers it to working memory in RAM, etc. (Step 350-9). In FIG. 42, this image data is identified by the reference number 46-10. The image number is then reset to i=1 (Step 352-9), and the inspection image data for image number i is read from the memory section 8-9, and transfers it to working memory (Step 354-9).

Next, the reference standard image data and the image i data just read from memory are matched against each other, and the distance between them is computed as a distance value $D_i$ (Step 356-9). The distance value $D_i$ is indicative of the degree of similarity between the reference standard image and the inspected image i. (The larger the value of $D_i$, the greater the difference between the inspected image and the reference standard image.) The actual value of $D_i$ is arbitrary, as long as its magnitude expresses the degree of similarity. For example, when the image data is in the form of an M×N pixel matrix, the secondary electron intensity of each pixel (or characteristic magnitude) may be viewed as position vector components of an (M×N)-dimensional space, and either the Euclidean distances between the reference standard image vectors and the image i vectors within this (M×N)-dimensional space, or their correlation coefficients, computed. Of course, distance other than Euclidean (e.g., so-called 'urban district distance') may also be computed. In addition, if the number of pixels is large, the computed magnitude can get quite large, and in this case the distance between the two sets of image data (inspection and reference image), expressed in the form of the above m×n characteristic vectors may be computed instead.

Figure 46:
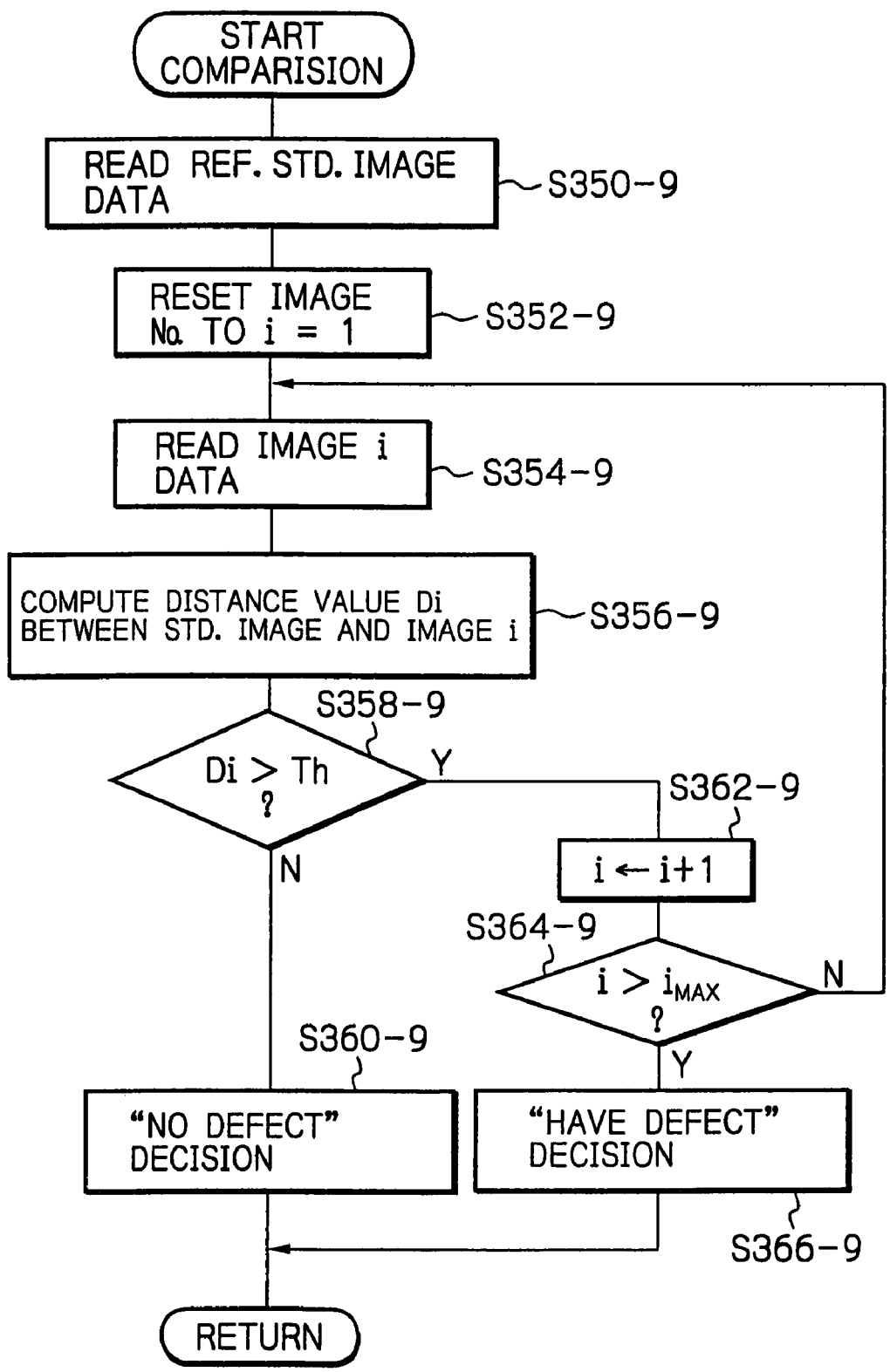
FIG. 46 is a detailed subroutine flow diagram for the comparison step (Step 308-9) in the main routine of FIG. 44.

I reversed the 'greater than/less than' and 'yes/no' parts of the following text to make it agree with the drawing in Step 358-9 of FIG. 46. This appears in the paragraph after this one.

Next, a decision is made as to whether the computed distance $D_i$ exceeds a threshold value Th (Step 358-9). The value of the threshold Th (determined through experimentation) sets the standard as to whether there is a sufficient match between the inspected and reference standard images. If the distance $D_i$ value does not exceed the prescribed threshold Th, (a NO decision in Step 358-9), the present inspection surface 34-9 of the present wafer gets a 'no defect' decision (Step 360-9), and execution returns to this subroutine. In other words, if even one of the inspection images is substantially a match for the reference standard image, a 'no defect' decision is rendered. Since not all of the inspection images need to be subjected to this matching process, this can be a high-speed decision process. In FIG. 42, the column 3, row 3 inspection image, for example, has no positional offset from, and is substantially matched with, the reference standard image.

If the distance $D_i$ value exceeds the threshold (YES at Step 358-9), the image number i is incremented by 1 (Step 362-9), and a decision is made as to whether the incremented image number (i+1) exceeds the set value $i_{max}$ (Step 364-9). If not (if the decision in Step 364-9 is NO), execution returns to Step 354-9 to read image data for image number i+1, and repeat the matching process for that image data. If the incremented image number i exceeds $i_{max}$ (YES at Step 364-9), a 'have defect' decision is made for the present inspection surface 34-9 of the present wafer W at Step 366-9, and execution returns to the main routine. In other words, a 'have defect' decision is made if there is a substantial mismatch between the reference standard image and all of the inspection images.

In the embodiment described above, the image data-to-image data matching process was performed either between pixels or between characteristic vectors, but it could be performed for a combination of the two. For example, high-speed matching of low-computed-magnitude characteristic vectors could be performed first; followed by a detailed pixel-to-pixel matching process for only those inspection images determined to have a high degree of similarity in the first check. Such a two-stage procedure could provide both high speed and high accuracy.

Also, in the present invention, positional displacement of the inspection image is correlated with positional displacement of the region irradiated by the primary electron beams. The present invention could, however, be used in conjunction with a process performed either before or between matching processes to search for matching regions having the best image data match (e.g., a process for detecting regions having the highest coefficient of correlation therebetween, and performing matching on those regions). Thus correlation between large displacement of inspection images with displacement of the region irradiated by the primary electron beam according to the present invention could be determined, and regions of comparatively small displacement left to be absorbed by subsequent digital image processing. Neither is the process flow limited to that shown in FIG. 44. For example, in the flow of FIG. 44, if a sample is judged defective at Step 312-9, no further inspection for defects in other regions is performed. This flow could be changed, however, so that all regions would be covered. Also, if the region irradiated by primary electron beams can be enlarged to where substantially all of the inspection regions can be covered in one shot, Steps 314-9 and 316-9 can be eliminated.

Thus in the above process, images are acquired for multiple inspection regions on the sample that partially overlap but are offset with respect to each other, and the images of these inspection regions are compared with a reference standard image, to detect defects in the sample. This provides a major advantage in that it eliminates degradation of defect detection accuracy due to positional displacement between the reference standard image and the image being inspected.

Correcting Deviation of the Irradiated Point from the Design Point

Another improvement incorporated in the above inspection apparatus of FIG. 42 is described below. That is, in such an inspection apparatus, when there are deviations from the design values specified for the attitude (state of rotation), positions, or separation between the above primary beamlets being directed toward the stage, it is no longer possible to perform proper inspections with the system. Therefore, the present system was designed so that when such deviations from design values occur, it will be possible to calibrate and correct for them.

At the expense of being repetitious, to best serve the purposes of this description, we will start with an overview of the system shown in FIG. 42. An electron beam emitted from an electron gun 2-10 is converged by a condenser lens 4-10 to form a crossover at a point 6-10. Placed below the condenser lens 4-10 is a first multi-aperture plate 8-10 having a plurality of apertures through which a plurality of primary electron beamlets 12-10 are formed about an optical axis 10-10. A demagnification lens 14-10 demagnifies these primary electron beamlets formed by the first multi-aperture plate 8-10, and projects them onto a plane at a point 16-10. After being thus focused at the point 16-10, the beamlets are again focused on a sample 20-10 by an objective lens 18-10. The multiple primary electron beamlets 12-10 emerging from the first multi-aperture plate 8-10 are deflected by a deflector 22-10 placed between the demagnification lens 14-10 and the objective lens 18-10 as a scanning device, such that they simultaneously scan the surface of the sample 20-10. Although the scanning of the multiple primary electron beamlets 12-10 could be performed entirely by the deflector 22-10, the deflector 22-10 and an ExB separator (to be described later) may also be used for this purpose.

Figure 49:
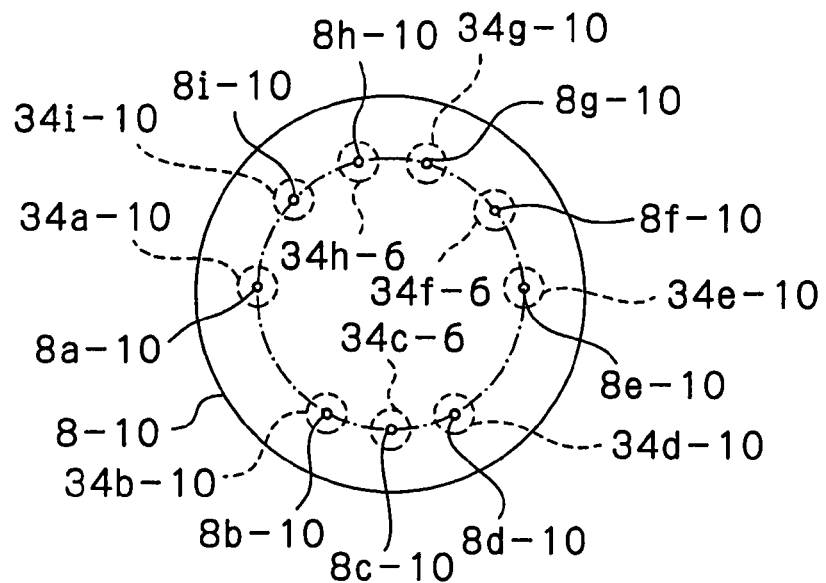
FIG. 49 is a simplified front view of a first multi-aperture plate.
Figure 50:
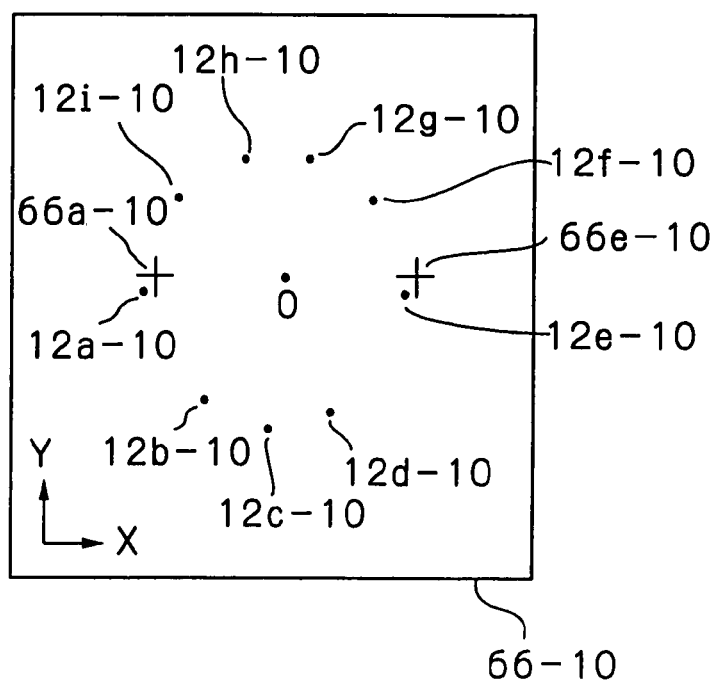
FIG. 50 is a simplified plan view of a mark pad.

As shown in FIG. 49, to eliminate the effects of image plane curvature aberration of the demagnification lens 14-10 and the objective lens 18-10, the multi-aperture plate 8-10 has provided therein, nine small apertures 8a-10 through 8i-10 arranged along a circle on an end surface thereof so that images projected toward the X-direction thereof will be equally spaced. As shown in FIG. 50, by passing through the apertures 8a-10 through 8i-10 of the multi-aperture plate 8-10, the primary electron beam 12-10 is formed into nine beamlets 12a-10 through 12i-10, which are thus arranged to pass through a circle in positions corresponding to those of the apertures. Also, although in the present example, the apertures are arranged along a circle, this is not a requirement: they could instead be arranged in a straight line. Also, although nine apertures were used, there as few as two could be used.

Multiple points on the sample 20-10 are irradiated by the converged primary electron beamlets 12-10. The secondary electron beamlets that are then emitted from these irradiated points are attracted and tightly converged by the electric field of the objective lens 18-10 and deflected by the ExB separator 24-10, to thus separate them from the primary electron beamlets irradiating the sample 20-10, and inject them into the secondary optical system.

The reference number 17-10 in FIG. 42 identifies an axial alignment deflector, and the reference number 19-10 identifies an axially symmetrical electrode. Also, a rotation lens 23-10 that is capable of rotating the multiple primary electron beamlets 12-10 is provided between the multi-aperture plate 8-10 that forms part of an electron beam forming device, and the ExB separator 24-10 that functions as a separation device. More specifically, in this mode of the invention, the rotation lens 23-10 is placed near the point 6-10 of FIG. 42. This rotation lens 23-10 is capable of rotating the primary electron beamlets 12-10 about the optical axis, responsive to the intensities of the excitation currents flowing in its coils.

The secondary optical system has magnification lenses 28-10 and 30-10 for imaging the secondary electron beams passed therethrough at the multiple apertures 34a-10-34i-10 of a second multi-aperture plate 34-10. After passing through multiple apertures, the secondary electron beams are detected by the multiple detector elements 36a-10-36i-10. (The second multi-aperture plate 34-10 is placed in front of the detector elements 36a-10 through 36i-10.) The apertures 34a-10-34i-10 are formed in the second multi-aperture plate 34-10 along a circle on an end surface thereof such as to correspond on a one-for-one basis with respective apertures 8a-10-8i-10 formed in the first multi-aperture plate 8-10. To show this correspondence in FIG. 49, the apertures 34a-10-34i-10 of the second multi-aperture plate 34-10 are indicated by dotted lines. The detector elements 36a-10-36i-10 are placed opposite the apertures 34a-10-34i-10, respectively, of the second multi-aperture plate 34-10, and are therefore placed along a circle as the apertures. (For convenience, the detector elements 36a-10-36i-10 are shown schematically as blocks in FIG. 42.) Each of the detector elements 36a-10-36i-10 converts its secondary electron beamlet to an electrical signal representative of the intensity of that beamlet. Each of these electrical signals output by the detector elements is then amplified by an amplifier 38-10, and input to the image processor 40-10, where it is converted to image data. A signal that is the same as the scan signal applied to the deflector 22-10 for deflecting the primary electron beams is also supplied to the image processor 40-10 by the controller 42-10. Using position data from the scan signal, and secondary electron density data from the secondary electron signals, the image processor 40-10 generates image data from which it can construct and display an image of the scanned surface of the sample 20-10.

The image processor 40-10 is connected to the controller 42-10 for conducting data communication therebetween. The controller 42-10, may be a general use personal computer, as shown in FIG. 42. This computer comprises a main control unit 44-10 for executing control and computation processes in accordance with a prescribed program; a monitor 48-10 for displaying the results of these processes, and secondary electron images 46-10; and an input device 50-10 (such as a keyboard or mouse) for inputting commands entered by an operator. The controller 42-10 may also, of course, be configured as dedicated defect inspection system hardware, or as a workstation, etc.

The main control unit 42-10 comprises various circuit boards and major components not shown on the drawing (CPU RAM, ROM, hard disk, video board, etc.). A memory unit 52-10 is connected to the controller 44-10. This memory unit 52-10 could be, for example, a hard disk. Within this memory unit 52-10, is a secondary electron image memory area 54-10, allocated for storage of sample 20-10 secondary electron image data received from the image processor 40-10; and a reference standard image memory area 56-10, allocated for advance storage of reference standard image data taken from defect-free samples. Also stored in the memory unit 52-10 is a control program for controlling the overall electron beam apparatus; a sample evaluation program; and a control program 58-6, for performing calibrations and making corrections, in order to correct for deviations from the design values specified for the attitude (state of rotation), positions, or separation between multiple primary beamlets being directed toward the sample, when such deviations occur. The control method for calibrating primary electron beam deviations of this type will be explained in detail later, but it should be noted at this point that calibration is performed before performing any sample evaluations, in order to establish the initial primary electron beam settings.

The image data for the scanned surface of the sample 20-10 (stored in the secondary electron image area memory 54-10) is compared against standard reference image data taken from defect-free samples (stored in advance in the reference standard image memory 56-10) in order to detect the presence of defects in the sample 20-10.

The line width of a pattern on a sample 20-10 can be measured as follows: The sample 20-10 pattern to be evaluated is moved into the proximity of the optical axis 10-10 of the primary optical system, and a line scan is performed to obtain a line width evaluation signal. That signal is then calibrated by a procedure (registration calibration) to be described later.

To measure the X position of the stage 60, a moving mirror is provided by mounting a laser-reflecting mirror 62-10 on an X-direction end of the stage 60-10; and a stationary mirror is provided by mounting a mirror on the objective lens. The distance between the fixed and moving mirrors is constantly measured by establishing interference between a laser beam emitted by a laser 64-10 and reflected from the stationary mirror, and a beam reflected from both the moving mirror and the stationary mirror. Measurement signals obtained from the resulting interference patterns are sent to the controller 42-10, which uses the signals to compute the X position of the stage. Also, a moving mirror is mounted on a Y-direction end of the stage 60-10 (not shown), and a fixed Y-direction measurement mirror is mounted on the end of the objective lens, such that the Y position of the stage 60-10 can be measured from the interference resulting when a laser beam emitted by a laser (not shown) positioned outward of the stage, is reflected by the two mirrors.

A mark pad 66-10 is provided on one side of the stage 60-10. The surface of the mark pad 66-10 constitutes an XY coordinates plane (FIG. 50). As shown in FIG. 50, provided on the mark pad 66-10, are two beam position measurement marks, 66a-10 and 66e-10. The marks 66a-10 and 66e-10 are provided along the X-axis, substantially parallel thereto. (Their degree of parallelism to the X-axis is measured beforehand and stored in the memory unit 52-10 of the controller 42-10 as a system constant.) In FIG. 50, the center point between the mark 66a-10 and 66e-10 is indicated by the letter O.

Using the stage drive system described above, the stage 60-10 can be moved in the X and Y directions to a position at which the surface of the mark pad 66-10 can be irradiated by the primary electron beams 12-10. When this is done, a plurality of irradiation points 12a-10-12i-10 are formed around a circle on the surface of the mark pad 66-10. (That is, the primary electron beamlets 12a-10-12i-10 are formed at the surface of the mark pad 66-10, as shown in FIG. 50.) The marks 66a-10 and 66e-10 are formed so that the distance between them will be less than the scan width used when the marks are scanned. This is done so that one primary electron beamlet will not be able to irradiate both marks in the same scan. Because there is exact correspondence between the primary beamlets and the detector elements this will also prevent the signal produced by the scanning of the mark by one primary beamlet from being mistaken for the signal produced by another.

Next, the electron beam calibration method will be described with reference to FIGS. 51 through 53(*c*). First, the stage drive system is operated to drive the stage 60-10 as required to move the mark pad 66-10 under the optical axis, and align the position of the optical axis 10-10 with the center point O between the marks 66a-10 and 66e-10 (Step 68-10 of FIG. 51). This alignment should be accurate to within a prescribed error margin. The above can be done, for example, by scanning the primary electron beams over a prescribed range in the X and Y directions, and confirming that the marks 66a-10 and 66e-10 are detected by the primary beamlets 12a-10 and 12e-10 (the beams that are on the X axis) that form the irradiation points 12a-10 and 12e-10. When alignment is performed in this manner between the optical axis 10-10 and the mark pad 66-10, primary electron beamlets 12a-10 and 12e-10 irradiate the pad in the vicinity of the marks 66a-10 and 66e-10 as shown, for example, in FIG. 52(*a*). This enables the primary electron beamlets 12a-10 and 12e-10 to be scanned so as to cut across the marks 66a-10 and 66e-10 by scanning the beamlets over their prescribed ranges in the X and Y directions.

Figure 52A:
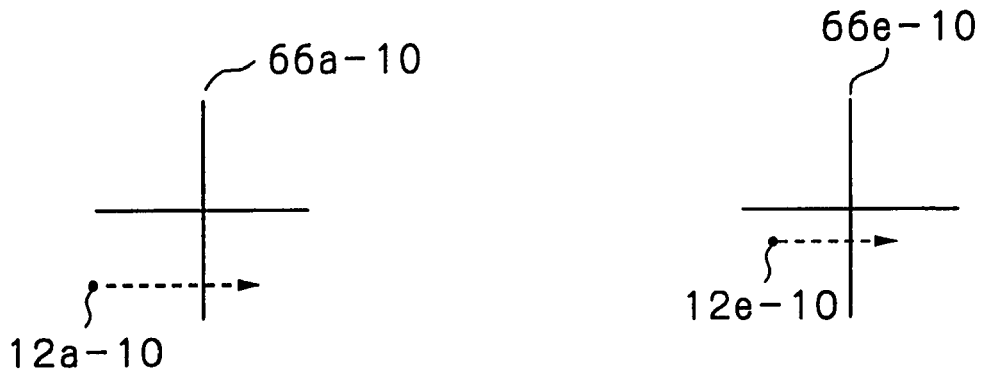
FIG. 52(a) is a simplified drawing showing a method of calibrating the X-axis irradiation positions, on a mark pad, of a plurality of primary electron beams.
Figure 52B:
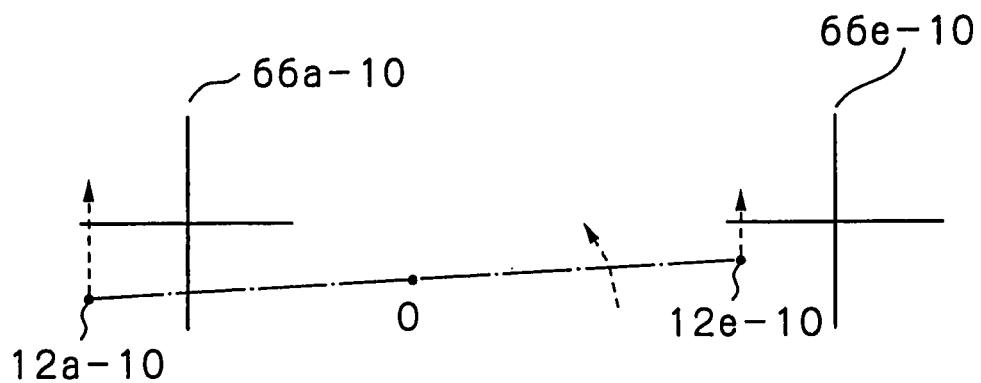
FIG. 52(b) is a simplified drawing showing a method of calibrating the Y-axis irradiation positions, on a mark pad, of a plurality of primary electron beams.
Figure 52C:
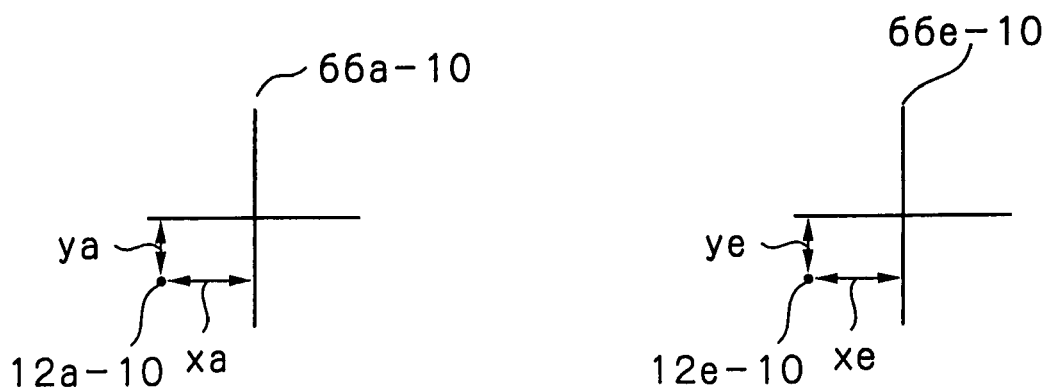
FIG. 52(c) is a simplified drawing for describing aligning the position of the optical axis with a mark position.

In the example shown in FIG. 52(*a*), the distance between the mark 66a-10 and the irradiation point of the primary electron beamlet 12a-10 is longer in both the X and Y directions than the distance from the mark 66e-10 to the irradiation point of the primary electron beamlet 12e-10. That is, in this example, the distance between the primary electron beamlet 12a-10 and 12e-10 irradiation points and the marks 66a-10 and 66b-10 represents the deviation of the primary electron beamlets from their predicted values (i.e., the multibeam deviation).

When alignment of the optical axis 10-10 and the mark pad 66-10 is performed, the position of the stage 60-10 is computed (using the laser-reflecting mirror 62-10 and the linear measurement laser 64-10) and these position data are then stored in the memory 52-10 as the mark position system constant. Normally, this alignment of the optical axis 10-10 and the mark pad 66-10 positions needs to be performed only once, when the electron beam apparatus initial settings are performed. The mark position system constant, based on the above alignment, however, is updated based on a calibration process to be described later.

Next, the positioning of the primary electron beamlets relative to each other is measured. In the present embodiment, this measurement is performed by providing two marks on a mark pad, and scanning two electron beamlets 12a-10 and 12e-10, which form irradiation points in the vicinity of the two marks 66a-10 and 66e-10, so that the beams will cut across the marks. To illustrate this embodiment as clearly as possible, the other electron beamlets (b-d and f-i) are not shown in FIGS. 52 through 53(*c*).

First, under direction of the control program 58-10 (stored in the memory unit), the controller 42-10 controls the deflector 22-10 to scan the electron beamlets 12a-10-12e-10 in the X-direction, toward the marks 66a-10 and 66e-10, as shown in FIG. 52(*a*). When this is done, the primary electron beamlet 12e-10 crosses over the mark 66e-10 first, after which, the primary electron beamlet 12a-10 crosses over the mark 66a-

10. Therefore, as shown in FIG. 53(*a*), the signal 90-10 output by the detector element 36*e*-10 (the signal corresponding to the primary electron beamlet 12*e*-10) appears first, followed by the signal 92-10, which is output by the detector element 36*a*-10 (the signal corresponding to the primary electron beamlet 12*a*-10). FIG. 53(*a*) shows signal strength on the vertical axis and time on the horizontal axis. Since the primary electron beam scan rate (μm/μsec) in the X-axis direction is known in advance, the X-direction distance between the mark 66*a*-10 and the primary electron beamlet 12*a*-10 (i.e., the irradiation point 12*a*-10), and the X-direction distance between the mark 66*e*-10 and the primary electron beamlet 12*e*-10 (i.e., the irradiation point 12*e*-10), can be computed from the times at which the two signals 90-10 and 92-10 are output. The time between the two signals 90-10 and 92-10 can, of course, also be used to compute the distance between the two primary electron beamlets 12*a*-10 and 12*e*-10 (i.e., their irradiation points 12*a*-10 and 12*e*-10).

Figure 51:
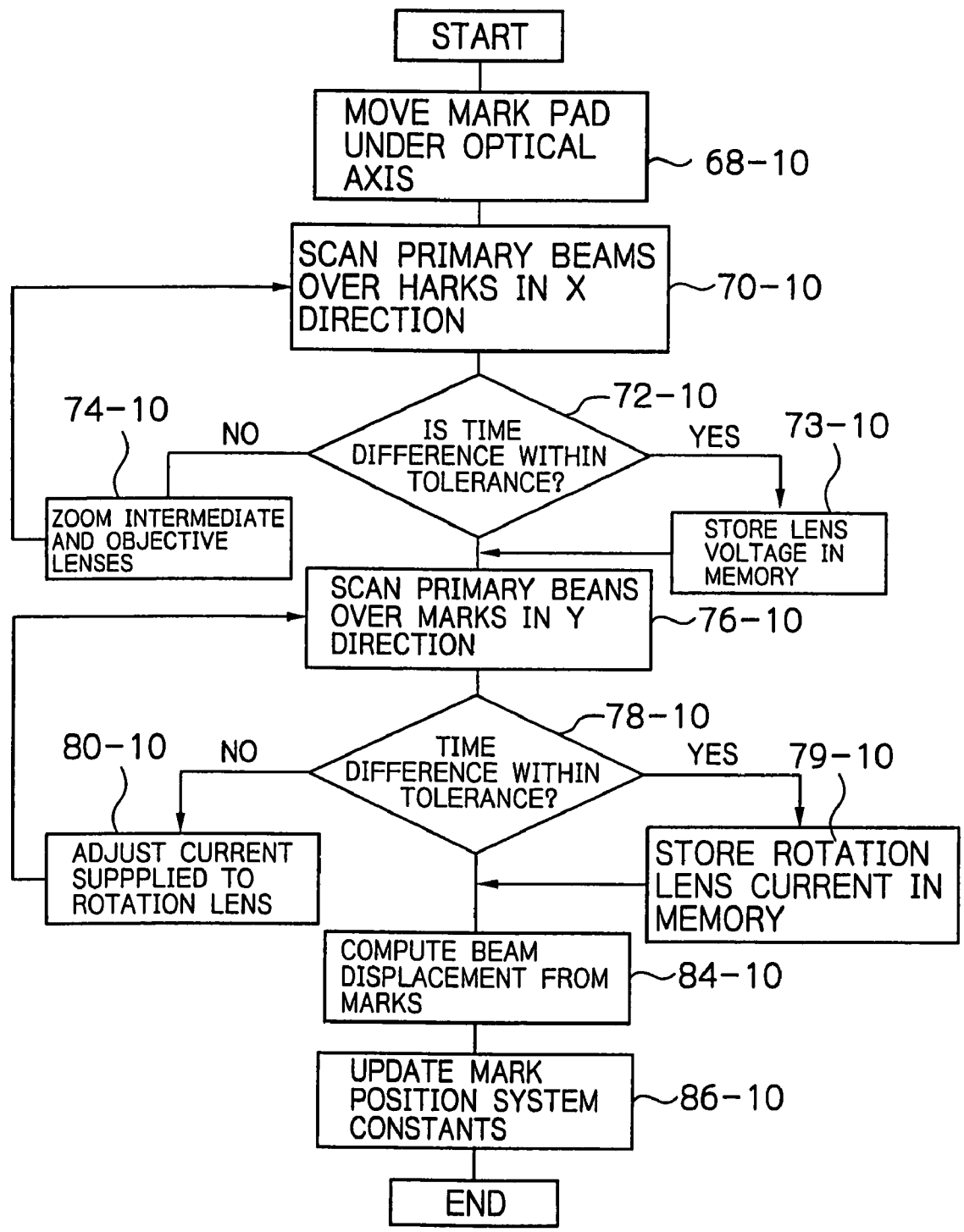
FIG. 51 is a flow chart for a method of calibrating the irradiation positions of a plurality of electron beams.

Next, the time difference between the two signals 90-10 and 92-10 is computed, and a decision made as to whether this time difference falls within the error tolerance for its design value (Step 72-10 of FIG. 51, which uses a measurement device.) If the time difference is not within tolerance, a zoom operation is performed with the intermediate lens 14-10 and the objective lens 18-10 of FIG. 42 under control of the controller 42-10. That is, the demagnification ratio is changed without changing the object position 8-10 and the image position 20-10. (Step 74-10 of FIG. 51, which uses a two-stage lens control device.) This changes the X position of the primary electron beamlet 12*a*-10 (i.e. the irradiation point 12*a*-10) with respect to the mark 66*a*-10, and the X position of the primary electron beamlet 12*e*-10 (i.e. the irradiation point 12*e*-10) with respect to the mark 66*e*-10. In this manner, steps 70-10, 72-10 and 74-10 are repeated until the waveforms of the signals 90-10 and 92-10 appear at substantially the same point in time. When this is done, on the mark pad 66-10, the distance in the X direction between the mark 66*a*-10 and the primary electron beam 12*a*-10 (i.e. the irradiation point 12*a*-10), and the distance in the X direction between the mark 66*e*-10 and the primary electron beam 12*e*-10 (i.e. the irradiation point 12*e*-10) will be substantially equal, as shown in FIG. 52(*b*). When a decision is made that the time difference between the two signals 90-10 and 92-10 is within tolerance (Step 72-10), the values of the excitation voltages applied to the intermediate lens 14-10 and the objective lens 18-10 at this time are stored in the memory unit 52-10 (Step 73-10).

Next, under direction of the control program 58-10, stored in the memory unit 52-10, the controller 42-10 controls the deflector 22-10 to scan the electron beamlets 12*a*-10-12*e*-10 in the Y-direction, toward the marks 66*a*-10 and 66*e*-10, as shown in FIG. 52(*b*) (Step 76 of FIG. 51). When this is done, the primary electron beamlet 12*e*-10 crosses over the mark 66*e*-10 first, after which, the primary electron beamlet 12*a*-10 crosses over the mark 66*a*-10. Therefore, as shown in FIG. 53(*b*), the signal 94-10 output by the detector element 36*e*-10 (the signal corresponding to the primary electron beamlet 12*e*-10) appears first, followed by the signal 96-10, which is output by the detector element 36*a*-10 (the signal corresponding to the beamlet 12*a*-10). FIG. 53(*b*) shows signal strength on the vertical axis and time on the horizontal axis. Since the primary electron beam scan rate (μm/μsec) in the Y-axis direction is also known in advance, the Y-direction distance between the mark 66*a*-10 and the primary electron beamlet 12*a*-10 (i.e., the irradiation point 12*a*-10), and the Y-direction distance between the mark 66*e*-10 and the primary electron beamlet 12*e*-10 (i.e., the irradiation point 12*e*-10), can be computed from the times at which the two signals 94-10 and 96-10 are output.

Next, the time difference between the two signals 94-10 and 96-10 is computed, and a decision made as to whether this time difference falls within the error tolerance for its design value (Step 78-10 of FIG. 51). If the time difference is not within tolerance, and the signal 94-10 occurs first in time, as shown in FIG. 53(*b*), this shows that the primary electron beamlets are rotated counterclockwise, with the center point 0 as the center of rotation, as shown by the arrow in FIG. 52(*b*). When this kind of misalignment exists, the controller 42-10 adjusts the intensity of the excitation current supplied to the rotation lens 23-10 shown in FIG. 42 (Step 80-10 of FIG. 51), thus rotating the primary electron beamlets clockwise. Steps 76-10, 78-10, and 80-10 are repeated as required to adjust the signals 94-10 and 96-10 to where they both appear as close as possible (within tolerance) to the same point in time. When this is done, on the mark pad 66-10, the distance in the Y direction between the mark 66*a*-10 and the primary electron beam 12*a*-10 (i.e. the irradiation point 12*a*-10), and the distance in the Y direction between the mark 66*e*-10 and the primary electron beam 12*e*-10 (i.e. the irradiation point 12*e*-10) will be substantially equal. In this state, a line drawn between the marks 66*a*-10 and 66-10 will be substantially parallel to a line drawn between the primary electron beam 12*a*-10 (the irradiation point 12*a*-10) and the primary electron beam 12*e*-10 (the irradiation point 12*e*-10). In other words, in this state, there is no rotation error. When a decision is made that the time difference between the two signals 94-10 and 96-10 is within tolerance (Step 78-10), the value of the rotation lens 23-10 excitation current at this time is stored in the memory unit 52-10 (Step 79-10).

When the above calibration process from step 68-10 through 80-10 has been performed, on the mark pad 66-10, the distance xa, the distance in the X direction between the mark 66*a*-10 and the primary electron beam 12*a*-10 (i.e. the irradiation point 12*a*-10), and the distance xe, the distance in the X direction between the mark 66*e*-10 and the primary electron beam 12*e*-10 (i.e. the irradiation point 12*e*-10) will be substantially equal, as shown in FIG. 52(*c*). Also on the mark pad 66-10, the distance ya, the distance in the Y direction between the mark 66*a*-10 and the primary electron beam 12*a*-10 (i.e. the irradiation point 12*a*-10), and the distance ye, the distance in the Y direction between the mark 66*e*-10 and the primary electron beam 12*e*-10 (i.e. the irradiation point 12*e*-10) will be substantially equal.

Finally, the amount of alignment between the positions of the optical axis and the marks is either computed or measured, as described below. After the above calibration process has been performed, the signals 90-10 and 92-10 are output at substantially the same time when the beams are scanned in the X direction and the signals 94-10 and 96-10 are output at substantially the same time when the beams in the Y direction. Therefore, this means that, as shown in FIG. 53(*c*), the deflection voltage 92-10 (the deflector 22-10 deflection voltage) that exists when the signal 90-10 is output, is equal to the deflector 22-10 deflection voltage that exists when the signal 92-10 is output. Also, the deflector 22-10 deflection voltage that exists when the signal 94-10 is output, is equal to the deflector 22-10 deflection voltage that exists when the signal 92-10 is output. Also, as described above, the values of the excitation voltages applied to the lenses 14-10 and 18-10 when the signals 90-10 and 92-10 are output at substantially the same time, and the excitation current supplied to the rotation lens 23-10 when the signals 94-10 and 96-10 are output at substantially the same time are stored in memory (Steps 73-10 and 79-10 of FIG. 51). The deflection sensitivity (μm/mv) of the deflector 22-10 is also stored in the memory 52-10.

Therefore, the number of microns by which the positions of the primary electron beamlets are displaced from the positions of the marks in the X direction, when the beams are scanned in the X direction (i.e., the distances xa and xe in FIG. 52(*c*)), is computed based on the deflector sensitivity (μm/mv), which is known in advance, and the deflection voltage that exists when the beams are scanned in the X direction. Also, the number of microns of Y-direction positional displacement between the beams and the marks, when the beams are scanned in the Y direction (i.e., the distances ya and ye) are computed, based on the above deflection voltages (Step 84-10 of FIG. 51). Then, the mark position system constants are updated to new values by adding these positional displacement values to stage position data previously measured by interferometer, and stored in memory (Step 86-10 of FIG. 51).

The measurements shown in FIGS. 52(*a*) and (*b*) and FIGS. 53(*a*) and (*b*) are immune to stage vibration measurement error. With respect to the measurements shown in FIG. 52(*c*) and FIG. 53(*c*) as well, since dimensions computed from the deflector sensitivity are added to laser length measurement device readings taken at the instant of measurement, these measurements are also immune to stage vibration error. Thus the measurements shown in FIGS. 52(*c*) and 53(*c*) may be taken while the stage is in motion.

According to the above embodiment, evaluation of semiconductor wafers having minimum pattern line widths of 0.1 μm or less can be performed with high throughput and reliability. Also, measurement of the rotation of, and separation between, the multiple electron beams (multibeam beamlets), and of the positional displacement between beams and marks can be performed without the measurements being affected by stage vibration. In addition, because the primary electron beams can be precisely aligned with the XY coordinates of a mark pad, images can be formed without performing complex computations.

The above calibration method can be performed automatically by a control system, under control of a program stored in memory; or it can be performed manually while observing image data on a monitor.

Also, in the present embodiment, the calibration process was described using two of the nine primary electron beamlets in the system, but it should be noted that at least two primary electron beams are required to perform the calibration.

In the present invention as described above, the positional displacements of irradiation points relative to position measurement marks are measured. When positional displacement is measured, the irradiation points of the multiple primary electron beamlets are then calibrated (and related system constants are updated) based on that positional displacement. Therefore, even when deviations from design values develop in terms of the position and attitude (rotation) of the multiple electron beamlets incident to the stage, and the distance between those electron beams, since the system can be calibrated to correct for these deviations, it will still be possible to perform high resolution, high throughput inspections for defects in samples.

Correcting Aberrations (Adjusting Crossover Position)

In the prior electron beam inspection apparatus described earlier, an aperture was provided for adjusting the position of a crossover formed near the objective lens. To adjust the crossover position, the beam diameter was measured as this aperture was being shifted along the optical axis. The point at which the smallest beam diameter was measured was then used as the crossover position. The problem with this adjustment method, however, was that the characteristics of the lenses adjacent to the aperture were dramatically changed when the aperture was moved, and the design characteristics of the lenses could therefore no longer be realized.

On the other hand, since all or a portion of the multiple electron beams are positioned away from the optical axis, the crossover position influences a number of aberrations, including image distortion, magnification chromatic aberration, rotation chromatic aberration, field plane curvature aberration, and field astigmatism, with the influence of magnification chromatic aberration and rotation chromatic aberration being especially significant.

It is therefore also an object of the present invention to provide the capability to adjust the position of the crossover near the objective lens such that aberrations can be corrected without affecting the lens characteristics. The crossover position adjustment method of the present invention is described below.

Figure 54:
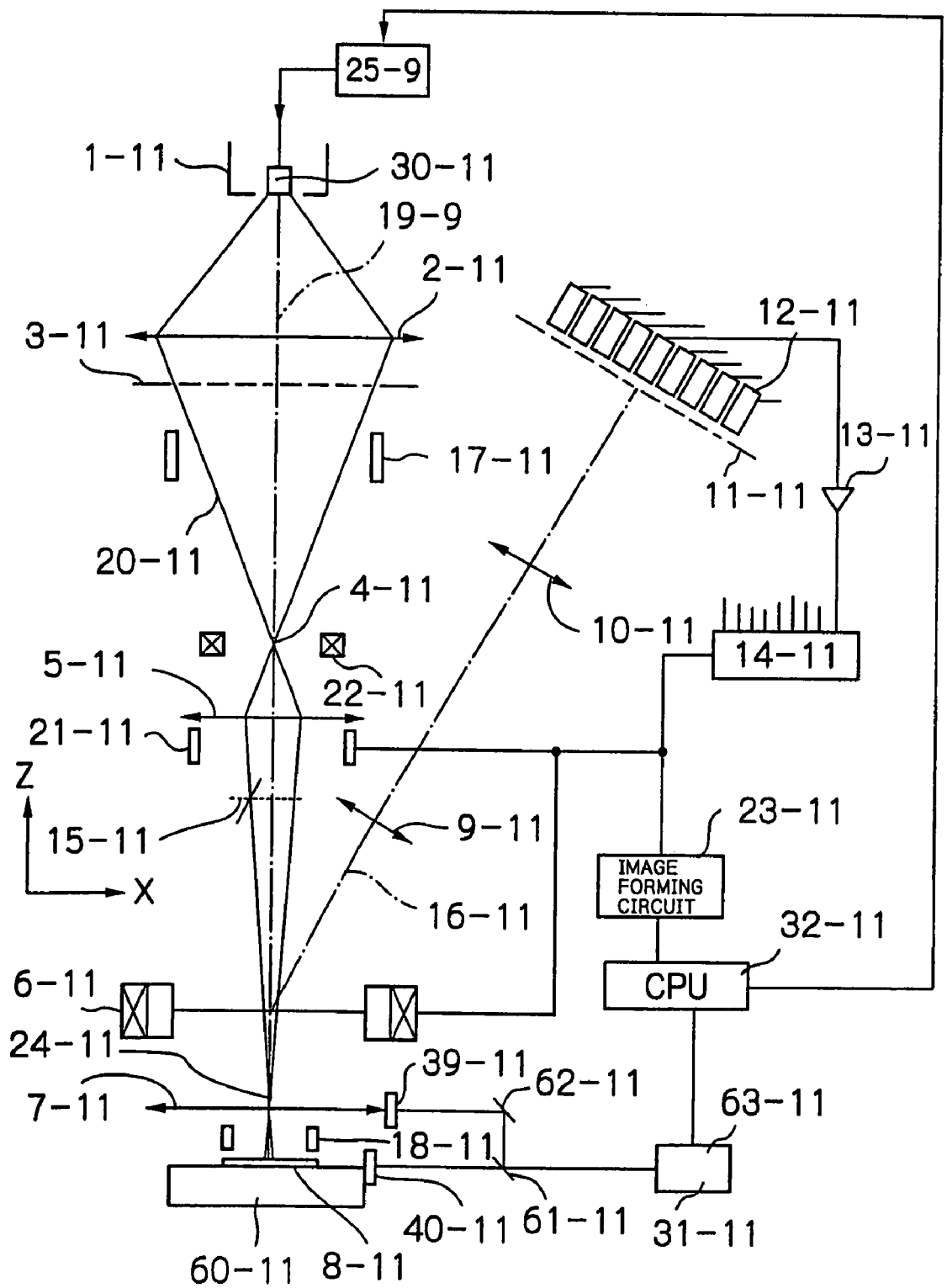
FIG. 54 is a schematic diagram of an electron optical system, used to describe adjustment of the position of a crossover.

FIG. 54 shows a schematic representation of an electron optical system for describing the adjustment. It is essentially the same as the other electron optical systems described up to this point. In this optical system, multiple primary electron beams 20-11 formed by a first multi-aperture plate 3-11 are demagnified by a demagnification lens 5-11 to be projected at a point 15-11. After being focused at the point 15-11, the beams are focused on a sample W by an objective lens 7-11. The multiple primary electron beams 20-11 are also converged by the demagnification lens 5-11 to form a crossover at a point 24-11. This crossover position 24-11 is near the objective lens 7-11 (or more specifically, between the objective lens 7-11 and an ExB separator 6-11 that will be discussed later). By adjusting this position in the Z-axis direction, any one of the following aberrations can be reduced almost to zero: magnification chromatic aberration, rotation chromatic aberration, distortion, landing angle, and coma.

Also shown in FIG. 54 are an axis alignment deflector 17-11, and an axially symmetrical electrode 18-11. Also provided between the multi-aperture plate 3-11 that forms part of the multibeam beamlet-forming system and the ExB separator 6-11, is a rotation lens 22-11, for rotating the multiple electron beams 20-11. More specifically, the rotation lens 22-11 is located near the point 4-11. This rotation lens 22-11 is capable of rotating multiple primary electron beamlets 20-11 about the optical axis, responsive to the intensity of excitation currents flowing in its coils. A sample W is loaded on a stage 60-11. The stage 60-11 made so that it can be moved, by a stage drive system not shown in the drawing, in an X direction (left and right in FIG. 54), a Y direction (perpendicular to the page on which FIG. 54 appears), and a Z-axis direction (up and down in FIG. 54).

Also provided is a laser 31-11, for generating a laser beam. This laser beam is split into two beams by a half-reflecting mirror 61-11. Of these two beams, the one that passes through the half-reflecting mirror 16-11 becomes incident to a moving mirror 40-11 that is attached to an X-direction end of the stage 60-11. The other beam from the half-reflecting mirror 61-11 is reflected by a fully-reflecting mirror 62-11 to become incident to a stationary mirror 39-11 that is provided on the objective lens 7-11. The two beams are thus reflected from the moving mirror 40-11, and the stationary mirror 39-11, respectively. The beam reflected from the moving mirror 40-11 passes through the half-reflecting mirror 16-11 to be guided to a receiver 63-11. The beam reflected from the stationary mirror 39-11 is reflected by the fully-reflecting mirror 62-11 and the half-reflecting mirror 61-11 to also be guided to the receiver 63-11. In the receiver 63-11, interference light of the beams reflected from the moving and stationary mirrors (40-11 and 39-11) is detected. The detected signal is sent to a CPU 32-11, which determines therefrom, the distances in the X and Y directions between the moving and stationary mirrors (40-11 and 39-11); i.e., the x,y coordinates of the stage 60-11 position. A mark (not shown) is also provided on the stage 60-11. The stage 60-11 can be moved in the X and Y directions by the drive system mentioned above, to a location wherein the surface of the mark can be scanned by the primary electron beams 20-11. The positions of the beams 20-11 can now be detected by scanning the beams over the mark.

The CPU 32-11 is connected to the cathode power supply 25-11 for the cathode 30-11 of an electron gun 1-11 such that the voltage applied to the cathode 30-11 can be controlled by the CPU 32-11 to vary periodically between a few tens of volts and a few hundred volts. Changes in beam position that occur when the voltage applied to the cathode 30-11 is varied in this manner can then be detected by the CPU 32-11, and used to measure the movement of the beams. In other words, the movement on the sample W of the multiple beams 20-11 in the direction of irradiation, and in the direction of rotation centered on the optical axis, can be measured, by varying the voltage applied to the cathode 30-11 between a few tens of volts and a few hundred volts, in a periodic cycle. This changing of voltage corresponds to changes in the energy of the beams, which means that when movement of the beams in rotation and in the direction of radiation is minimized, the magnification chromatic aberration and rotational chromatic aberration will also be minimized.

As mentioned above, a crossover is formed by the multiple primary electron beams 20-11 at the crossover position 24-11, near the objective lens 7-11. The above measurement can be performed by CPU 32-11 such as to adjust the crossover position 24-11 along the optical axis to a point at which the above movement of the primary electron beams 20-11 is minimized. This, then, measures the Z-axis position of the crossover 24-11 at which the least magnification chromatic aberration or rotation chromatic aberration occurs. Preferably, this adjustment should be performed after axial alignment of the objective lens 7-11 has been completed. The axial alignment of the objective lens 7-11 can be performed by superimposing an axial alignment power supply voltage on the deflector 21-11.

As stated above, in the past, the use of an aperture to adjust the position of this crossover resulted in huge changes in the electron optical system lens characteristics, causing major problems. According to the embodiment of the invention just described, however, by changing the voltage applied to the cathode 30-11, and adjusting it such as to minimize the movement, on a sample W, of the multiple primary electron beams 20-11, as described above, to thereby adjust the position 24-11 (on the optical axis) of a crossover formed near the objective lens 7-11 by the multiple primary electron beams 20-11, the above adjustment can be performed without affecting the characteristics of the lenses.

Also by adjusting the position along the optical axis of a crossover 24-11 formed near the objective lens 7-11 by the multiple primary electron beams 20-11, in addition to landing angle corrections, any one of the following aberrations can be corrected: image distortion, magnification chromatic aberration, rotation chromatic aberration, coma, and field astigmatism. Also, as discussed above, if an aperture plate such as that shown in FIG. 8. is used, no problems in terms of image distortion or image curvature aberration will be encountered, nor will field astigmatism or landing angle be affected. Therefore, crossover position can be adjusted to correct for magnification chromatic aberration and rotation chromatic aberration without causing other problems.

If, when this is done, an electrostatic lens is used for the objective lens, since this lens has nothing to do with rotation chromatic aberration, the adjustments of the present embodiment can be used to correct for magnification chromatic distortion only. Also, if magnification chromatic aberration is corrected, this will make it possible to increase the number of primary electron beams (multibeam beamlets), thus enabling higher throughput for evaluation of samples such as wafers and masks.

Noise Reduction

In the electron beam inspection apparatus of the present invention, in order to perform high reliability inspections, the quantity of secondary electrons detected per pixel must be on the order of 4000 electrons/pixel. This requires high intensity beams.

When an electron gun is operated in the temperature-limited region of its current vs. temperature characteristic curve, there is a large amount shot noise. It is known, however, that when the gun is operated in the space-charge-limited region, the shot noise is reduced to approximately 13% of that in the temperature-limited region. Therefore, to most effectively improve the signal/noise (S/N) ratio of the signal, the electron gun should be operated in the space-charge-limited region. This will reduce, by a factor of $0.13^2 \approx 0.017$, the number of electrons/pixel that must detected to have the same S/N ratio.

An advantage of operating the electron gun in the temperature-limited region, however, is that in this region, the position of the electron beam crossover can be changed arbitrarily, without changing the brightness or emission current, by changing the Wehnelt voltage or control anode voltage. This makes it easy to align the direction of strongest electron beam emission from the electron gun with the area of the aperture plate containing the multiple apertures.

On the other hand, when the electron gun is operated in the space-charge-limited region, a change in the Wehnelt voltage or control voltage causes large changes in brightness and emission current, which makes it difficult to control the vertical position of the crossover. This is a problem because it makes it difficult to align the direction of strongest electron beam emission from the electron gun with the area of the aperture plate that has the multiple apertures.

The present invention provides an electron beam inspection apparatus in which the electron gun can be operated in the space-charge-limited region to thereby reduce the electron beam shot noise. An embodiment of such an electron beam inspection apparatus is described below.

Figure 55:
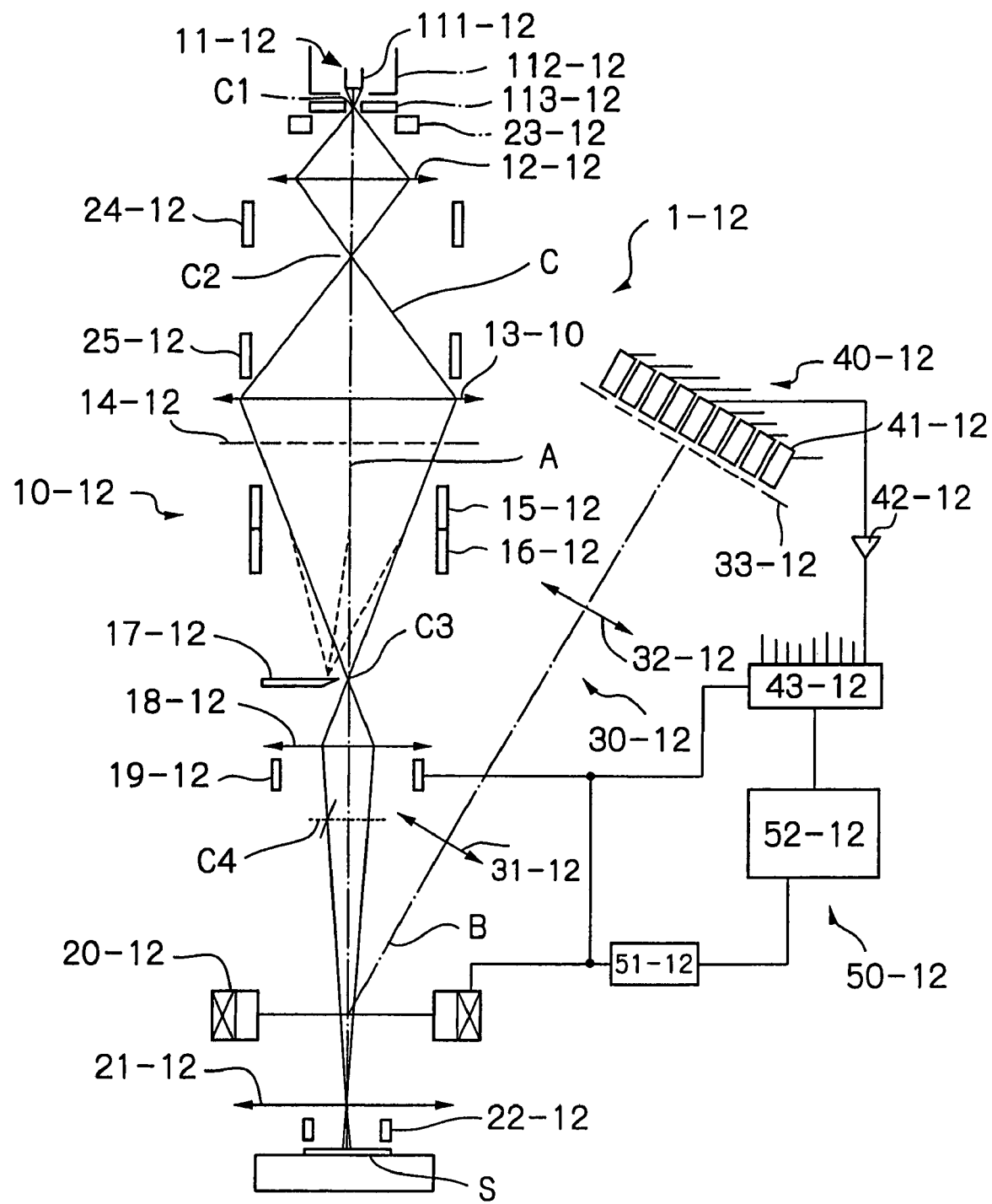
FIG. 55 is a schematic diagram of an electron beam inspection apparatus optical system, used to describe a method of reducing shot noise according to the present invention.

FIG. 55 shows a typical electron beam apparatus 1-12 having substantially the same configuration as those described earlier. The apparatus comprises a primary optical system 10-12; a secondary optical system 30-12; a detector unit 40-12; and a control unit 50-12. The primary optical system 10-12 comprises an electron gun 11-12;
condenser lenses 12-12 and 13-12 for converging the electron beams;
an aperture plate 14-12;
electrostatic alignment deflectors 15-12 and 16-12;
a knife-edge 17-12 for blanking;
a demagnification lens 18-12 for demagnifying electron beams passed through the aperture plate 14-12;
an electrostatic deflector 19-12;
an ExB separator 20-12; and
an objective lens 21-12.

All of the above are placed with the electron gun 11-12 in the top-most position, such that an optical axis A of the electron beams emitted from the electron gun 11-12 will be perpendicular to the surface of a sample S. Also, placed under the electron gun is an electrostatic axial alignment deflector 23-12, and placed between the condenser lenses 12-12 and 13-12, are electrostatic alignment deflectors 24-12, and 25-12. The cathode 111-12 of the electron gun 11-12 is constructed with a plurality of tips, equal in number to the electron beamlets to be emitted, and arranged concentric with the optical axis A. The electron gun 11-12 further comprises a Wehnelt electrode 112-12 and an anode 113-12 for controlling the electron gun within the space-charge-limited region by varying, to some extent, the Wehnelt bias.

The secondary optical system 30-12 comprises two electrostatic magnification lenses 31-12 and 32-12 placed along an optical axis B that is inclined with respect to the optical axis A from a point near the ExB separator 20-12; and an aperture plate 33-12 having formed therein, a plurality of apertures, arranged in a two-dimensional array.

The detector unit 40-12 comprises a detector 41-12, an amplifier 42-12, and an image processor 43-12. The control unit 50-12 comprises a deflector controller 51-12; and a computer 52-12, for controlling the image processor 43-12 and the deflector controller 51-12.

The operation of this electron beam inspection apparatus is the same as that of the systems described earlier. The operating point of the electron gun 11-12 can be controlled within its space-charge-limited region by varying, to some extent, the Wehnelt bias.

Figure 56:
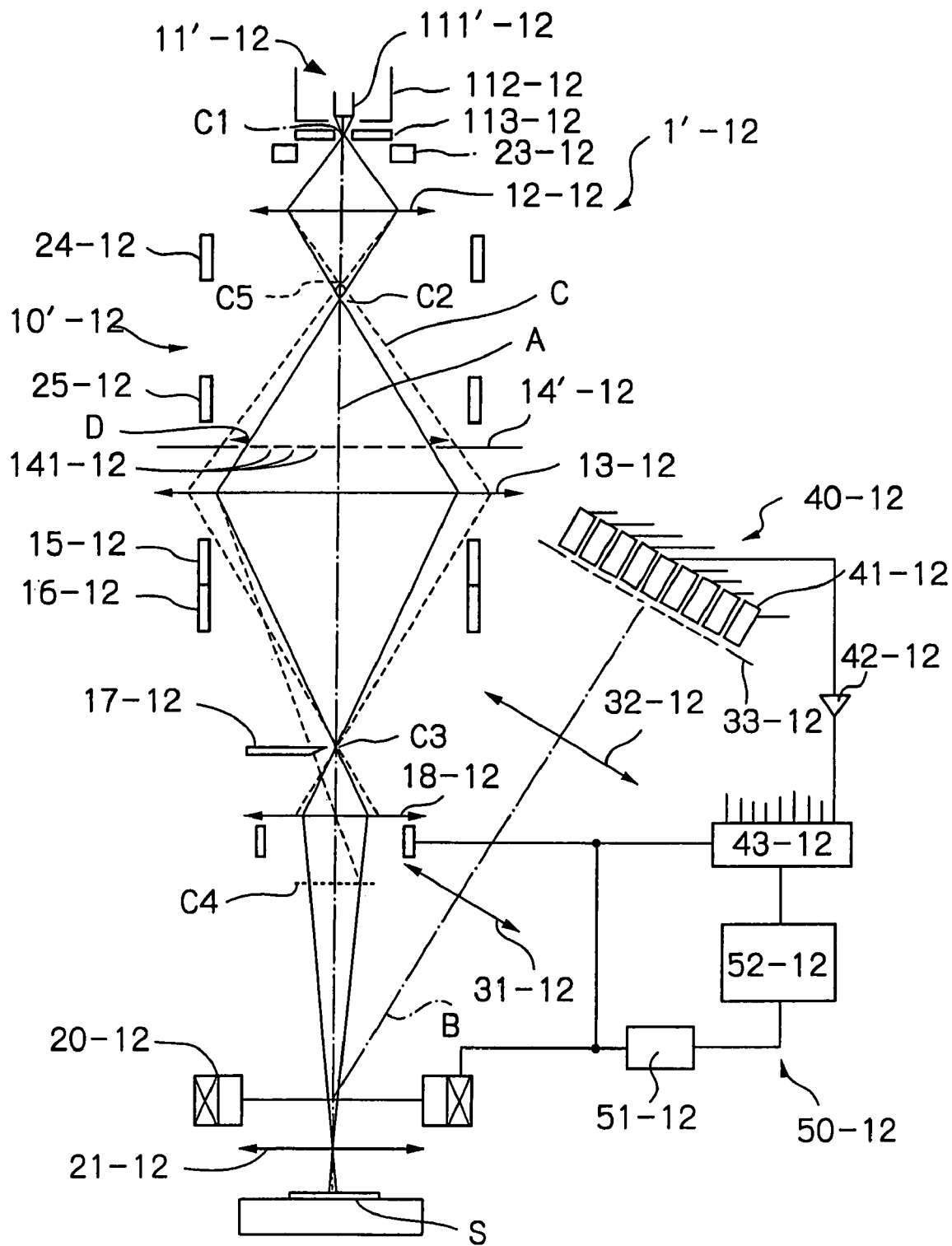
FIG. 56 is a schematic diagram of an electron beam inspection apparatus optical system, used to describe another method of reducing shot noise according to the present invention.

Another electron beam inspection apparatus 1'-12 is shown in FIG. 56. Components of the apparatus in FIG. 56 that are identical to corresponding components of the apparatus of FIG. 55 are assigned the same reference numbers in both drawings, and elements of FIG. 56 that have corresponding elements in FIG. 55 but are of different construction have the same reference numbers, but with a 'prime' (') symbol added.

As in the first embodiment, the electron beam inspection apparatus 1'-12 of the present embodiment comprises a primary optical system 10'-12; a secondary optical system 30-12; a detector unit 40-12; and a control unit 50-12.

The primary optical system 10'-12 comprises an electron gun 11'-12;
condenser lenses 12-12 and 13-12 for converging the electron beams;
an aperture plate 14'-12 having a plurality of apertures 141-12 therein;
electrostatic alignment deflectors 15-12 and 16-12;
a knife-edge 17-12 for blanking;
a demagnification lens 18-12 for demagnifying electron beams passed through the aperture plate 14'-12;
an electrostatic deflector 19-12;
an ExB separator 20-12; and
an objective lens 21-12.

All of the above are placed with the electron gun 11'-12 in the top-most position, such that an optical axis A of the electron beams emitted from the electron gun will be perpendicular to the surface of a sample S. Also, as in the primary optical system 10-12 of the first embodiment, placed under the electron gun is an electrostatic axial alignment deflector 23-12, and placed between the condenser lenses 12-12 and 13-12, are electrostatic alignment deflectors 24-12, and 25-12.

The cathode 111'-12 of the electron gun 11'-12 is constructed with a plurality of tips, equal in number to the electron beamlets to be emitted, and placed concentric with the optical axis A. This electron gun 11'-12 also comprises a Wehnelt electrode 112-12 and an anode 113-12, for controlling the electron gun within the space-charge-limited region by varying to some extent, the Wehnelt bias.

In this embodiment, the aperture plate 14'-12 is placed under a crossover C1 that is formed under the condenser lens 12-12, by the condenser lens 12-12, with the condenser lens 13-12 placed under the aperture plate 14'-12.

The secondary optical system 30-12, detector 40-12, and control unit 50-12 all have constituent elements and placements thereof that are exactly the same as in the first embodiment.

In the above configuration, a plurality of electron beams C emitted from the electron gun 11'-12 form a crossover C1 near the anode 112-12, and diverge therefrom at a fairly small angle. The diverging electron beams are then converged by the short-focal-length condenser lens 12-12 to form a crossover C2 near the condenser lens 12-12. The aperture plate 14'-12 is placed at a substantial distance from the crossover C2. The electron beams C diverging from crossover C2 irradiate the aperture plate 14'-12 and pass through the apertures 141-12 formed therein to become multibeam beamlets. These multibeam beamlets are converged by the condenser lens 13-12 to be imaged at the crossover C3. Placed at this location is the blanking knife-edge 17-12. The beamlets passed through the multiple apertures 141-12 are demagnified by the demagnification lens 18-12 to be projected at C4. After being focused at C4, the beamlets proceed on toward the sample S to be imaged by thereon by the objective lens 21-12. Commanded by the computer and deflector controller, the multibeam beamlets formed by the aperture plate 14'-12 are simultaneously scanned via the electrostatic scan deflector 19-12 over the surface of the sample S. After this point, operation is the same as in the apparatus of FIG. 55.

In both of the first and second embodiments described above, if the crossover C2 is moved vertically toward the electron gun to the position at point C5 of FIG. 56, the positions of the electron beams in the direction in which the strongest portions of the beams are emitted from the electron gun 11-12, 11'-12 can be directed such that the beams will expand outward on the aperture plate 14-12, 14'-12 (as indicated by the arrow D). Conversely, if the crossover C2 is moved vertically toward the position of the condenser lens 13-12, the positions of the electron beams in the direction in which the strongest portions of the beams are emitted from the electron gun 11-12, 11'-12 can be directed such that the beams are drawn inward on the aperture plate 14-12, 14'-12. In this manner, the direction of strongest electron beam emission can be adjusted to align it with the area containing the multiple apertures of the aperture plate 14-12, 14'-12. These adjustments can easily be performed by changing only the excitation of the condenser lens 12-12, without changing the operating conditions of the electron gun 11'-12. Therefore, the electron gun can be operated at a desired operating point within the space-charge-limited region such as to dramatically decrease the shot noise generated by the electron beam to approximately 1.8% of that experienced when operating in the temperature-limited region.

As described above, in the electron beam inspection apparatus illustrated in FIG. 55 and FIG. 56, (1) a dramatic reduction in shot noise can be achieved by operating the electron gun in the space-charge-limited region, which in turn results in lower secondary electron noise.

Abnormal Dose

In the above multibeam inspection apparatus, if an increase in throughput were to be sought by simply increasing the speed at which the stage is moved, this would decrease the total amount of beam current with which the sample is irradiated (hereinafter, dose), thus degrading the sample image. Thus when stage speed is increased, the beam current of the electron beams must also be increased.

For this reason, in prior multibeam inspection systems, stages were continuously scanned at high speed while continuously irradiating the sample with high current beams. Even when high speed scanning was performed under these conditions, however, there were times when the stage would stop or slow down for one reason or another. When such slowing or stopping of the stage occurred during high speed scanning, the high current beams would continue to irradiate the same spots or vicinities on the surface of the sample, causing an abrupt increase in dose. A sample can tolerate increased dose only within a limited range, however, and if the sample continues to be irradiated after the maximum allowable radiation dose has been exceeded, the sample could become contaminated or charged, or in the worst case, could even be destroyed.

In consideration of this problem, the present invention provides a multibeam inspection apparatus such that when the sample is being irradiated by electron beams as relative motion is effected between the beams and the sample, any abrupt increases in dose due to the reduced speed or stopping of this relative motion can be prevented, thereby protecting the sample. An embodiment of this aspect of the present invention is described below, with reference to the drawings.

Figure 57:
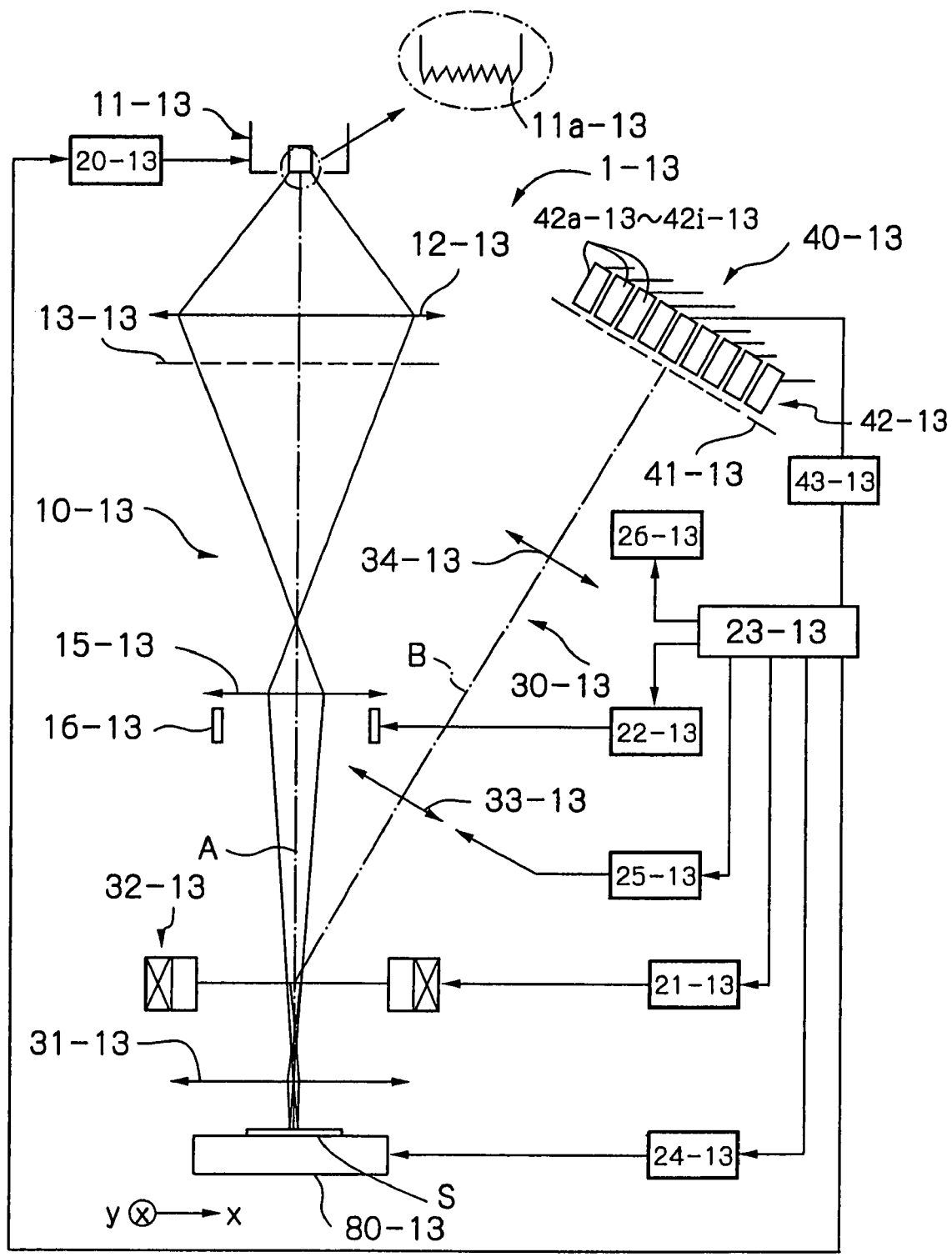
FIG. 57 is a schematic diagram of the optical system of an electron beam inspection system in a multibeam inspection apparatus with a dose control function incorporated therein.

FIG. 57 shows an example of a multibeam inspection apparatus having a dose control function incorporated therein. This multibeam inspection apparatus 1-13 has essentially the same configuration as that of the electron beam inspection apparatus described above, but the system in FIG. 57 is configured to have two selectable operating modes: an 'observation mode' in which the sample image is acquired with the stage stopped, and an 'inspection mode' in which the sample image is acquired with the stage moving at high speed. A particular feature of this multibeam inspection system 1-13 is that it has a 'sample protection mechanism' for protecting a sample on the stage if a fault condition occurs for one reason or another when the system is operating in inspection mode.

Like the apparatus described above, this multibeam inspection apparatus 1-13 comprises a primary optical system 10-13, a secondary optical system 30-13, a detector unit 40-13, and a vacuum chamber (not shown). An electron gun 11-13 is placed at the topmost position of the primary optical system 10-13. The electron gun 11-13 accelerates electrons emitted from its cathode by thermionic emission and converges them to be further emitted as beams. This electron gun 11-13 has a lanthanum hexaboride ($LaB_6$) cathode that is machined (as shown in the inset 11a-13 of FIG. 57) to enable multiple electron beams to be drawn from it.

Connected to the electron gun 11-13 is an electron gun control unit 20-13, for controlling an electron gun accelerating voltage Vac, and for turning the electron gun power supply on and off. Also provided are a gun alignment mechanism and gun aligner (neither of which is shown in the drawing) for adjusting the position, etc. of the electron gun 11-13.

Also, placed along an electron beam optical axis A, is a two-stage lens comprising the electrostatic lenses 12-13 and 15-13, a multi-aperture plate 13-13, and a primary deflector 16-13. Formed in the multi-aperture plate 13-13 are a plurality of apertures arranged in a straight line, for forming the electron beams emitted from the electron gun 11-13 into a plurality of primary beamlets.

The electrostatic lenses 12-13 and 15-13 of the primary optical system 10-13 are both rotation-symmetrical 3-electrode or 2-electrode electrostatic lenses. By optimizing the voltages applied to these lenses, the primary beamlets can be re-formed into beams having the desired dimensions without loss of emitted electrons. The lens voltages applied to the electrostatic lenses are controlled by a primary optical system control unit 21-13 connected to the primary optical system 10-13.

The primary deflector 16-13 may be either an electrostatic or electromagnetic deflector. For example, if the primary deflector 16-13 is configured as an 8-electrode electrostatic deflector, the paths of the primary beamlets can be deflected in the X direction by changing the voltage applied to opposite electrodes along the X axis; or in the Y direction by changing the voltage applied to opposite electrodes along the Y axis. The voltages applied to the electrodes of the primary deflector 16-3 are controlled by a primary deflector control unit 22-13 connected thereto.

The electron gun control unit 20-13, the primary optical system control unit 21-13, and the primary deflector control unit 22-13 are all connected to a host computer 23-13.

A stage 80-13 that is capable being moved in the X and Y directions with a sample L loaded thereon is also installed. A prescribed retarding voltage Vr (to be discussed later) is applied to the stage. A stage control unit 24-13 is connected to the stage 80-13. This stage control unit 24-13 drives the stage 80-13 in the X and Y directions, and reads (at a data rate, for example, of 10 Hz) the x,y position of the stage, using a laser interferometer (not shown in the drawing), and outputs an x,y position signal to the host computer 23-13. The stage control unit 24-13 also detects the travel speed of the stage 80-13 based on the x,y position readings, and outputs a speed signal to the host computer 23-13.

Internal to the secondary optical system 30-13 and placed along an optical axis B thereof, are an electrostatic objective lens 31-13, an ExB separator 32-13, a second electrostatic lens 33-13, and a third electrostatic lens 34-13. The electrostatic objective lens 31-13 might comprise, for example, three electrostatic electrodes (none of which are shown in the drawing), with prescribed voltages applied to the first and second poles from the bottom of the electrostatic objective lens 31-13 (i.e. the sample L end), and with the third electrode set to 0 potential. The configuration of such electrostatic objective lenses is well known to those skilled in the art.

The ExB separator 32-13 is a deflector that functions as an electromagnetic prism, wherein only charged particles that satisfy the Wien condition (E=vB, where v is the charged particle velocity, E is the electric field, B is the magnetic field, and E ⊥ B) (e.g. primary beam electrons) are passed through the separator in a no deflection, and the trajectories of all other charged particles (e.g., secondary electrons) are deflected.

The second and third electrostatic lenses (33-13 and 33-14) are both rotation-symmetrical lenses of the type referred to as unipotential or Einzel lenses, each with three poles. The operation of these electrostatic lenses is normally controlled by placing two outer poles at zero potential, and varying the voltage applied to a center pole.

The lens voltages of the electrostatic objective lens 31-13, the second electrostatic lens 33-13, and the third electrostatic lens 34-13; and the magnetic field of the ExB separator 32-13, are controlled by a secondary optical system control unit 25-13 connected to the secondary optical system 30-13.

The detector unit 40-13 comprises a multi-aperture plate 41-13, and a plurality of detectors 42-13. The multi-aperture plate 41-13 is placed in the image plane of the third electrostatic lens 34-13, with restrictions to prevent intermixing of secondary electrons from adjacent primary beamlets. Formed in the multi-aperture plate 41-13 are a plurality of apertures equal in number to, and arranged in a straight line matching that of, the apertures of the multi-aperture plate 133.

A detector 42-13 comprises a phosphor for converting electrons to light, and a photomultiplier tube (PMT) for converting light to an electrical signal. A strong electric field established between the multi-aperture plate 41-13 and the detectors 42-13 creates a convex lens effect near the apertures of the multi-aperture plate 41-13 to cause all secondary electrons approaching the apertures pass through the apertures. The detectors 42-13 are connected to the image processor unit 43-13.

The secondary optical system control unit 25-13 and the image processor unit 43-13 are connect to the host computer 23-13. A computer monitor 26-13 is also connected to the host computer 23-13.

Next, the primary beams and the secondary electron trajectories, etc. of a multibeam inspection apparatus 1-13 configured as described above will be described in sequence.

(Primary Beams)

The beam current at which the primary beam is emitted from the electron gun 11-13 is a function of the electron gun acceleration voltage Vac. (Hereinafter, the beam current of the primary beam as it is emitted from the electron gun 11-13 will be referred to as 'electron gun beam current Ia.') The primary beamlets from the electron gun 11-13, pass through, and are influenced by the lens action of, the primary optical system 10-13, to arrive at the primary deflector 16-13. When no voltage is applied to the electrode of the primary deflector 16-13, the primary beamlets are not influenced by the deflector action of that deflector; therefore, they pass through the primary deflector 16-13 to be injected into the center of the ExB separator 32-13. Next, the primary beamlets pass through the electrostatic objective lens 31-13 to effect multi-beam irradiation of the sample L.

The beam current of the primary beamlets irradiating the sample L (hereinafter 'irradiation beam current Ib.'), however, is lower, by far, than the above electron gun beam current Ia. However, since we have pre-knowledge of the relationship between the irradiation beam current Ib and the electron gun beam current Ia, and pre-knowledge of the relationship between electron gun beam current Ia and accelerating voltage Vac, then we also have pre-knowledge of the relationship between irradiation beam current Ib and accelerating voltage Vac.

Accordingly, the primary beam irradiation current Ib can be set to the desired value by controlling the electron gun 11-13 accelerating voltage Vac, through the electron gun control unit 20-13. The electron gun control unit 20-13 outputs information related to the irradiation beam current Ib settings to the host computer 23-13. As shown in Table 1, the irradiation beam current Ib is different in the observation and inspection modes (to be discussed later).

TABLE 1

|  | Observation Mode | Inspection Mode |
| --- | --- | --- |
| Primary Beam Irradiation Current Ib | 62.5 nA | 250 nA |

The shape of the region on the sample L that is irradiated by the primary beams, on the other hand, can be adjusted to the desired dimensions by controlling the primary optical system 10-13 lens voltages. The irradiation beam current Ib can be adjusted for uniform irradiation of the sample L between primary beamlets.

The relationship between dose Do, the total surface area S irradiated by the primary beamlets when the stage 80-13 is stopped (as it is in observation mode), and the irradiation time T of the primary beamlets, can be expressed by equation (1):

$$Do \propto Ib \times T/S \qquad (1)$$

Thus dose Do is proportional to irradiation beam current Ib and irradiation time T.

Also, the relationship between the dose Dv when the stage 80-13 is in motion (as it is in inspection mode, for example), and the speed of motion V of the stage 80-13 (V≠0) can be expressed by equation (2):

$$Dv \propto Ib/V/S \qquad (2)$$

Thus Dv is directly proportional to irradiation beam current Ib, and inversely proportional to speed of stage motion V.

There is a limit, however, to the amount of radiation that can be tolerated by the sample L, and if the sample continues to be irradiated after the maximum allowable radiation dose has been exceeded, the sample may become contaminated or charged, and in the worst case, could be destroyed. For this reason, data on the permissible dose range for each type of sample L is determined in advance and stored in the memory of the host computer 23-13. This permissible dose range data is then used by a sample protection mechanism to be described later.

The voltage applied to the primary deflector 16-13 is changed to deflect the primary beams as required to move the beams over the x,y positions of the irradiation regions of the sample L.

(Secondary Beams)

When a sample L is irradiated by primary electron beams, electron beams (hereinafter referred to as secondary beams) are caused to be emitted from the irradiated region of the sample L. These secondary beams are made up of at least one of three classes of electrons: secondary electrons, reflected electrons, and backscattered electrons. These secondary beams possess two-dimensional image information on the irradiated region. Also, because the primary beams radiate perpendicular to the surface of the sample, as described above, the secondary electron image information is clear and shadow-free.

A retarding voltage Vr is applied to the stage 80-13 on which the sample L is loaded. This sets up an electric field (an accelerating field for the secondary beams) between the sample L and an electrode of the electrostatic lens 31-13, causing the secondary electron beams emitted from the sample L to be accelerated toward the electrostatic objective lens 31-13.

The secondary beams are then converged by the electrostatic objective lens 31-13, deflected by the ExB separator 32-13, and passed through the second electrostatic lens 33-13, to be imaged at the apertures of the multi-aperture plate 41-13. At this time, the secondary beams released from the surface of the sample by the primary beams are imaged on apertures of the multi-aperture plate 4-13 corresponding to the apertures of the multi-aperture plate 13-13. That is, each secondary beamlet is imaged at the secondary aperture that corresponds to the primary aperture that formed the primary beamlet that produced it.

Because the imaging of the secondary beams from the sample L is performed by the electrostatic objective lens 31-13 in cooperation with the second electrostatic lens 33-13, lens aberrations can be suppressed The two-dimensional multibeam image formed at the apertures of multi-aperture plate 41-13 is first converted to light by the phosphor elements of the detectors 42-13, and then converted to an electrical signal by the PMTs.

At this point, correspondence between the terminology used in the description of this embodiment and that used in the related claims will be shown. That is, the 'motion device' of the claims corresponds to the stage 80-13, and the stage control unit 24-13 of the present embodiment;

the 'measurement device' of the claims corresponds to the electron gun control unit 20-13, the stage control unit 24-13, and the host computer 23-13 of the present embodiment;

the 'decision device' of the claims corresponds to the host computer 23-13 of the present embodiment; and the 'control device' of the claims corresponds to the primary deflector 16-13, the primary deflector control unit 22-13, and the host computer 23-13 of the present embodiment.

Next, the operation of a multibeam inspection apparatus 1-13 configured as described above will be described. The multibeam inspection apparatus 1-13 has two operating modes: an 'observation mode,' in which the image of a sample L is acquired with the stage 80-13 stopped, and an 'inspection mode,' in which the image of the sample L is acquired with the stage 80-13 moving at high speed. In both modes, the multibeam inspection apparatus 1 is adjusted so that the beam size, on the sample L of each beamlet will be 0.1 micron.

First, the observation mode will be described. In the observation mode, the stage control unit 24-13 drives the stage 80-13 in the X and Y directions as required to position the region of the sample L surface to be observed (e.g., a region having locations in which there are defects) within the irradiation region of the primary beams. Once the stage has been properly positioned, it is stopped. The electron gun control unit 20-13 controls the electron gun 11-13 accelerating voltage Vac as required to set the primary beam irradiation beam current Ib to 62.5 nA (refer to Table 1). Signals from the image processor unit 43-13 are sent, in sequence, based on an observation timing signal from the host computer 23-13.

In observation mode, the image of a region of the sample L to be observed (e.g., a region having defect locations) can be displayed constantly on the monitor 26-13. Thus the observation mode can be used to make various adjustments to the system while taking (and viewing) images of a prescribed test pattern. Such adjustments might include adjustments to correct focus and aberration of the primary optical system 10-13 and/or the secondary optical system 30-13, or to adjust the detector 42-13 brightness, etc., Next, the operation of the system in terms of acquiring sample images in the inspection mode will be described. In this mode, the electron gun control unit 20-13 controls the electron gun 11-13 accelerating voltage Vac to set the primary beam irradiation beam current Ib to 62.5 nA (see Table 1).

The image processor 43-13 supplies drive pulses based on an observation timing signal from the host computer 43-13, causing SEM images to be formed from the primary deflector 16-13 scan signal and the detector 42-13 intensity signal.

In inspection mode, because the stage 80-13 is moved at high speed as sample images are being taken, consecutive images covering an entire sample, or a comparatively large portion thereof, can be acquired in a short amount of time. In this mode, after the acquisition of sample images has been completed, the host computer 23-13 executes an image data-to-template matching process to identify defect locations on the sample L. To speed up the inspection process in this mode, the speed of motion of the stage 80-13 is increased, the scan signal sent to the primary deflector 16-13 is set to a higher scan rate, and the irradiation beam current Ib of the primary beam is also increased by an amount corresponding to the increase in stage speed and transfer rate.

Thus in the inspection mode, the stage is constantly being moved at high speed, and the sample constantly irradiated at high beam current, to achieve high-speed inspection. As stated earlier, however, if the stage should stop or slow down for one reason or another during such high speed scanning, the high current beams would continue to irradiate the same spots or vicinities on the surface of the sample, causing an abrupt increase in dose (see equations (1) and (2)). A sample L, can tolerate increased dose only within a limited range, however, and if it continues to be irradiated after the maximum allowable radiation dose has been exceeded, contamination or charge-up of the sample L could result, and in the worst case, the sample could be destroyed. For this reason, a sample protection mechanism has been incorporated in the present embodiment of the multibeam inspection apparatus, for protecting the sample L. This protection mechanism is described below.

Figure 58A:
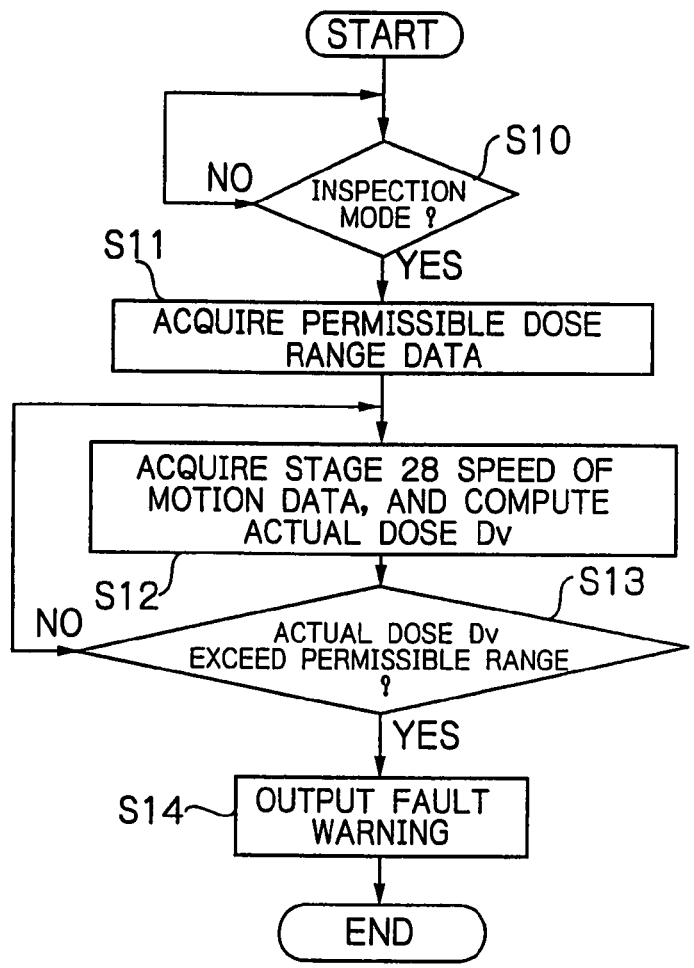
FIGS. 58(a) and (b) are flow diagrams showing the operational flow in one embodiment of a sample protection mechanism.
Figure 58B:
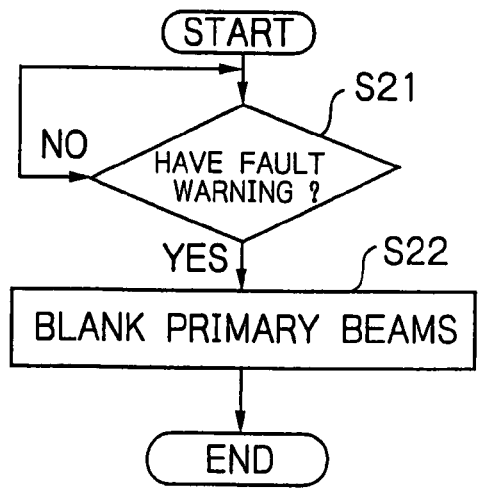

Shown in FIGS. 58(*a*) and (*b*) are flow diagrams for one embodiment of the sample protection mechanism. As shown in FIGS. 58(*a*) and (*b*), when the host computer 23-13 receives an external 'activate inspection mode' command input (S10), it acquires permissible dose range data for the sample L from memory (S11).

Next, the host computer 23-13 acquires a signal input from the stage control unit 24-13 relating to the speed of motion V of the stage 80-13. Based on this speed of motion V, the primary beam irradiation beam current Ib, and the area S of the irradiation region (equation (2)), the host computer computes an actual radiation dose Dv for the sample L (S12).

Then, in Step S13, the host computer 23-13 compares the permissible dose data acquired in Step S11 with the actual dose Dv computed in Step S12. If the actual dose Dv is less than the maximum permissible dose, execution returns to, and repeats, Step S12. Therefore, as long as the actual dose Dv is less than the maximum permissible dose, the inspection mode sample image acquisition operation continues as described above.

On the other hand, if the actual dose Dv computed by the host computer 23-13 in Step S12 exceeds the maximum permissible dose, the inspection operation in progress is deemed to be faulty, and a fault warning is output to the primary deflector control unit 22-13 (S14).

When the primary deflector control unit 22-13 receives the fault warning from the host computer 23-13 (S21), it applies blanking voltage to the primary deflector 16-13, thereby deflecting the primary beams by a large amount (thus blanking the beams) (S22). This prevents the sample L from being irradiated by the high-beam-current primary beam. Consequently, a situation in which the sample L would have been contaminated, or in the worst case, destroyed, has been avoided.

Moreover, although in the description of the above embodiment, an example was described wherein a fault warning was output from the host computer 23-13 to the primary deflector control unit 22-13, in order to cause the primary deflector 16-13 to blank the primary beams, the present invention is not limited to this method. For example, the host computer 23-13 may instead be caused to output a fault warning to the electron gun control unit 20-13, which would then turn off the power supply for the electron gun 11, to thereby stop the emission of electron beams from the electron gun 11-13. Also, in cases where a deflector in addition to the primary deflector 16-13 is provided in the path of the primary beam, the same kind of blanking control as that described above may be performed, using this other deflector.

In addition, in the above described embodiment of the sample protection mechanism, the primary beams were completely shut off in response to a fault warning from the host computer 23-13, thus putting the system in a state wherein the sample L was not irradiated at all by the primary beams. Sudden large increases in dose may, however, also be prevented by controlling irradiation by the primary beam such that the current density of the primary beam (=irradiation beam current Ib/irradiated region area S) is reduced. Specifically, there is a method for using the primary deflector 16-13 to deflect the primary beams over a large area at a rapid scan rate so that they will not remain in the same spot over a sample irradiation region. Methods that use the primary optical system 10-13 to enlarge the cross-section of the primary beam in order to increase the area S of the irradiation region, thereby reducing the current density of the primary beams, can also prevent sudden large increases in dose. Similarly, methods wherein the electron gun 11-13 acceleration voltage Vac is controlled to reduce the primary beam electron gun beam current Ia can also prevent large increases in dose.

Moreover, although in example of the embodiment described above, the actual dose Dv was computed based on the speed of motion of the stage 80-13 as detected by the stage control unit 24-13, the present invention is not limited to this method. For example, since an increase in the dose of the sample L will be accompanied by an increase in the volume of secondary electrons contained in the secondary beams emitted from the sample, the volume of secondary electrons may instead be detected, and the actual dose Dv then determined from the relationship between the quantity of secondary electrons in the secondary beams and the sample L dose. (The quantity of secondary electrons in the secondary beams can be measured by periodically sampling the output of the detector 42-13.) In addition, since an increase in the sample L dose will also be accompanied by brighter sample images with lower contrast ratios, the contrast ratios of the sample images may be detected, and the actual dose Dv then determined from the relationship between this contrast ratio and the sample L dose. (The contrast ratios of the sample images can be determined by comparing the average value of the detector pixel density values stored in the internal memory of the image processor unit 43-13 with a threshold density value determined in advance.)

Also, in the above embodiment, data on permissible dose ranges for samples L was stored in the memory of the host computer 23-13, and a decision as to the inspection mode fault status was then made by comparing the actual dose Dv against this permissible dose range data. The present invention, however, is not limited to this method. For example, data on permissible stage motion speed ranges for the stage 80-13 may instead be computed in advance based on the permissible dose range data for various samples, and these computed data stored in the memory of the host computer 23-13. In this method, the inspection mode fault status decision is made by comparing the actual speed of the stage 80-13 with the permissible stage motion speed range data.

Similarly, permissible ranges of secondary beam electron quantity may be computed in advance based on sample L permissible dose data, and this permissible secondary electron quantity data stored in the memory of the host computer 23-13. In this method, the inspection mode fault status decision is made by comparing the actual secondary electron quantity with the permissible secondary electron quantity data computed above.

In addition, permissible ranges of image data contrast ratio may be computed in advance based on sample L permissible dose data, and this permissible image contrast ratio range data stored in the memory of the host computer 23-13. In this method, the inspection mode fault status decision is made by comparing the actual image contrast ratio with the permissible image contrast ratio range data computed above.

Also in the above embodiment, the primary beams were not deflected (i.e., the irradiation regions were not moved), while sample images were being taken in the inspection mode, but it is also possible to implement the present invention such that the primary beams are deflected (and the irradiation regions moved) while sample images are being acquired.

Moreover, the sample protection mechanism of the present invention as described above can be applied to either multi-beam or single beam electron beam apparatus (including single beam SEM), as long the system configuration is such that relative motion is effected between the primary beam and the sample during acquisition of sample images.

It can be understood from the foregoing, then, that according to the above electron beam inspection apparatus, in systems wherein relative motion is maintained between the sample and the electron beams during irradiation of the sample by the electron beams, abrupt increases in dose due to slowing or stopping of the above relative motion can be prevented, to thereby protect the sample. This provides improved reliability for high-beam-current, high-speed (in particular, high-scan-rate) inspection processes.

Control Elements for Deflectors, Wien Filters, Etc.

Figure 61:
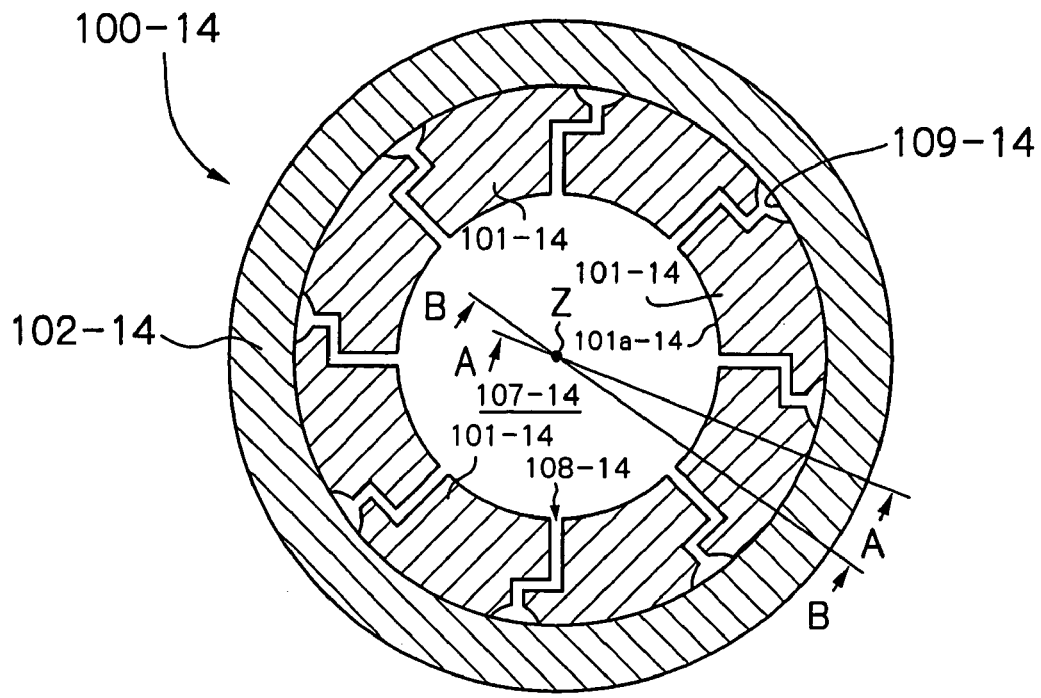
FIG. 61 shows a top view of a prior electrostatic deflector.
Figure 62A:
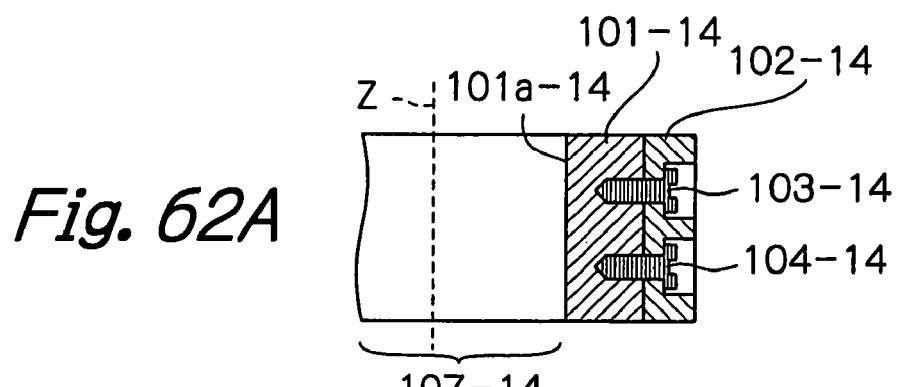
FIGS. 62(a) and (b) show cross-section views of section A-A and B-B, respectively of FIG. 61.
Figure 62A:
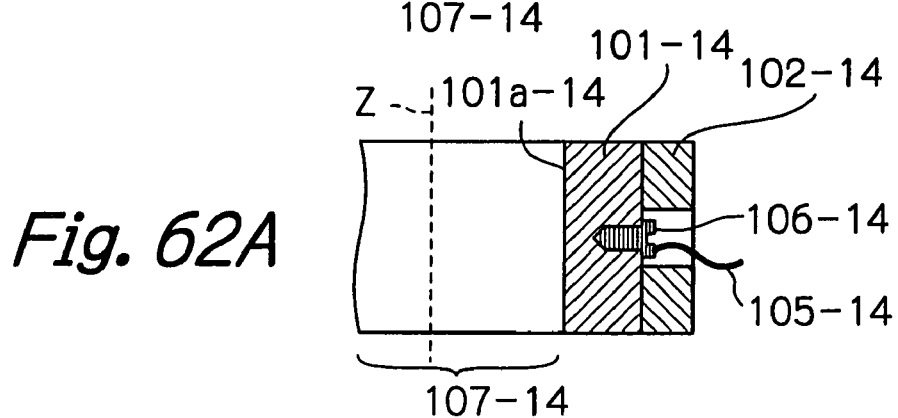

In the electron beam inspection apparatus described above, the electron optical systems are made up of elements such as electrostatic deflectors, electrostatic lenses, and Wien filters. FIG. 61 shows a plan view of a prior electrostatic deflector 100-14. Shown in FIGS. 62(a) and 62(b), respectively, are cross-sections of sections A-A and B-B of FIG. 61. The electrostatic deflector 100-14 has eight metal electrodes 101-14, each of which is fastened to the inside wall of an insulating outer cylinder 102-14 by fastening bolts 103-14 and 104-14 (FIG. 61 and FIG. 62(a)). Wires 105-14 for applying voltage to each of the metal electrodes 101-14 are secured directly to the electrodes using wiring screws 106-14 (FIG. 62(b)).

In this electrostatic deflector 100-14, an electrostatic field responsive to the voltages applied to the metal electrodes 101-14 is formed within a space 107-14 enclosed by the inward facing surfaces 101-14a of the metal electrodes 101-14. Therefore, a charged particle beam passing through the space 107-14 along a center axis Z thereof, will be deflected responsive to the electrostatic field formed therein.

Gap portions 108-14 are formed between each pair of adjacent metal electrodes 101-14. These gap portions 108-14 are formed in a shape that extends outward from the space, not in a straight line, but by making two sharp turns before arriving at the insulating outer cylinder 102-14. This is done to avoid having a direct view of the exposed portions 109-14 of the insulating outer cylinder 102-14 from a charged particle beam passing through the space 107-14. This configuration prevents the insulating outer cylinder 102-14 from becoming electrically charged, and thus makes it possible to effect precise control of the electrostatic field within the space 107-14 responsive to the voltages applied to the metal electrodes 101-14.

However, there was a problem with the above electrostatic deflector 101-14, in that it had a complex structure using a large number of parts, which made cost and size reduction difficult. Also the eight metal electrodes 101-14 that constituted the electrostatic deflector 100-14 were obtained by dividing a metal cylinder into sections after it had been bolted to the inside of the insulating outer cylinder 102-14, which made it difficult make any improvements in the accuracy of the angles at which the electrodes were divided, or the circularity of the space 107-14 enclosed by the inside surfaces 101a-14 of the metal electrodes 101-14.

This led to a proposal for replacing these metal electrodes 101-14 with plated electrodes formed on an insulator by a surface process such as electroplating. The motivation for using plated electrodes was to eliminate the electrode mounting bolts, and provide smaller deflectors with lower parts counts.

As in the prior electrostatic deflector 100-14 described above, however, in deflectors with plated electrodes, when wires for applying voltage to the electrodes were fastened directly to the plated electrodes with screws, the electrodes could possibly be left with surface openings. Such openings in the electrodes distorted the electrostatic field distribution within the space through which the charged particle beam passed, such that deflection of the charged particle beam could not be accurately controlled.

This led to a configuration in some electrostatic deflectors wherein a support portion of the insulator on which the plated electrodes were formed was caused to protrude (along with the electrodes) from the end of an insulating outer cylinder, and the wires were attached to this protruding portion. This eliminated the holes in the electrodes, but the construction related to the wiring was complex, and was such that insulated wire coverings could possibly be visible through the gaps between adjacent electrodes.

The need for charged particle beam control elements using plated electrodes exists not only for electrostatic deflectors, but also for other elements, such as electrostatic lenses. For these other elements as well, there is a need for a better way of connecting the voltage application wires to the plated electrodes.

To address the above problem, the present invention provides a charged particle beam control element (deflector, lens, etc.) wherein it is possible, through a simple structural configuration, to accurately secure the surfaces of electrodes formed on an insulator by a surface process such as electroplating, etc., and also to connect wires to these electrodes for application of voltages thereto.

Figure 59:
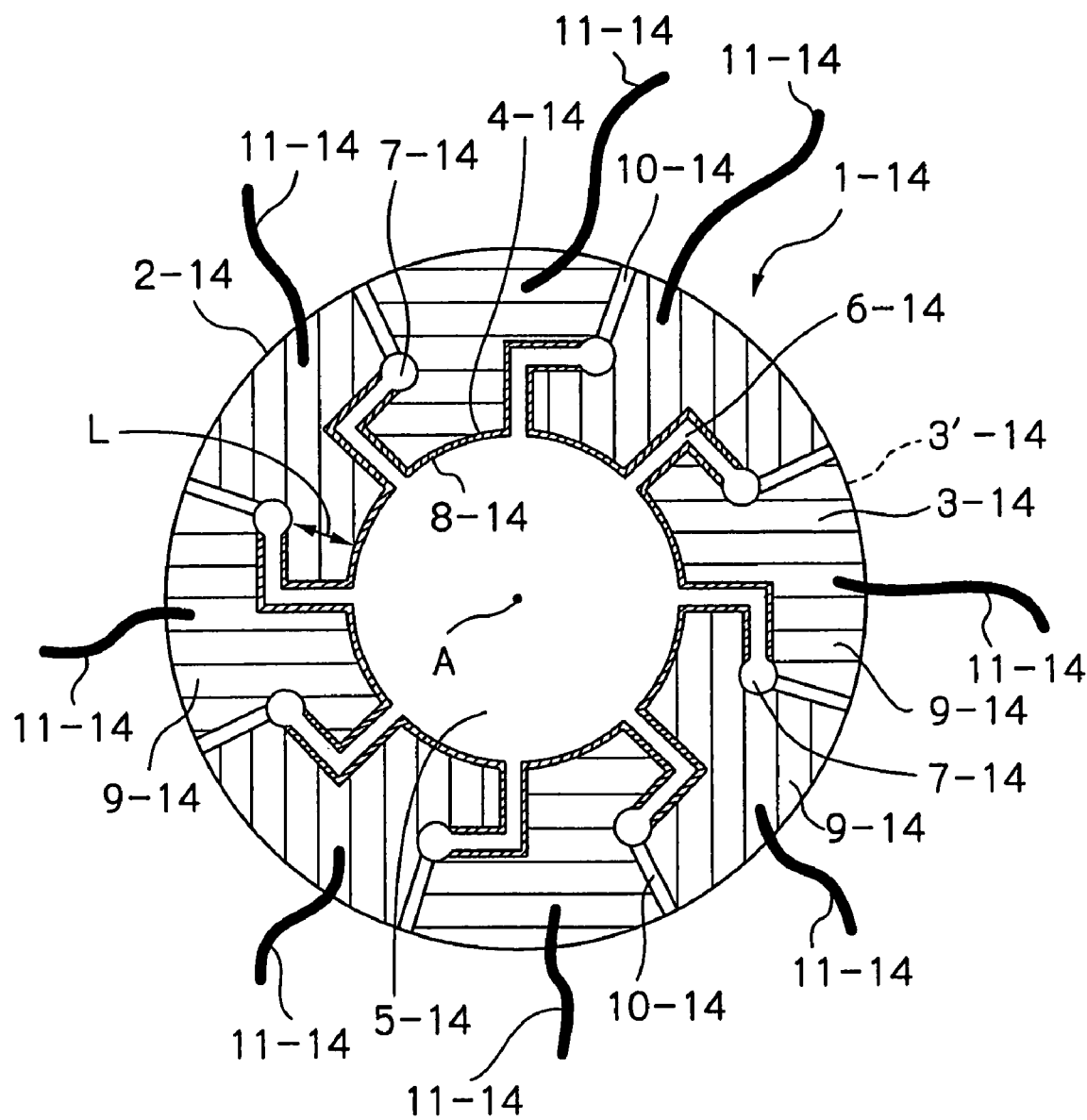
FIG. 59 is a simplified drawing showing the construction of one embodiment of one of the charged particle beam control elements of the present invention.
Figure 60:
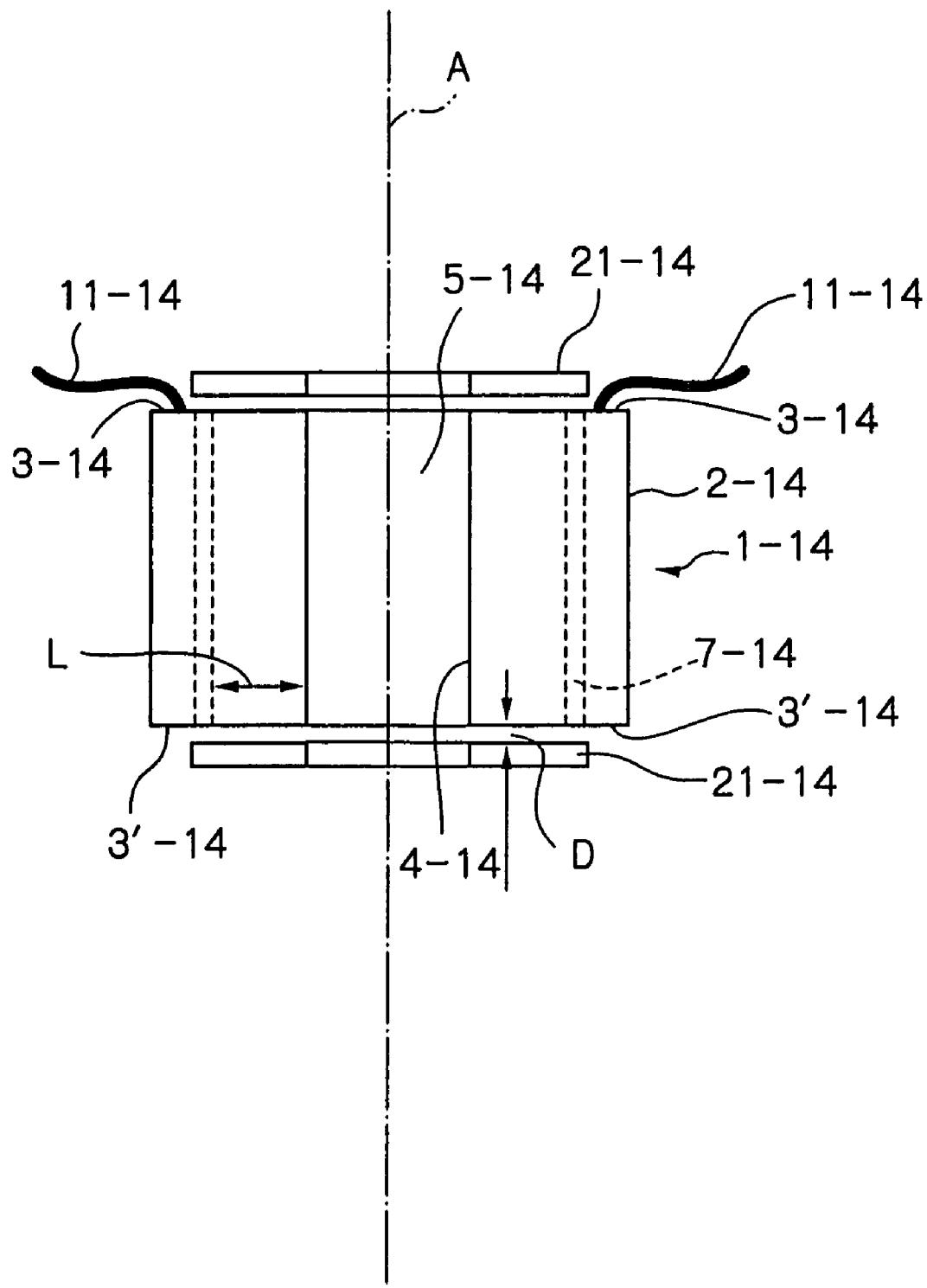
FIG. 60 shows a cross-section view of the charged particle beam control element of FIG. 59.

Shown in FIG. 59 is a simplified drawing of an embodiment of one of the charged particle beam control elements of the present invention, as used in a deflector or Wien filter FIG. 60 shows a cross-section of the charged particle beam control element. In FIGS. 59 and 60, the charged particle beam control element has a base 1-14 made of an insulating material. The base 1-14 is a cylinder that has an axis A at its center, and a structure defined by a through-hole 5-14 that is formed by an outer surface 2-14, and end surfaces 3-14 and 3'-14. The through-hole 5-14 is concentric with the axis A, which is coincident with the optical axis during use. Slots 6-14 dividing the electrodes are formed in the cylindrical base 1-14 in a direction parallel to the axis A and extending radially outward therefrom. As shown in the drawing, each of the slots 6-14 is formed with a sharp bend identical to that of the other slots, and with a circular through-hole 7-14 at its terminal end. In addition, as shown in FIG. 60, conductive shield cylinders 21-14 having the same diameter as the through-hole 5-14, are placed at the top and bottom, respectively, of the base 1-14 of the charged particle beam control element (i.e., near the opposite end surfaces 3-14 and 3'-14 thereof).

In the structure, as described, a metallic coating is applied to the end surfaces 3-14 and 3'-14 opposite an inner surface 4-14, except for non-conductive surfaces 10-14 thereof, which are provided for insulation.

Specifically, a plurality of electrodes 8-14 are formed on the inner surface 4-14, separated from each other by the slots 6-14, as indicated by diagonal-line hatching in FIG. 59. Also formed on the respective end surfaces 3-14 and 3'-14, are a plurality of conductors 9-14, each of which is electrically connected to the electrode 8-14. A metallic coating is also applied to the inside surfaces (also indicated by diagonal-line hatching) of the slots 6-14, which extend outward from the electrodes 8-14 formed in the inner surface 4-14, to the through-holes 7-14. Metallic coating is not applied, however, to the inside surfaces of the through-holes 7-14, or the end surface portions 10-14 extending outward from the through-holes 7-14 to the outer surface 2-14. In this manner the slots 6-14 are electrically isolated from each other by the non-conductive surface portions 10-14, while a plurality of electrically continuous portions are formed from the electrically connected electrodes 8-14 and conductors 9-14. In the embodiment of FIG. 59, 8 slots 6-14 are formed, thus there are also 8 sets of electrically interconnected electrodes 8-14 and conductors 9-14. If required, additional conductors connected to the above conductors 9-14 may also be formed on the outer surface 2-14.

Fine wire is used for the wires 11-14 for the electrodes 8-14, with the fine wires bonded either to the outer surface 2-14, or one of the end surfaces 3-14 and 3'-14. If the wires 11-14 are brought out from the outer surface 2-14, it makes the outside diameter of the charged particle beam control element 1-14 larger, while extra space is required in the axis A direction of the charged particle beam control element if they are brought out from the end surfaces, 3-14 and 3'-14. FIG. 59 shows an example in which the wires 11-14 are brought out from one of the end surfaces 3-14.

Moreover, in the present invention,] it is preferred that the relation L/D<4.0 be satisfied, where, (as indicated in FIG. 60), D is the distance between the shield cylinders 21-14 in the surfaces thereof that include the axis A and the opposing through-holes 7, and the end surfaces 3-14 of the base 1-14; and L is the radial distance between the surfaces of the electrodes 8-14 on the ends thereof nearest the axis A, and the surfaces of the through-holes 7-14 on the sides thereof nearest the axis A.

If this condition is met, when an electrical charge develops on the inner surfaces of the through-holes 7-14 of the base 1-14, the effect of the electrical potential resulting from that charge on a charged particle beam passing through near the axis A will be less than $1/1000$.

The charged particle beam control element shown in FIG. 59 can be used as an electrostatic deflector or ExB separator/Wien filter in an electron beam inspection apparatus as described above.

As will be understood from the above description, through the charged particle beam control element of the present invention, the surfaces of electrodes formed on an insulating surface by a surface process such as electroplating can be accurately secured, and wires can be connected to these electrodes for application of voltage thereto, in a simple structural configuration, to thus contribute to size and cost reduction of charged particle beam control elements and charged particle beam apparatus, while also providing more precise control of charged particle beam paths by the charged particle beam elements.

Semiconductor Device Fabrication Method

As is clear from the above discussion, the inspection apparatus of the present invention is capable of high throughput sufficient to enable performance of appropriate inspections of samples such as wafers currently undergoing a fabrication process, without holding up the process. A semiconductor device production method designed to include the in-process performance of such inspections will be described with reference to FIGS. 63 and 64.

Figure 63:
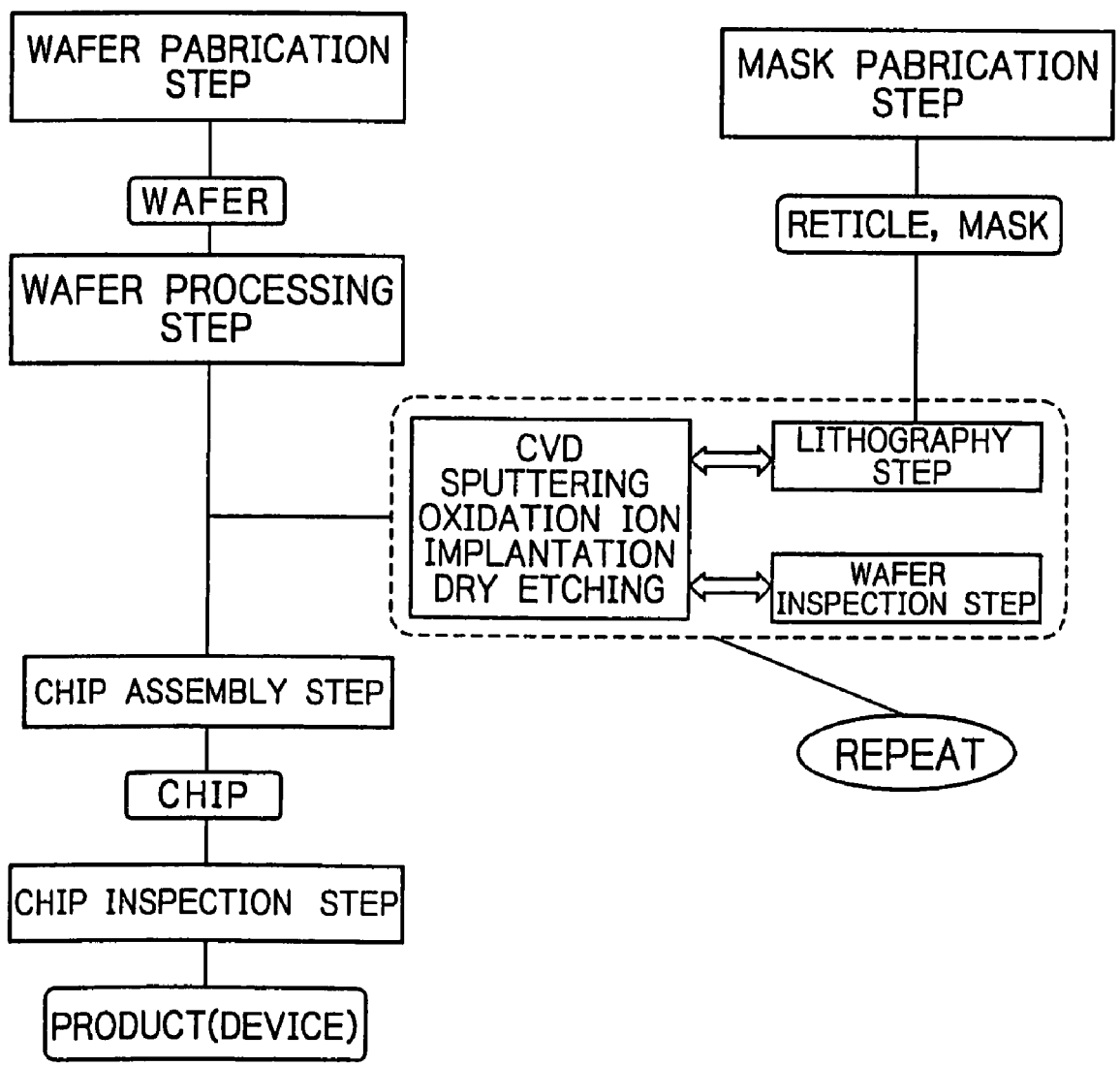
FIG. 63 is a flow chart showing the steps of a device fabrication method in which the inspection apparatus of the present invention is used to perform in-process inspection of wafers.

FIG. 63 shows a flow chart for one embodiment of the semiconductor device production method of the present invention. This embodiment comprises the following steps:
(1) A wafer fabrication step for fabricating a wafer (or a wafer preparation step for preparing a wafer).
(2) A mask fabrication step for fabricating a mask (or a mask preparation step for preparing a mask) to be used for exposures.
(3) A wafer processing step for performing required machining (etching) processes on a wafer.
(4) A chip assembly step for dicing (cutting out) individual chips from the multiple chips formed on a wafer and assembling them to an operational state.
(5) A chip inspection step for inspecting the completed chips.

Each of the above main steps comprises a number of sub steps. Within these main steps, one main step that has a decisive influence on the performance of the semiconductor devices produced is Step (3) the wafer processing step. In this step, patterns for the designed circuit are formed in sequential layers, one on top of the other (a large number of such layers for a device that will operate as a memory or MPU). Therefore the wafer processing step further comprises the following steps:
(1) A membrane forming step (using CVD, sputtering, etc.), for forming dielectric films for insulating layers, and metal thin films for wiring and electrodes.
(2) An oxidation step, for oxidizing these thin film layers and wafer substrates.
(3) A lithography step using a mask (reticle), for selectively etching the membrane layers, wafer substrates, etc. to form resist patterns.
(4) An etching step (using dry etch technology, etc.), for machining the thin films or substrates to conform to the resist pattern.
(5) An ion implantation/impurity diffusion step.
(6) A resist stripping step.
(7) An inspection step, for inspecting processed wafers.

Moreover, these wafer processing steps are repeated for each layer as required to manufacture semiconductor devices what will operate as designed.

Figure 64:
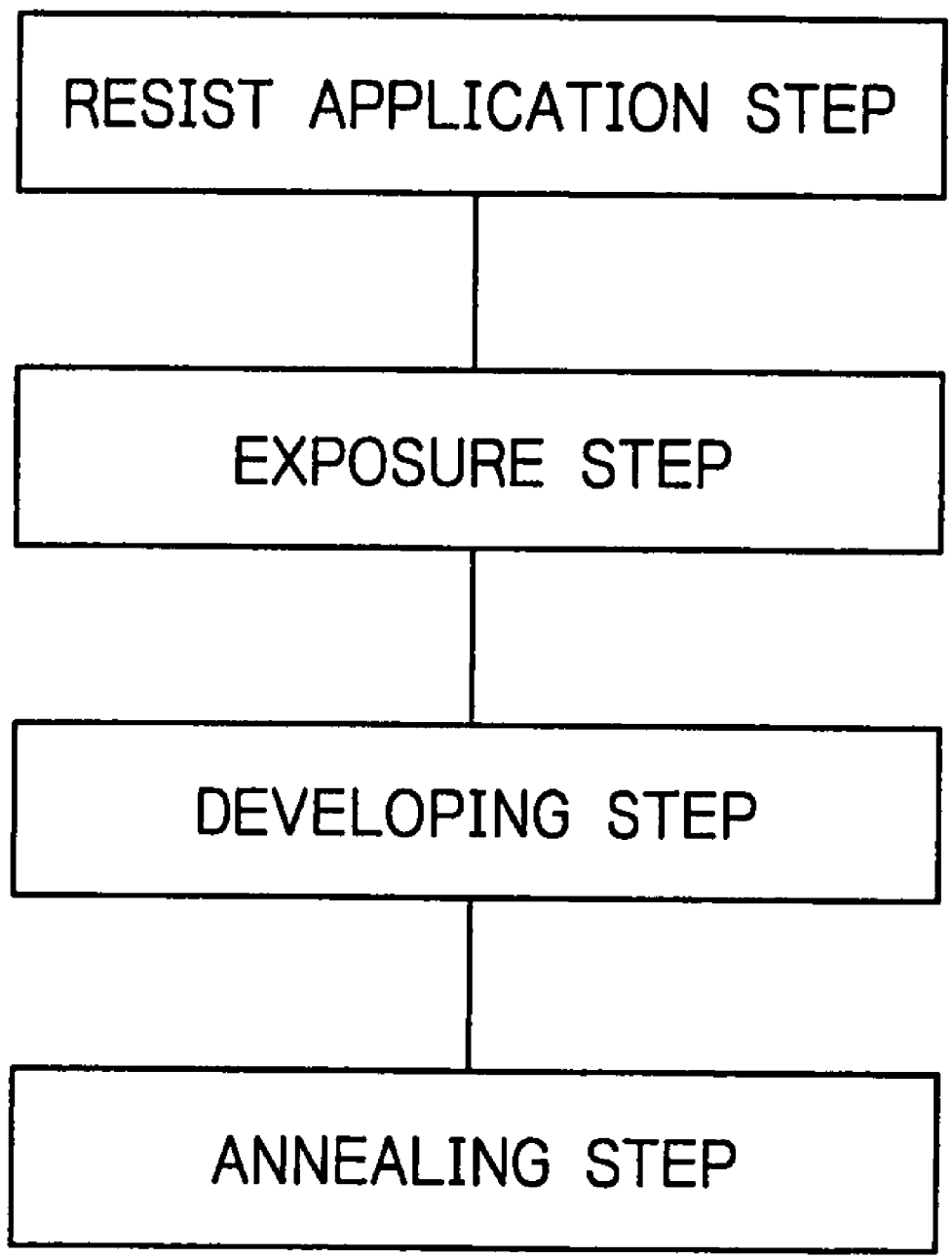
FIG. 64 is a flow chart for the lithography step of the method of FIG. 63.

FIG. 64 is a flow chart for the lithography step, which forms the nucleus of the wafer processing step of FIG. 63. The lithography step includes the following steps:
(1) A resist application step, for applying a coat of resist to a wafer that had a circuit pattern formed on it in preceding steps.
(2) An exposure step, for exposing the resist.
(3) A developing step, for developing the exposed resist to obtain a resist pattern.
(5) An annealing step, for stabilizing the developed resist pattern.

The above semiconductor device fabrication steps (wafer processing step, lithography step, etc.) are well known, and should require no further explanation.

In the above step (7), the wafer inspection step, if the defect inspection methods and defect inspection apparatus of the present invention are used, it will be possible to perform high-throughput inspection even of semiconductor devices having extremely fine patterns. This will make inspection of 100% of manufactured devices feasible, which will improve product yield and prevent defective devices from being shipped.

A number of embodiments of the invention were described above, but the present invention is not limited to these embodiments, and many variations thereof may be made without deviating from the scope of the invention.

What is claimed:

1. An electron bean apparatus comprising
a plurality of optical systems, each of which comprises:
an electron beam irradiating means, for irradiating a sample with primary electron beams, and scanning the sample by deflecting an incident angle of the primary electron beams within a prescribed range;
a deflecting/separating means for deflecting secondary electron beams, which are generated by irradiation of the primary electron beams onto the sample, in a prescribed direction with respect to an optical axis of the electron beam irradiating means; and
a detecting means for detecting the secondary electron beams deflected by the deflecting/separating means, wherein:
said optical systems are arranged in two rows, such that paths of the secondary electron beams deflected by the deflecting/separating means do not interfere with each other;
said optical systems are each capable of evaluating the sample by scanning different regions on the sample with their primary electron beams and detecting the respective secondary electron beams emitted from each of the respective regions.

2. An electron beam apparatus as recited in claim 1, wherein: in each of the plurality of optical systems,
the electron beam irradiating means irradiates a plurality of primary electron beams on the sample; and
the detecting means uses a plurality of detector elements, which are separated from each other, to detect the plurality of secondary electron beams generated by irradiation of the plurality of primary electron beams.

3. An electron beam apparatus as recited in claim 2, wherein the plurality of optical systems are arranged in a single row, and the paths of the secondary electron beams are arranged substantially perpendicular to a direction of the row of the optical systems; and
evaluation of the sample is enabled by movement of the sample in a direction substantially perpendicular to the direction of the row.

4. An electron beam apparatus as recited in claim 3, wherein the evaluation of the sample includes, at least, any one of an inspection for any defect of the sample, a measurement of a line width of a pattern formed on the sample, a measurement of electrical potential of the pattern, and a measurement of movement of the sample by irradiation of primary electron beams having a short pulse duration.

5. A charged particle beam control element for controlling a charged particle beam with an electrostatic field, the charged particle beam control element comprising:
a base made from a cylindrical insulator and having a through-hole therein;
a plurality of electrodes that are electrically insulated from each other and that are formed by a surface process performed on an inner surface of the base;

a plurality of conductors formed by said surface process on at least an end surface of the base, such that they are electrically connected to the respective electrodes; and wires connected to the respective conductors.

6. A charged particle beam control element as recited in claim 5, wherein the base has slots that electrically isolate the electrodes and conductors from each other, whereby film-less surfaces for insulating the conductors from each other are provided in the surface on which the plurality of conductors are formed.

7. A charged particle beam element as recited in claim 6, wherein a shielding conductor is placed a prescribed distance away from said end surface, with said prescribed distance being less than the distance between said film-less surface portions of the slots and the electrode surfaces.

* * * * *